(12) United States Patent
Calle et al.

(10) Patent No.: US 11,648,280 B2
(45) Date of Patent: May 16, 2023

(54) TISSUE ENGINEERING OF LUNG

(71) Applicant: YALE UNIVERSITY, New Haven, CT (US)

(72) Inventors: Elizabeth Calle, Danbury, CT (US); Laura E. Niklason, Greenwich, CT (US); Thomas Petersen, Setauket, NY (US); Liqiong Gui, Irvine, CA (US)

(73) Assignee: Yale University, New Haven, CT (US)

( * ) Notice: Subject to any disclaimer, the term of this patent is extended or adjusted under 35 U.S.C. 154(b) by 949 days.

(21) Appl. No.: 16/229,795

(22) Filed: Dec. 21, 2018

(65) Prior Publication Data

US 2019/0201453 A1 Jul. 4, 2019

Related U.S. Application Data

(60) Division of application No. 14/625,080, filed on Feb. 18, 2015, now Pat. No. 10,188,683, which is a continuation of application No. 13/146,605, filed as application No. PCT/US2010/023213 on Feb. 4, 2010, now abandoned.

(60) Provisional application No. 61/206,799, filed on Feb. 4, 2009.

(51) Int. Cl.
*A61K 35/42* (2015.01)
*C12N 5/071* (2010.01)

(52) U.S. Cl.
CPC ............ *A61K 35/42* (2013.01); *C12N 5/0688* (2013.01); *C12N 2533/90* (2013.01)

(58) Field of Classification Search
None
See application file for complete search history.

(56) References Cited

U.S. PATENT DOCUMENTS

| | | | |
|---|---|---|---|
| 5,240,846 A | 8/1993 | Collins et al. | |
| 5,336,616 A | 8/1994 | Livesey et al. | |
| 5,625,128 A | 4/1997 | Wilson et al. | |
| 6,962,814 B2 | 11/2005 | Mitchell et al. | |
| 2003/0118567 A1 | 6/2003 | Stewart et al. | |
| 2003/0180268 A1 | 9/2003 | Atala et al. | |
| 2007/0059293 A1 | 3/2007 | Atala et al. | |
| 2007/0244568 A1 | 10/2007 | Matsuda et al. | |
| 2008/0112890 A1 | 5/2008 | Lelkes et al. | |
| 2008/0292595 A1 | 11/2008 | Arbetman et al. | |
| 2008/0292677 A1 | 11/2008 | Cortiella et al. | |

FOREIGN PATENT DOCUMENTS

| | | |
|---|---|---|
| CA | 2618731 A1 | 3/2007 |
| EP | 564786 A2 | 10/1993 |
| EP | 1698356 A1 | 9/2006 |
| JP | H06261933 A | 9/1994 |
| JP | 2016013123 A | 1/2016 |
| WO | 0214480 A2 | 2/2002 |
| WO | 2005063314 A1 | 7/2005 |
| WO | 2005113748 A4 | 4/2006 |
| WO | 2007025233 A1 | 3/2007 |
| WO | 2008100555 A2 | 8/2008 |
| WO | 2008144820 A1 | 12/2008 |
| WO | 2010091188 A1 | 8/2010 |
| WO | 2011002926 A2 | 1/2011 |

OTHER PUBLICATIONS

Petersen, Thomas H. In Vitro Development of Engineered Lung Tissue. Doctoral Dissertation, Duke University. 2009. 283 Pages.*
Canadian Examination Report for Canadian Patent Application No. 2,751,133 dated Nov. 15, 2016.
Hypertonic. See http://merriam-webster.com/dictionary/hypertonic, downloaded on May 2, 2016.
PCT International Search Report and Written Opinion for PCT/US2010/023213 dated May 24, 2010.
Perfusion. See http://merriam-webster.com/dictionary/perfusion, downloaded on May 2, 2016.
Alexander, et al., Function and mode of regulation of endothelial major histocompatibility complex class II, Cell Transplant 18, 2009, 255-259.
Conconi, et al., Tracheal matrices, obtained by a detergent-enzymatic method, support in vitro the adhesion of chondrocytes and tracheal epithelial cells, Transpl Int 18 ,2005 ,727-734.
Ferdous, et al., Utility and control of proteoglycans in tissue engineering, Tissue Engineering 13 ,2007 ,1893-1904.
Foronjy, et al., Transgenic expression of matrix metalloproteinase-9 causes adult-onset emphysema in mice associated with the loss of alveolar elastin, Am J Physiol Lung Cell Mol Physiol 294:L ,2008, 1149-1157.
Gilbert, et al., Decellularization of tissues and organs, Biomaterials 27(19) ,2006 ,3675-3683.
Gilbert, et al., Quantification of DNA in biologic scaffold materials, J Surg Res 152(1) ,2008 ,135-139.
Macchiarini, et al., Clinical transplantation of a tissue-engineered airway, Lancet 372(9655) ,2008 ,2023-2030.
Mondrinos, et al., Engineering three-dimensional pulmonary tissue constructs, Tissue Engineering 12(4) ,2006 ,717-728.
Nichols, et al., Engineering of a complex organ: progress toward developmetn of a tissue-engineered lung, Proc Am Thorac Soc. 5(6), 2008, 723-730.
Niemeier, et al., The isolated perfused lung, Environ Health Perspect. 56 ,Jun. 1984 ,35-41.
Ott, et al., Perfusion-decellularized matrix: using nature's platform to engineer a bioartificial heart, Nat Med 14 ,2008 ,213-221.
Petersen, et al., Tissue-engineered lungs for in vivo implantation, Science 329(5991) ,Jul. 30, 2010 ,538-541.
Vandenbroucke, et al., Regulation of endothelial junctional permeability, Ann N Y Acad Sci 1123 ,2008 ,134-145.

(Continued)

*Primary Examiner* — James D Schultz
*Assistant Examiner* — Kimberly A Aron
(74) *Attorney, Agent, or Firm* — Saul Ewing LLP; Kathryn Doyle

(57) ABSTRACT

The present invention relates to compositions comprising a decellularized tissue. The present invention also provides an engineered three dimensional lung tissue exhibiting characteristics of a natural lung tissue. The engineered tissue is useful for the study of lung developmental biology and pathology as well as drug discovery.

23 Claims, 70 Drawing Sheets

(56) References Cited

OTHER PUBLICATIONS

Wiesel, et al., Cell attachment, growth characteristics and surface morphology of human upper-respiratory tract epithelium cultured on extracellular matrix, Eur J Clin Invest. 13(1) ,1983 ,57-63.
Canadian Office Action, dated Jul. 19, 2021, issued by the Canadian Patent Office for Canadian Application No. 3,084,176.

* cited by examiner

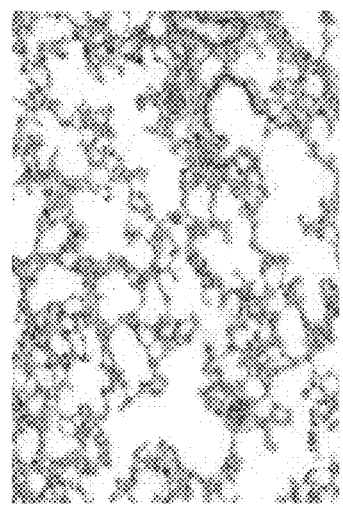
Figure 1A Native lung
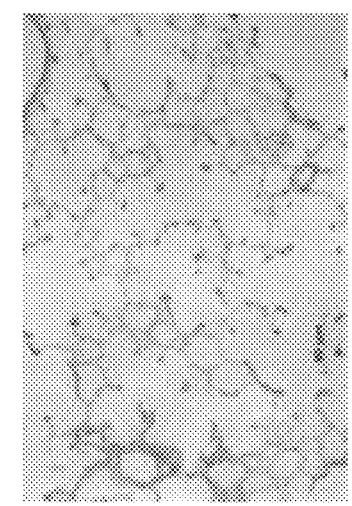
Figure 1B Decellularized lung
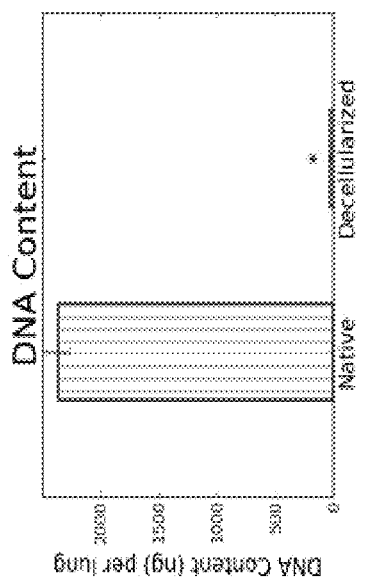
Figure 1C DNA Content

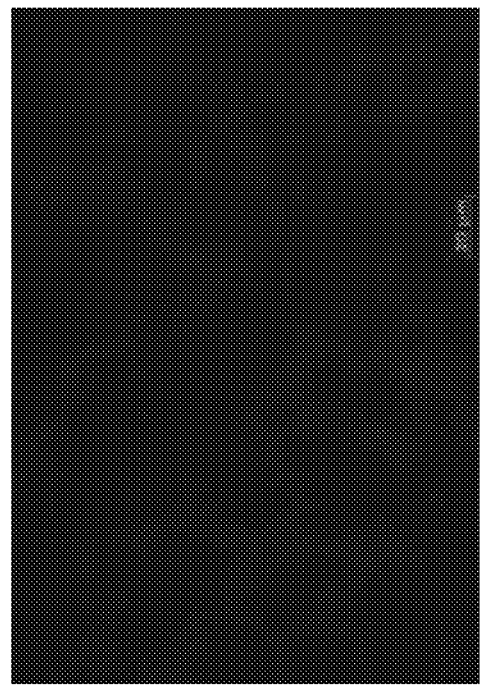
Figure 2B Decellularized lung
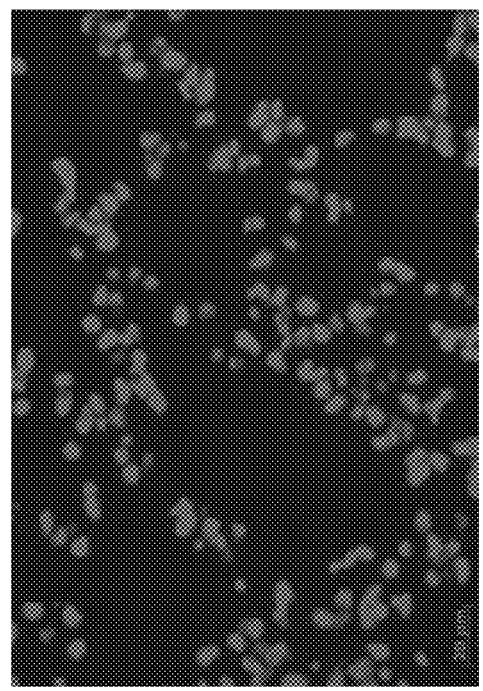
Figure 2A Native lung

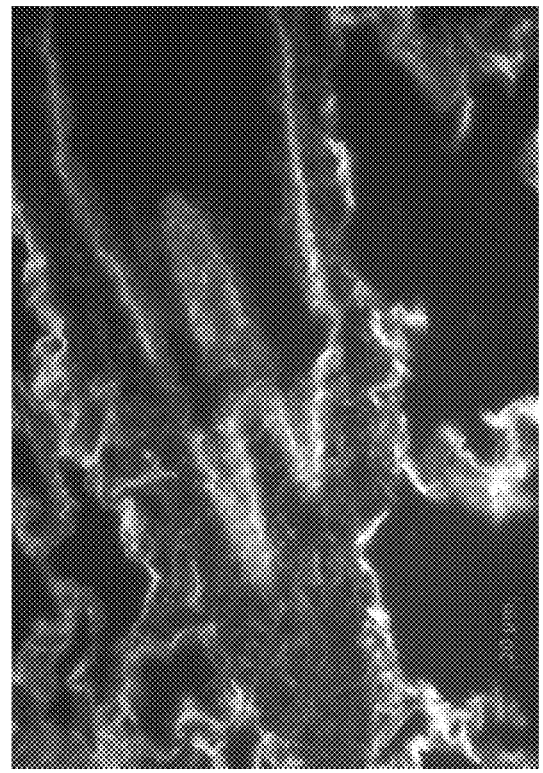
Figure 4B Decellularized lung
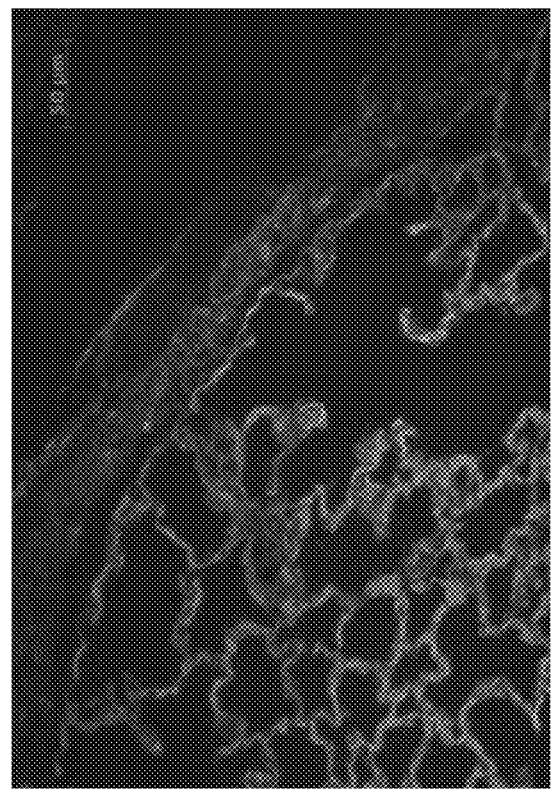
Figure 4A Native lung

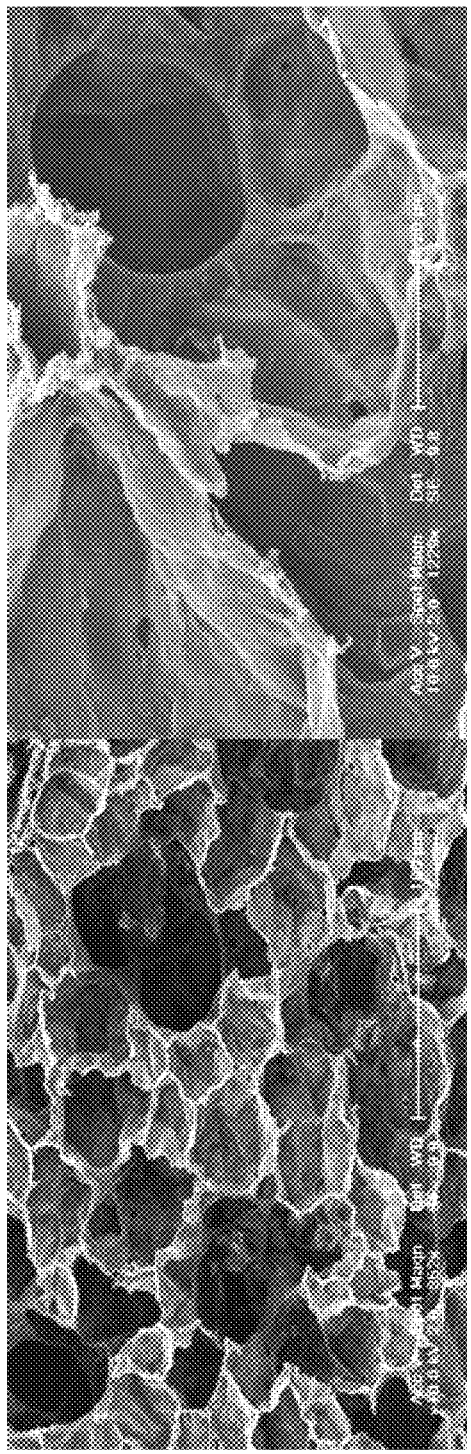
Figure 5A Native lung
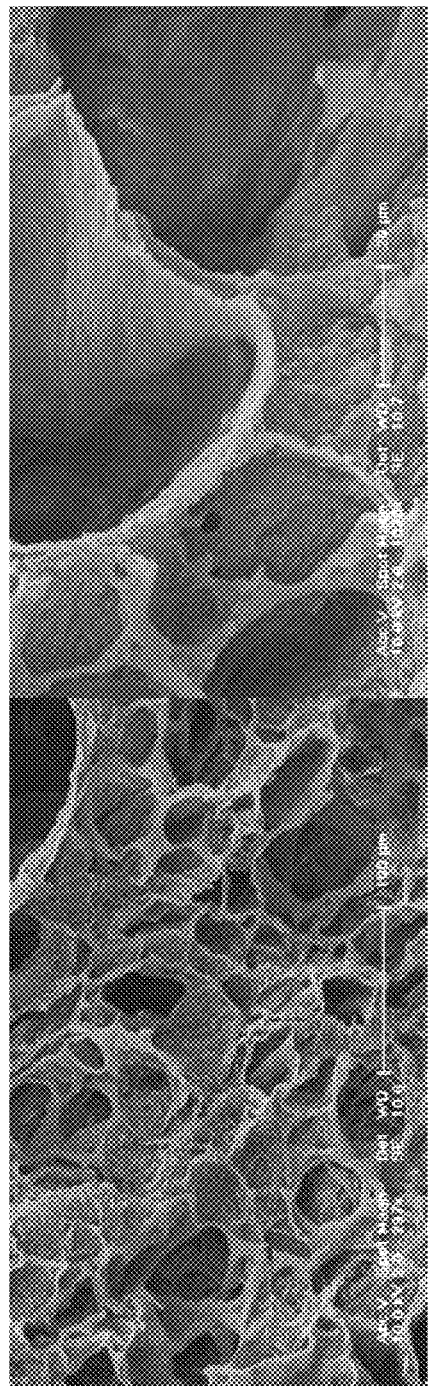
Figure 5B Decellularized lung

Figure 6A Native lung
Figure 6B Damaged decellularized lung
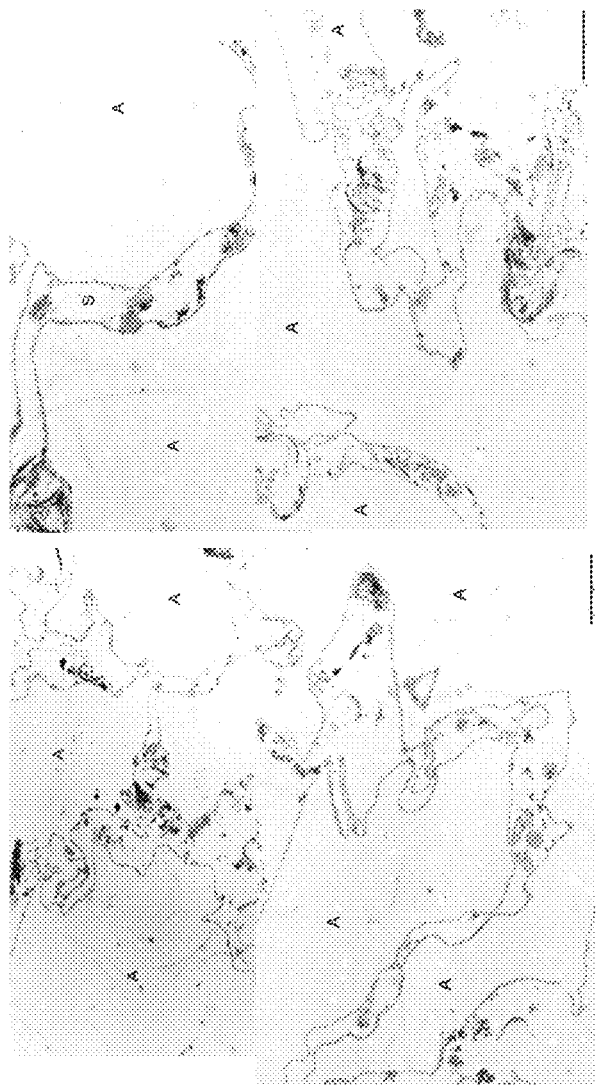
Figure 6C Decellularized lung with intact alveolar basement membrane

Figure 8

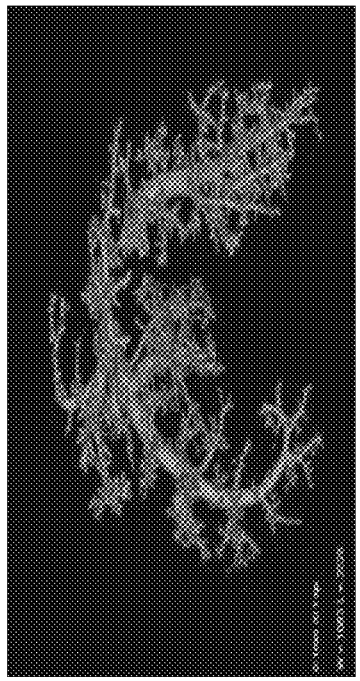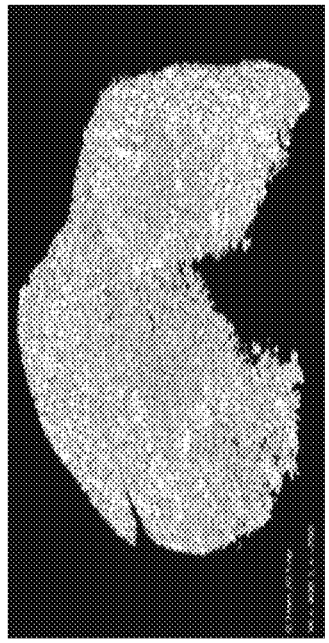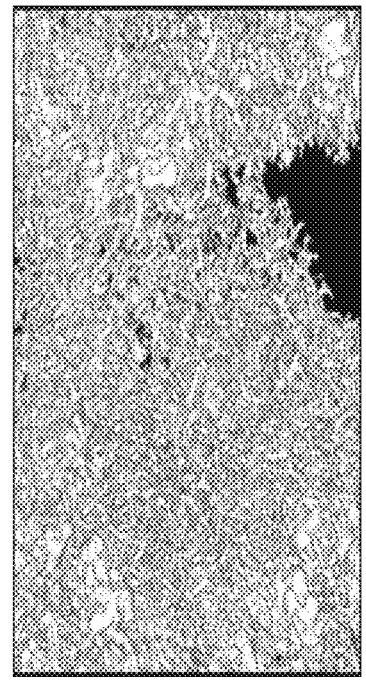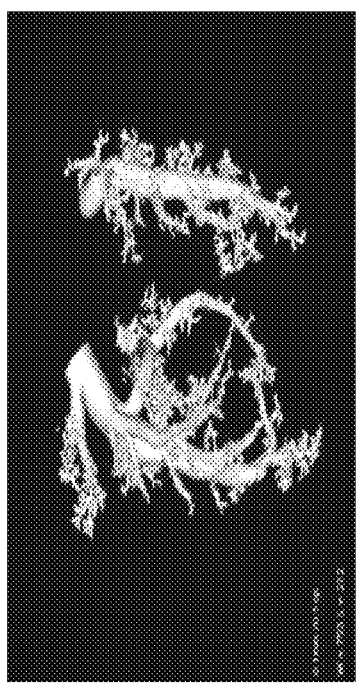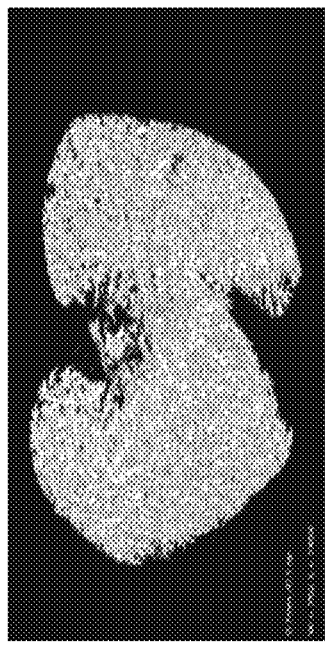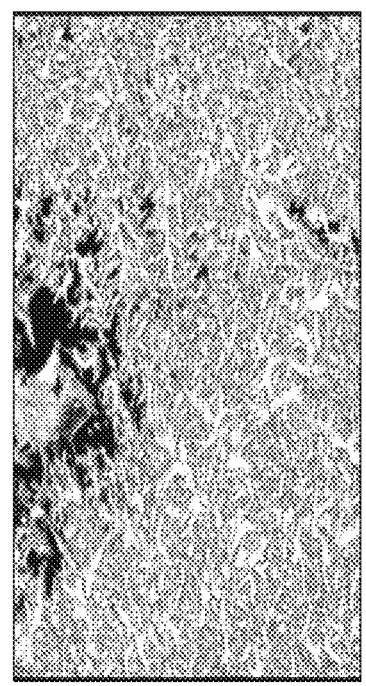
Figure 9A  Native lung
Figure 9B  Decellularized lung

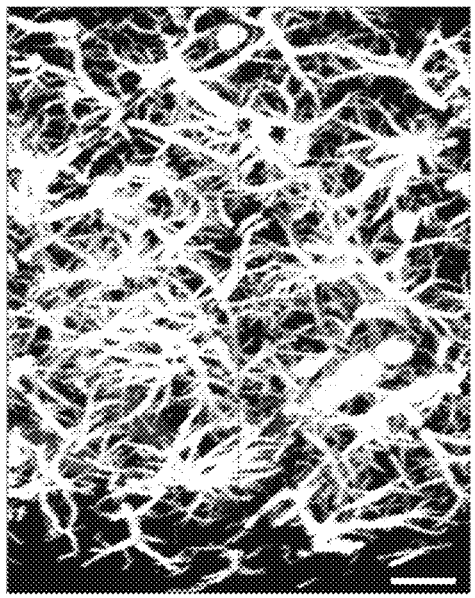
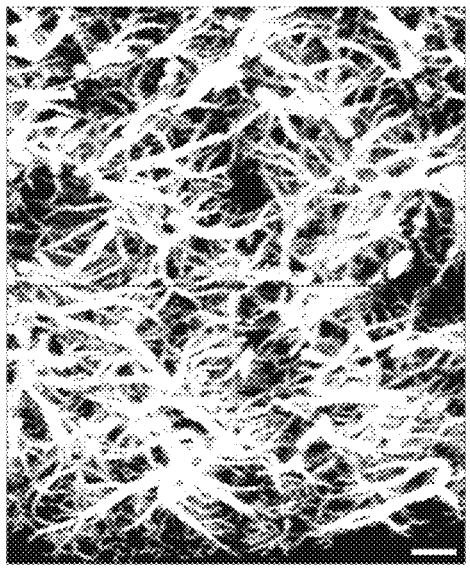
Figure 10A Native lung
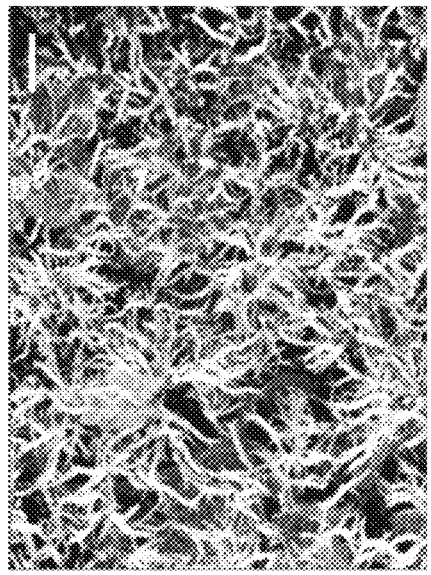
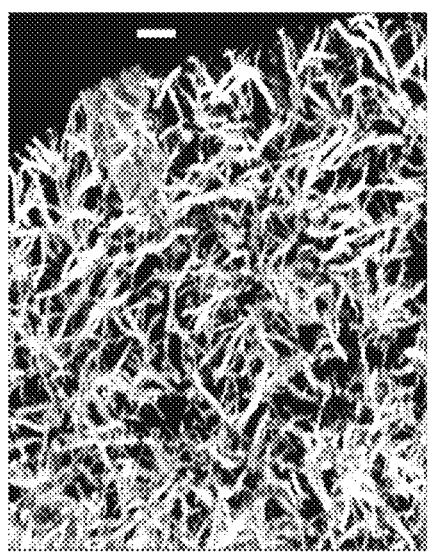
Figure 10B Decellularized lung

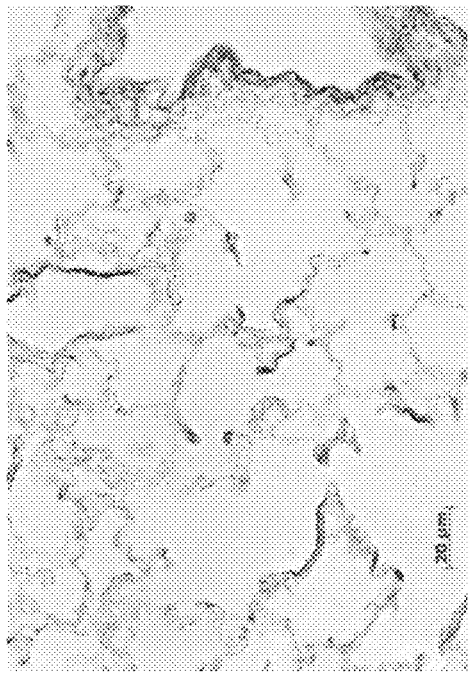
Figure 12B Decellularized lung
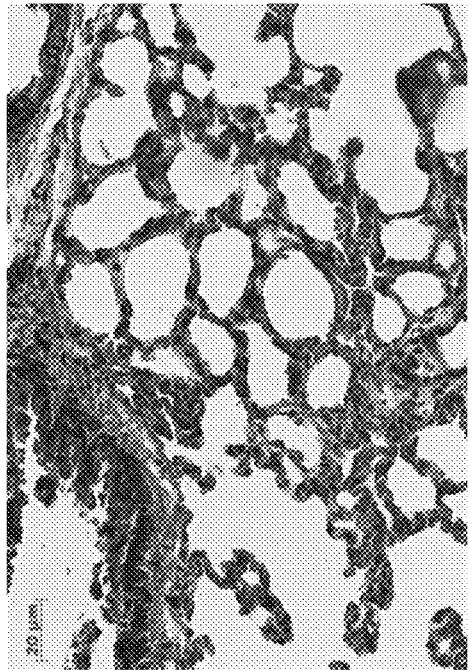
Figure 12A Native lung
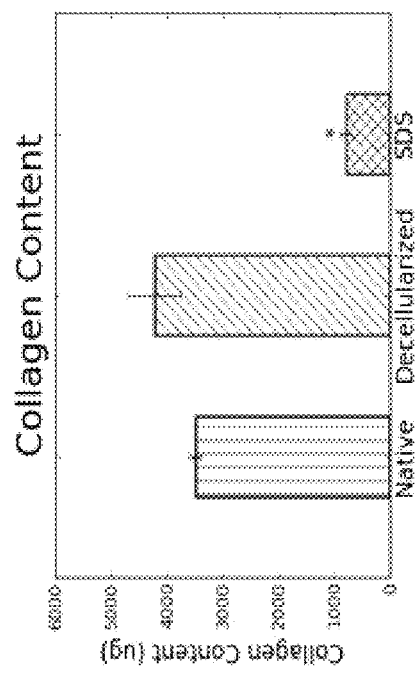
Figure 12C Collagen content

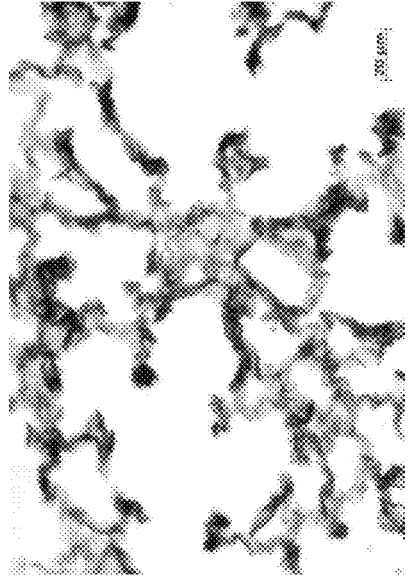
Figure 13A Native lung
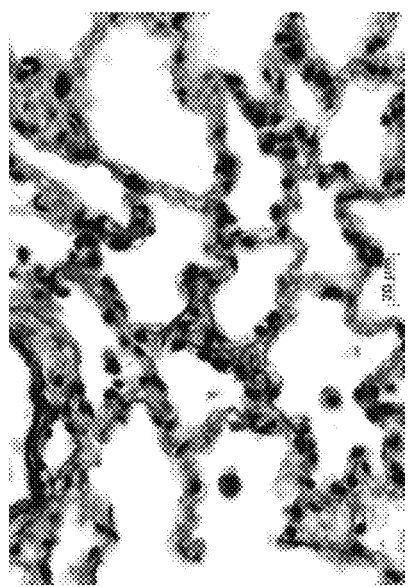
Figure 13B Decellularized lung
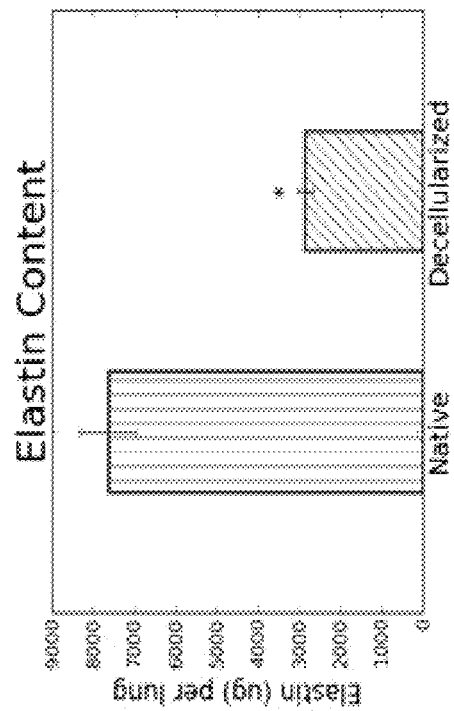
Figure 13C Elastin content

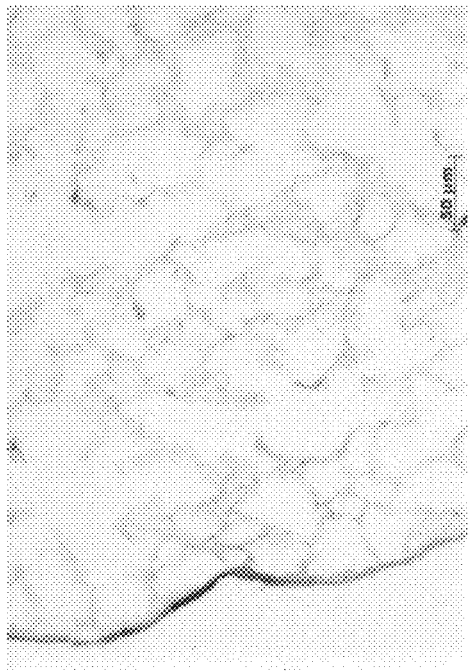
Figure 14A Native lung
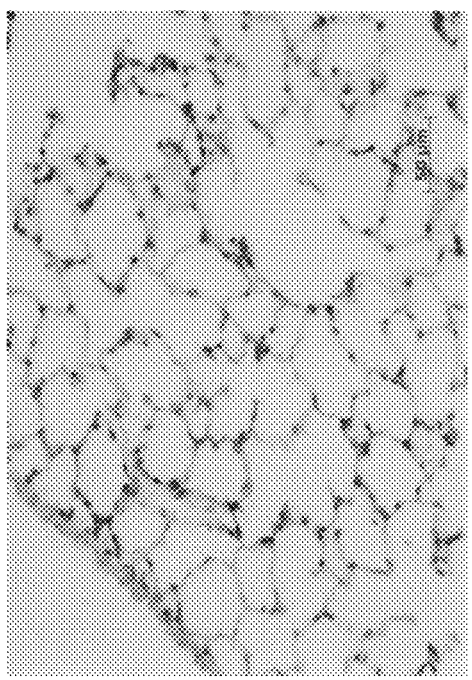
Figure 14B Decellularized lung
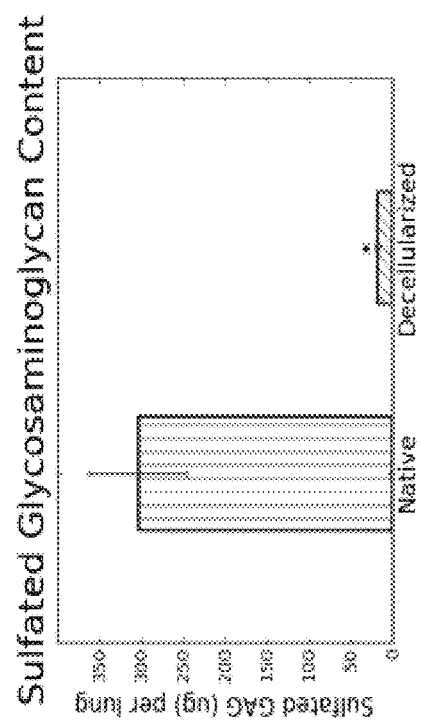
Figure 14C  GAG content

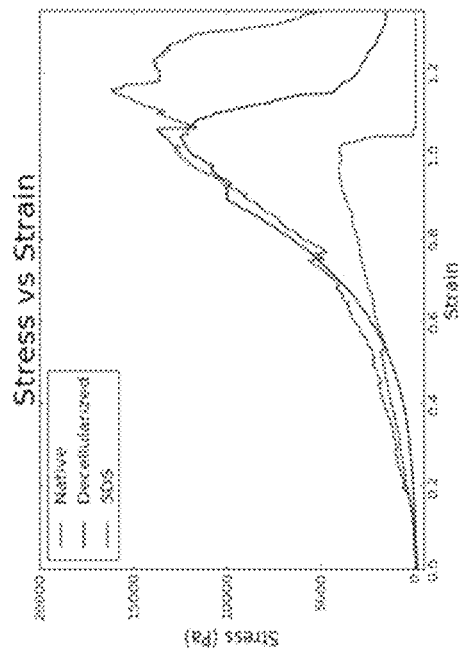
Figure 15B Stress-strain curve
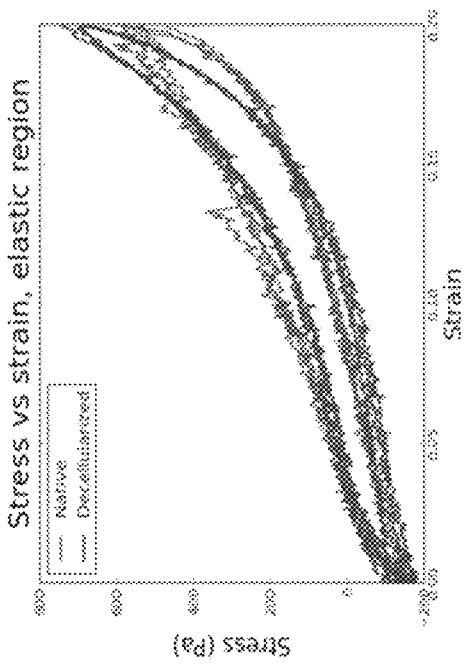
Figure 15A Stress-strain curve, elastic region

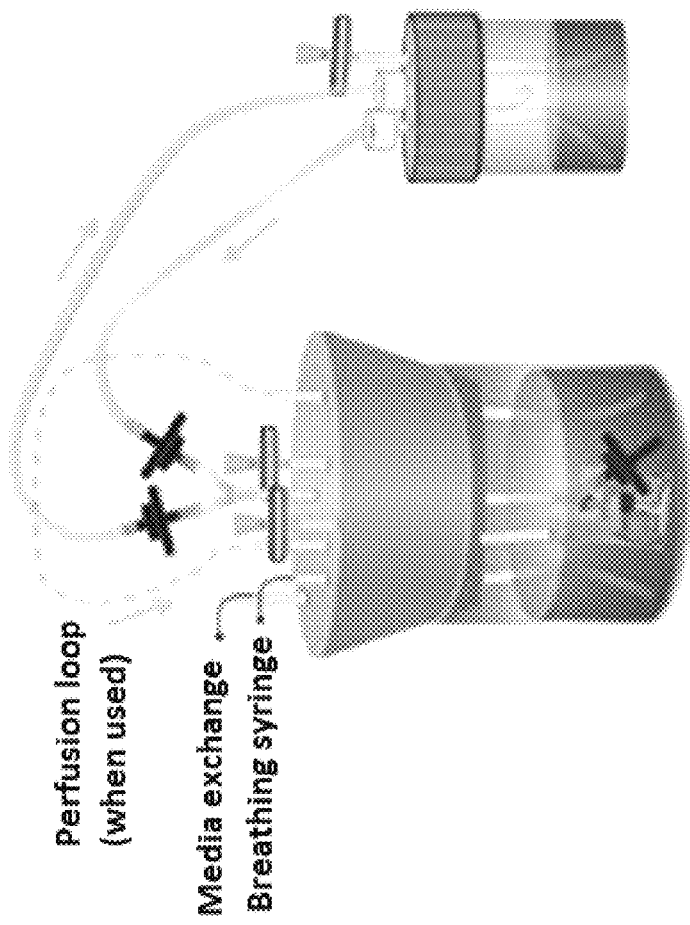
Figure 17A  Bioreactor diagram
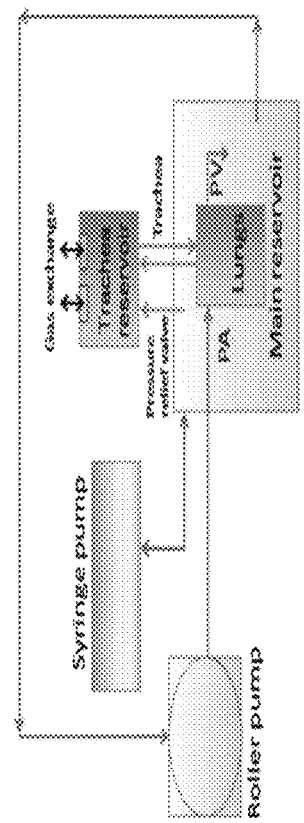
Figure 17B  Bioreactor schematic

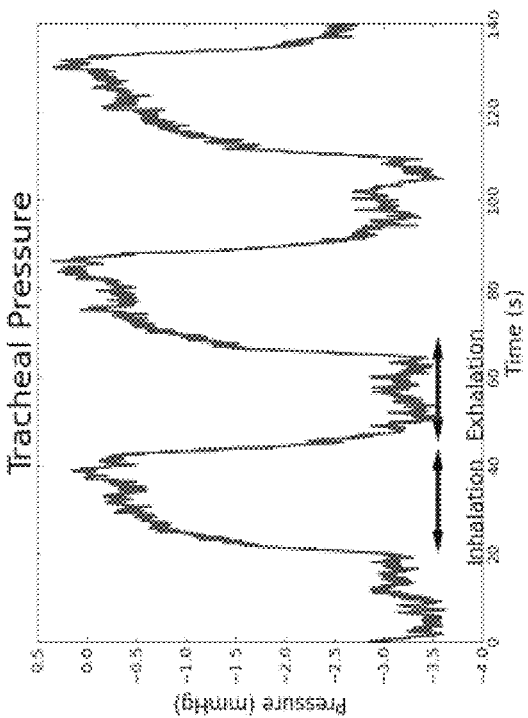
Figure 18B  Tracheal pressure
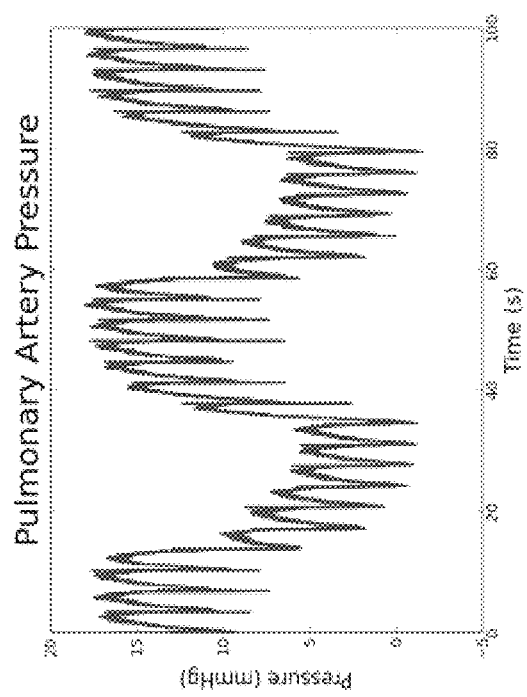
Figure 18A  Pulmonary artery pressure

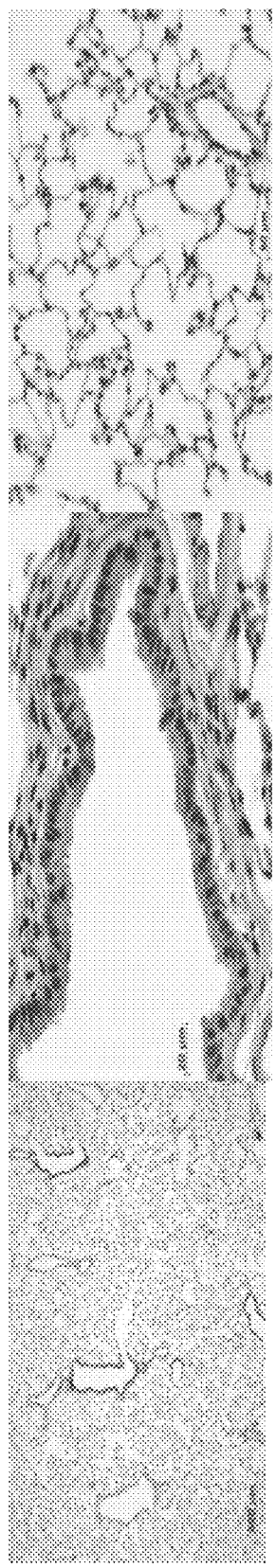
Figure 19A Native lung
Figure 19B Liquid breathing
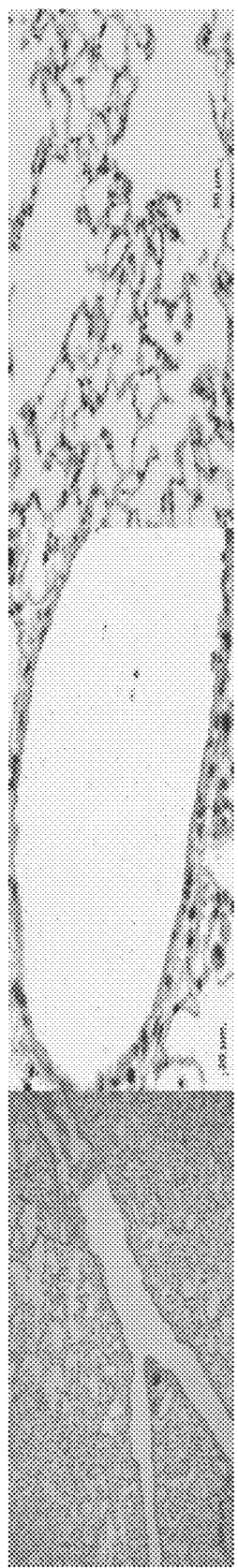
Figure 19C Air breathing

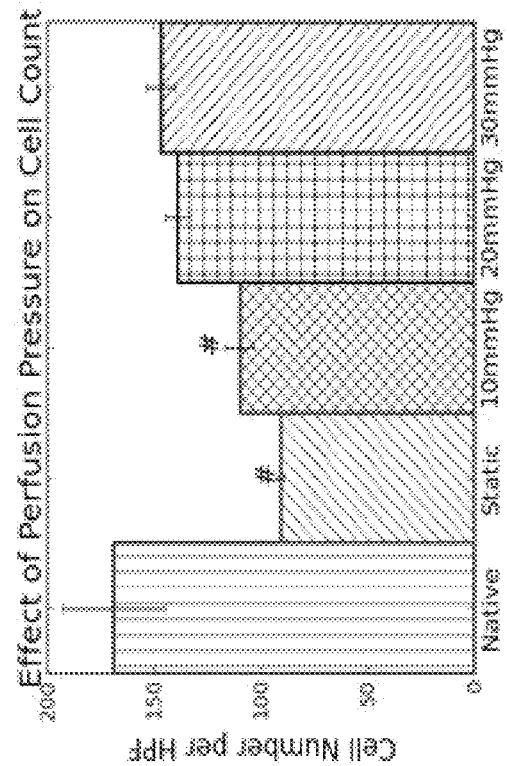
Figure 20B Perfusion effects on cell count
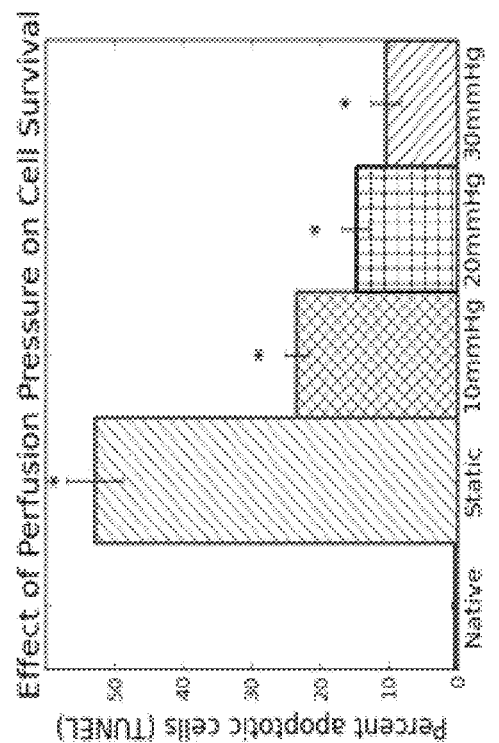
Figure 20A Perfusion effects on cell viability

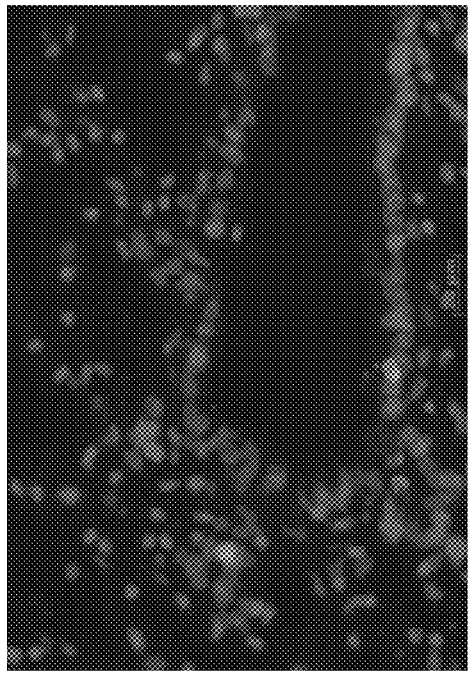
Figure 21B CCSP, Perfused lung culture
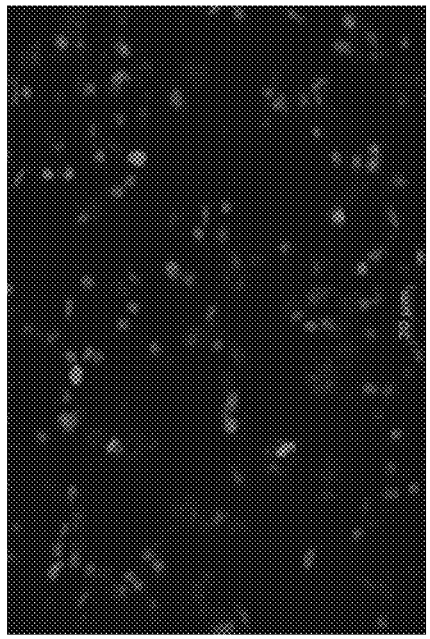
Figure 21D SPC, Perfused lung culture
Figure 21A CCSP, Native lung
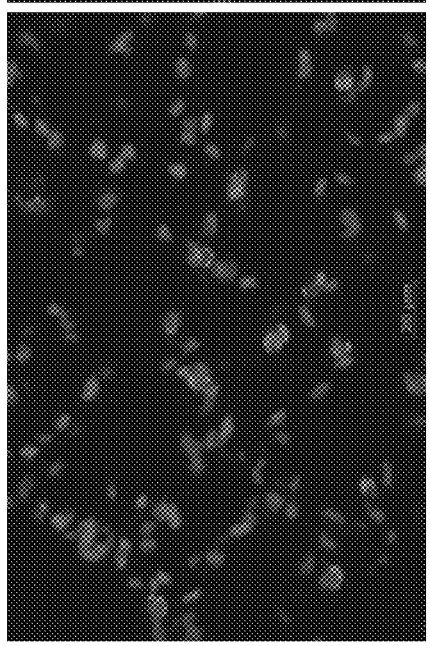
Figure 21C SPC, Native lung

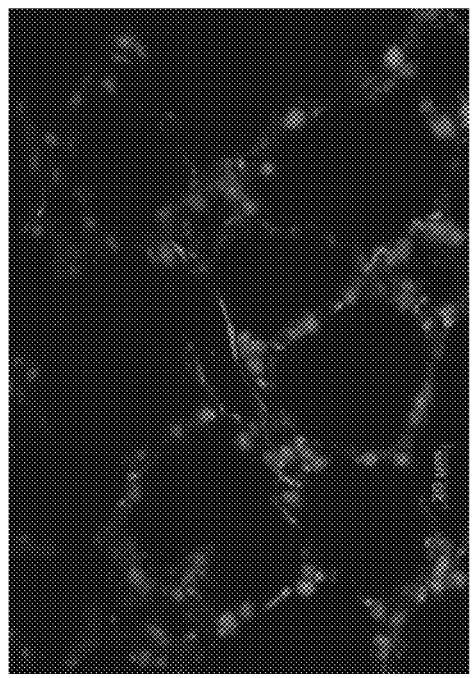
Figure 22A PECAM, Native lung
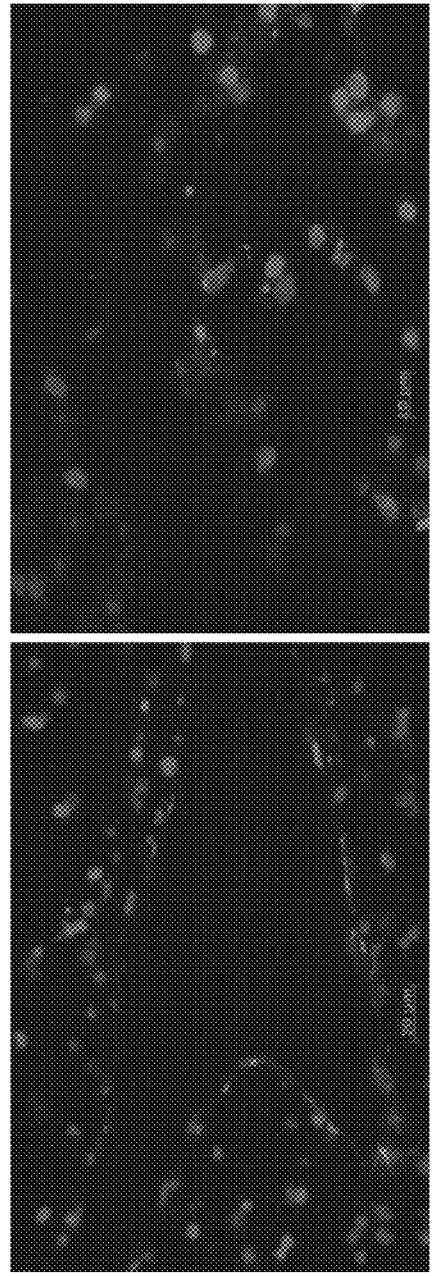
Figure 22B PECAM, Perfused lung culture

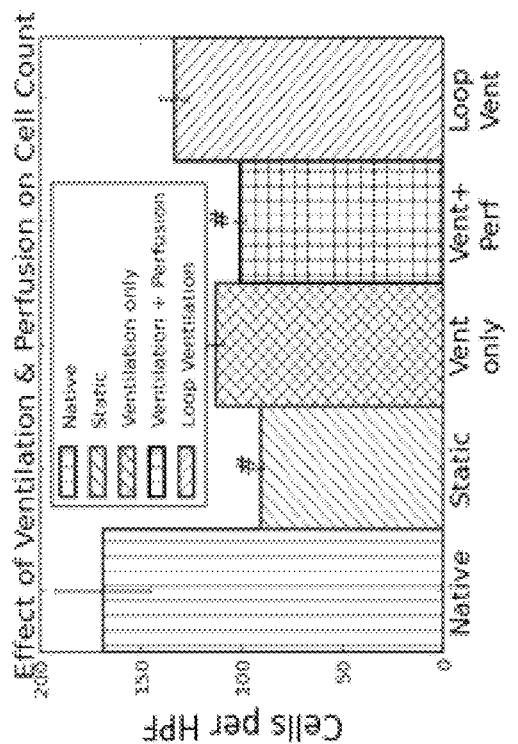
Figure 23B Ventilation effects on cell count
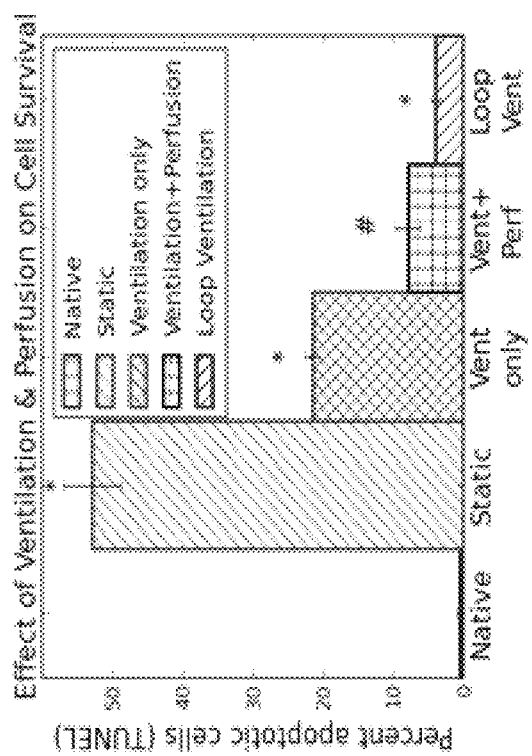
Figure 23A Ventilation effects on cell viability

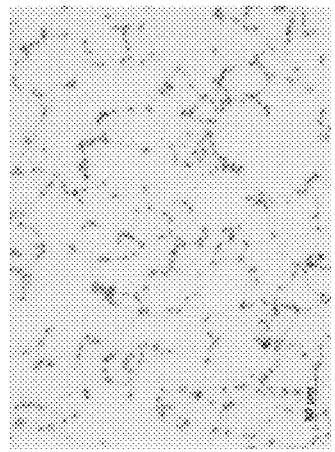
Figure 24A Native lung
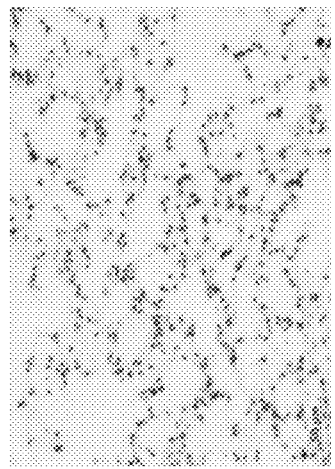
Figure 24B Single line ventilation
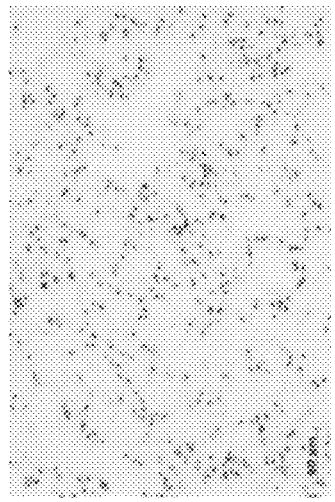
Figure 24C Dual line ('loop') ventilation

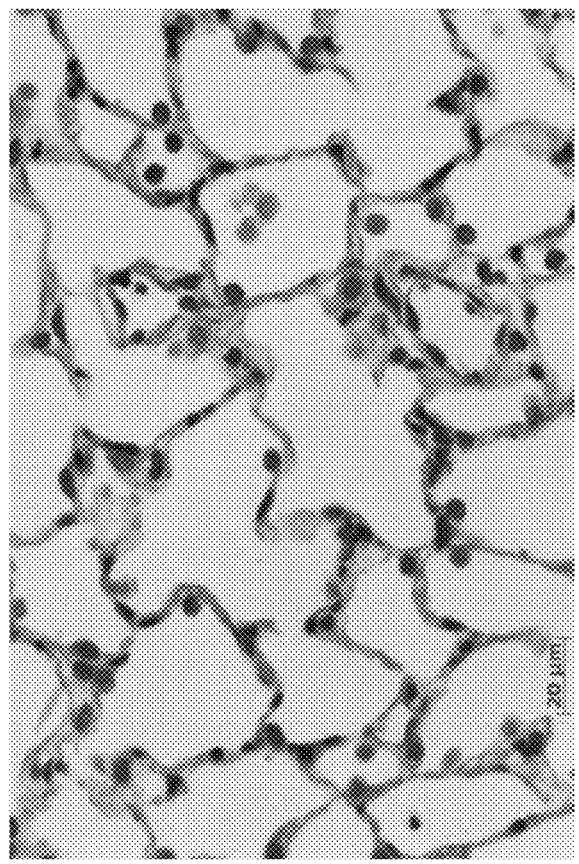
Figure 25B  Alveolar structure at 7 days
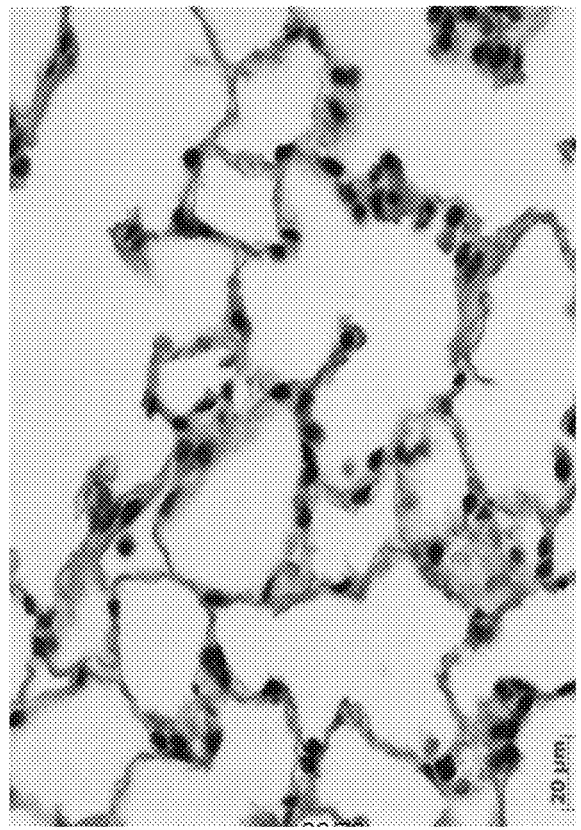
Figure 25A  Native lung

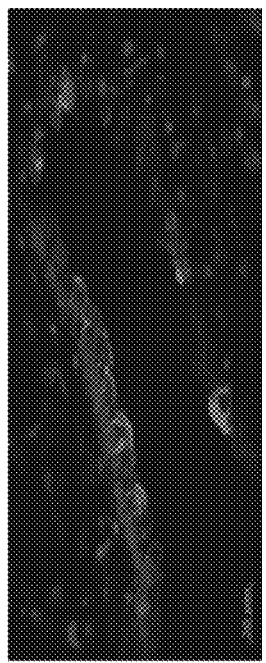
Figure 25D Cultured lung: CCSP
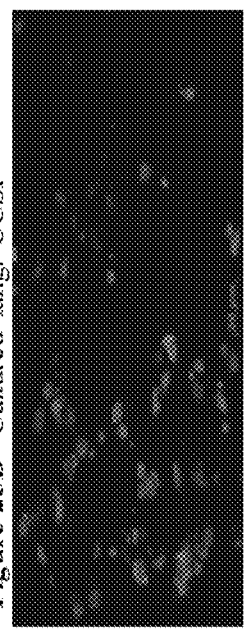
Figure 25F Cultured lung: SPC
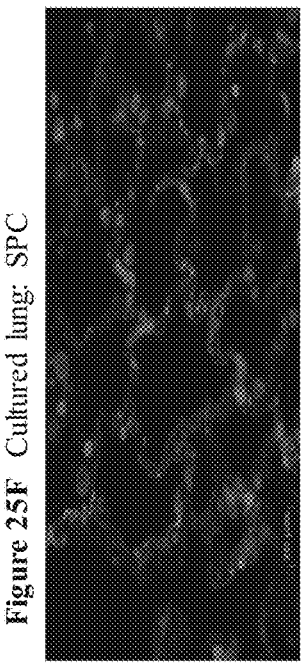
Figure 25H Cultured lung: AQP
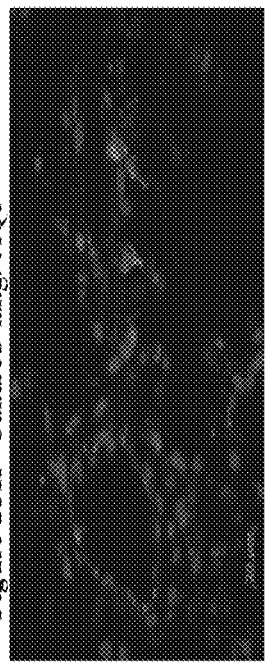
Figure 25J Cultured lung: PECAM
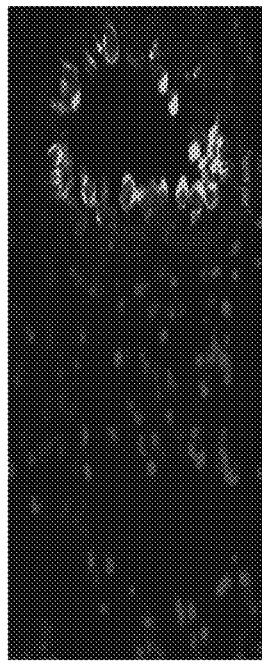
Figure 25C Native lung: CCSP
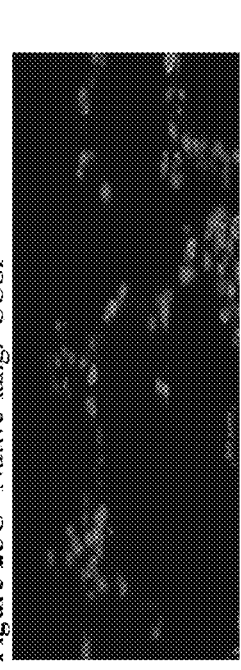
Figure 25E Native lung: SPC
Figure 25G Native lung: AQP
Figure 25I Native lung: PECAM

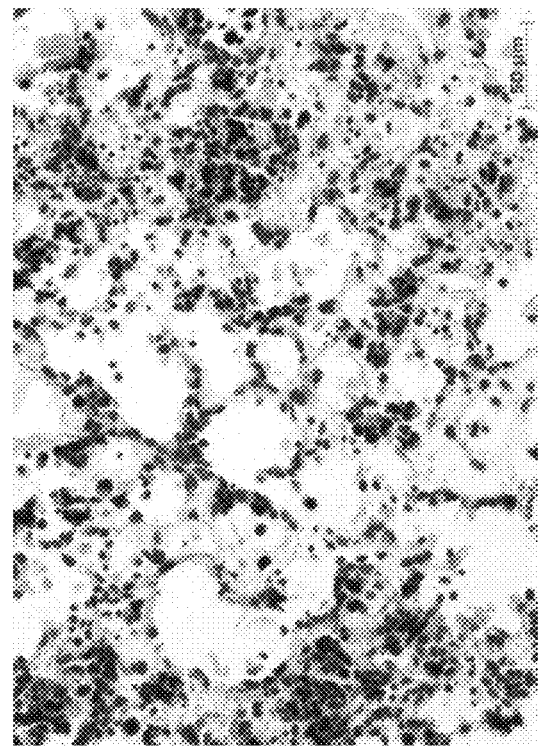
Figure 27A  3 days
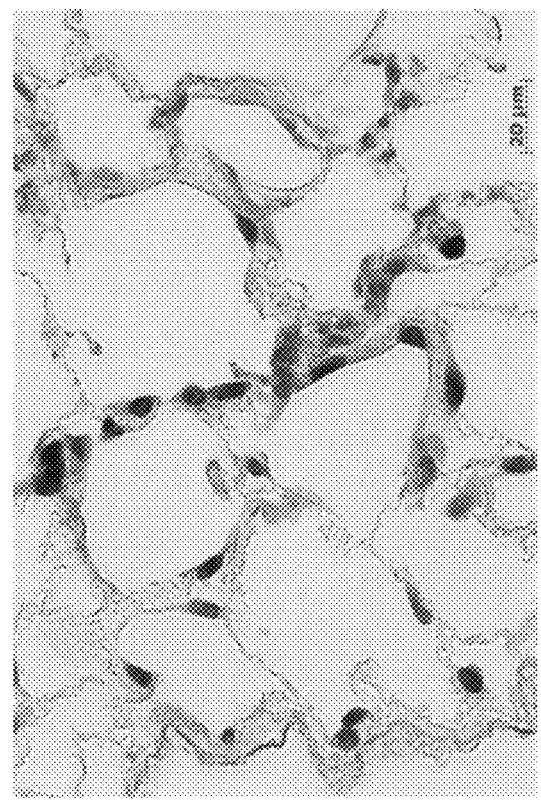
Figure 27B  7 days

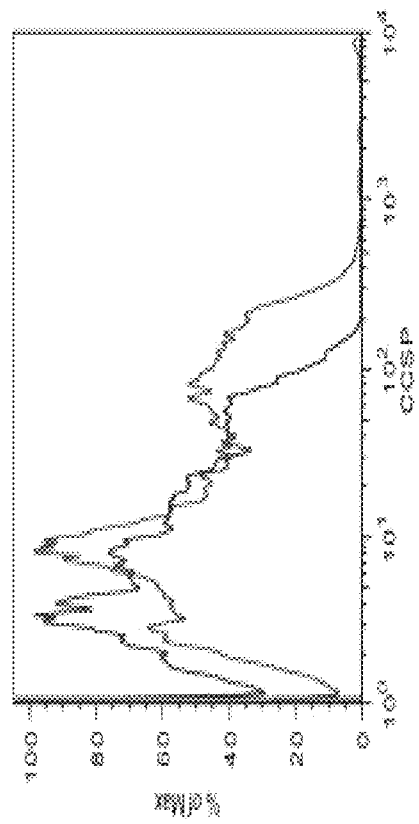
Figure 28A  Clara cell secretory protein
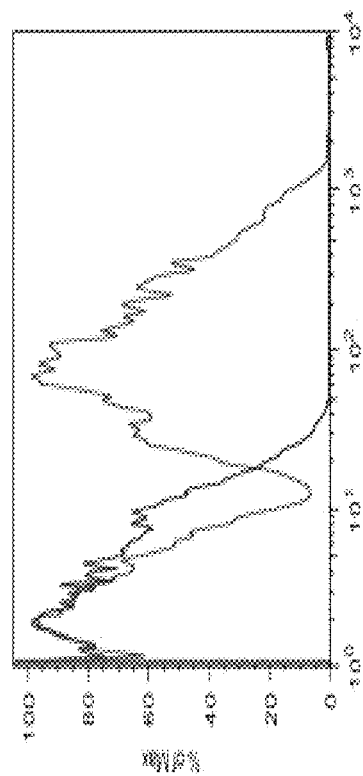
Figure 28B  Surfactant protein C

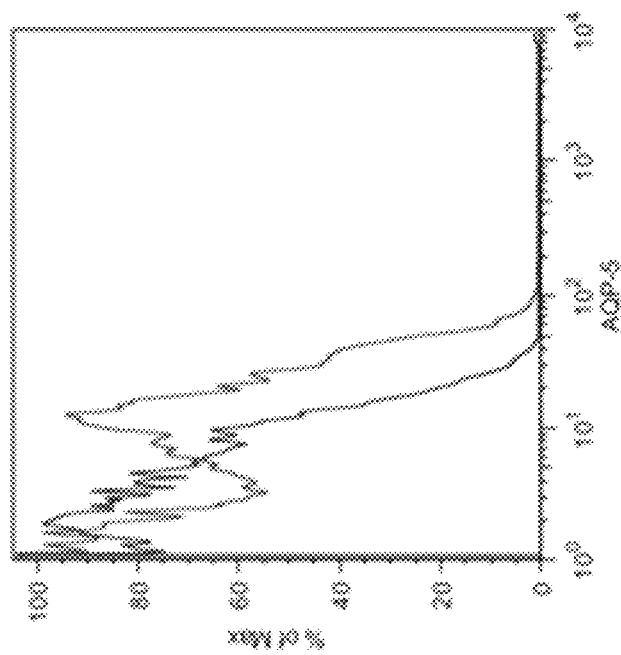
Figure 28C Aquaporin-5
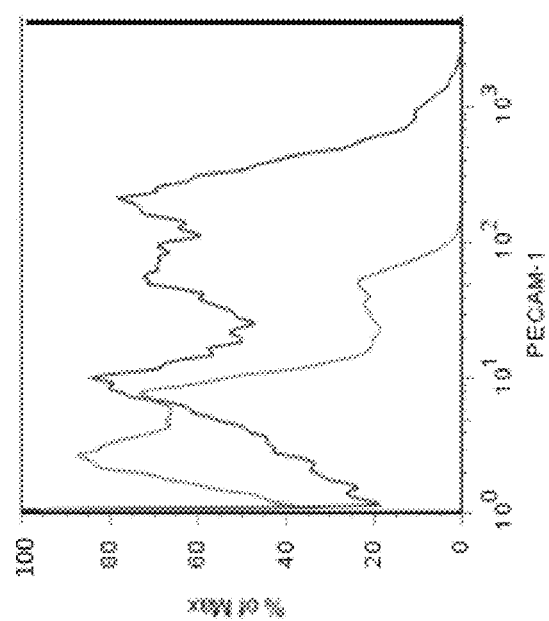
Figure 28D PECAM-1

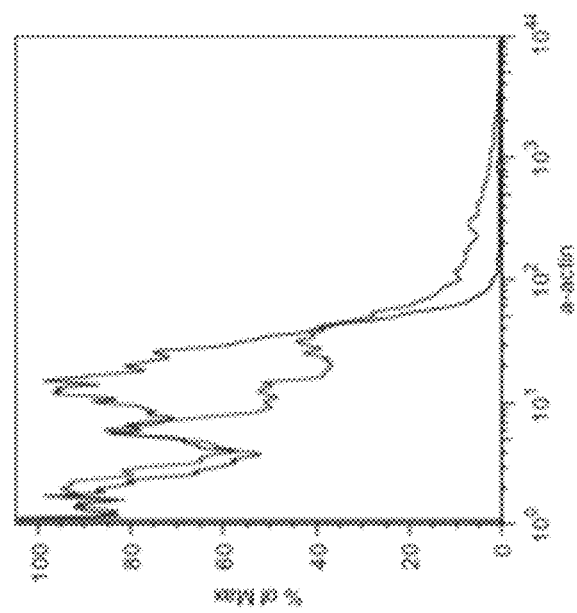
Figure 28E α-actin
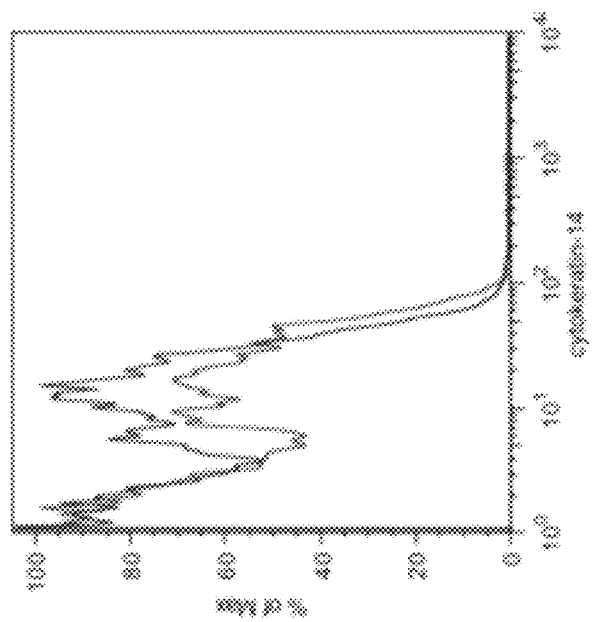
Figure 28F Cytokeratin-14

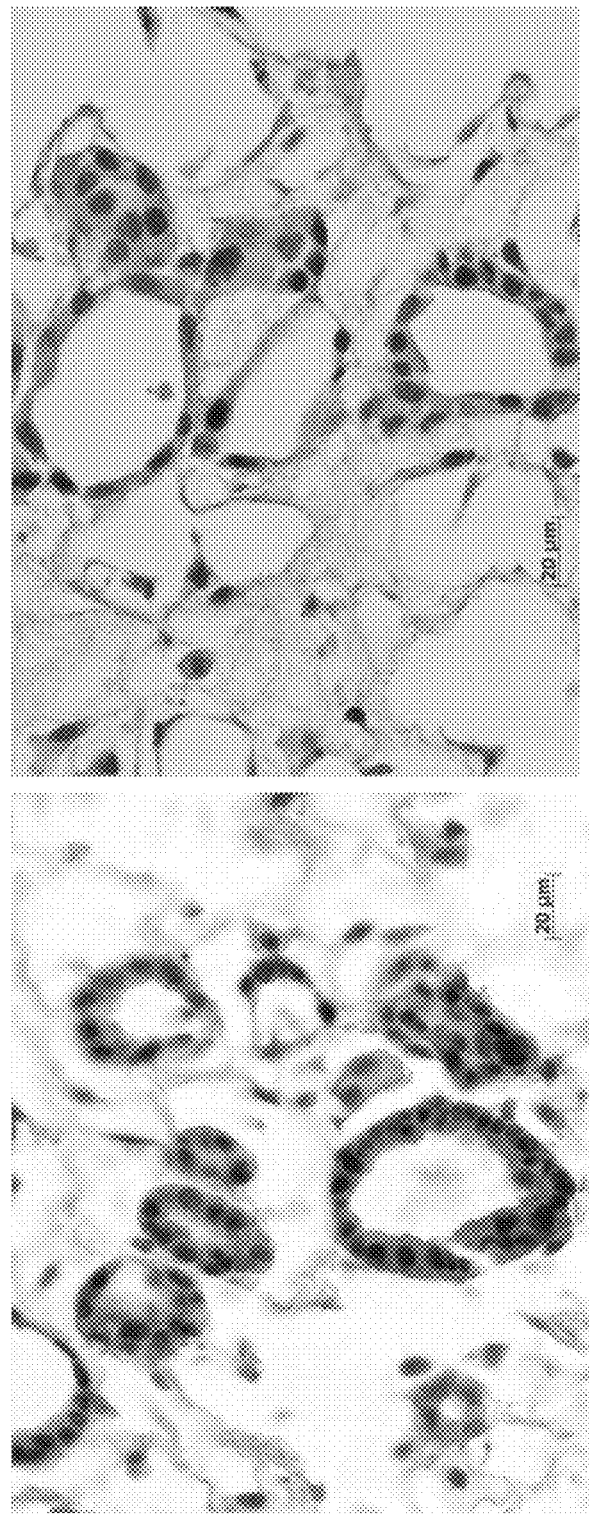
Figure 30A  PCNA stain, 4 days
Figure 30B  PCNA stain, 8 days

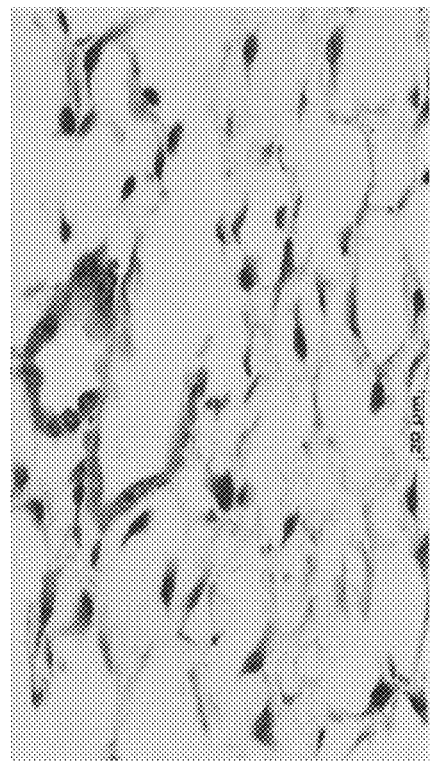
Figure 31B  TUNEL stain, 8 days
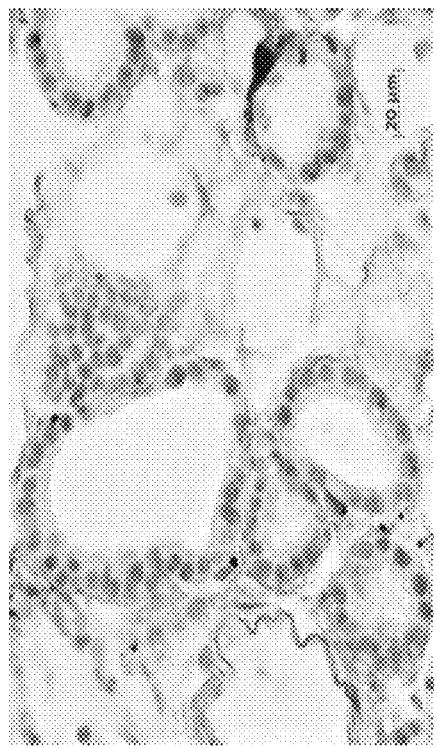
Figure 31A  TUNEL stain, 4 days

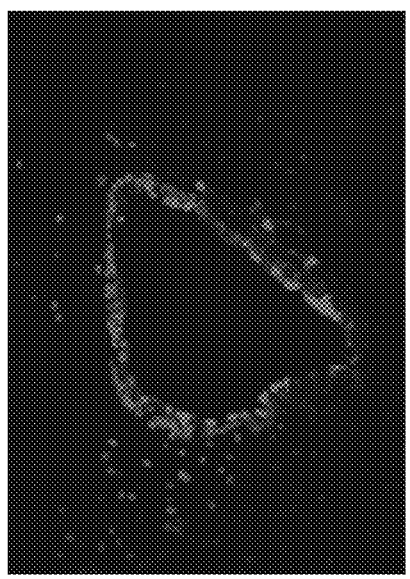
Figure 32C Engineered lung, 8 days
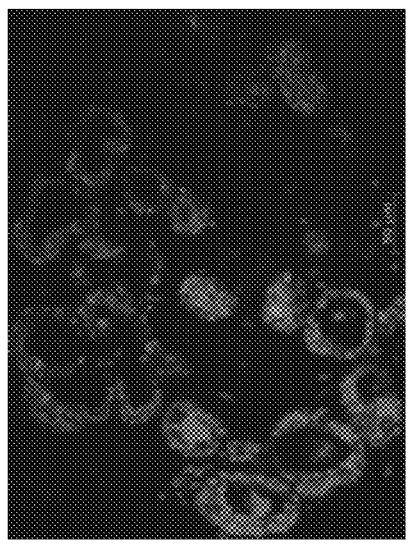
Figure 32B Engineered lung, 4 days
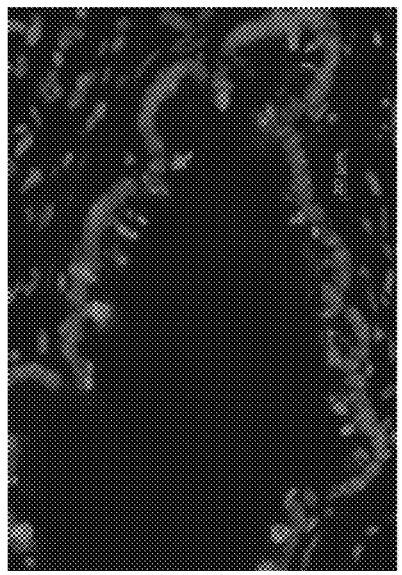
Figure 32A Native

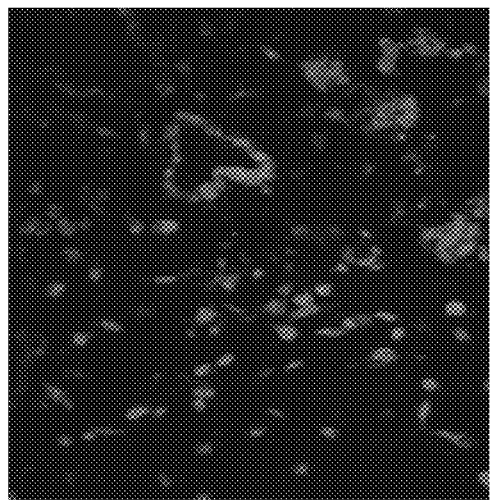
Figure 33C Engineered lung, 8 days
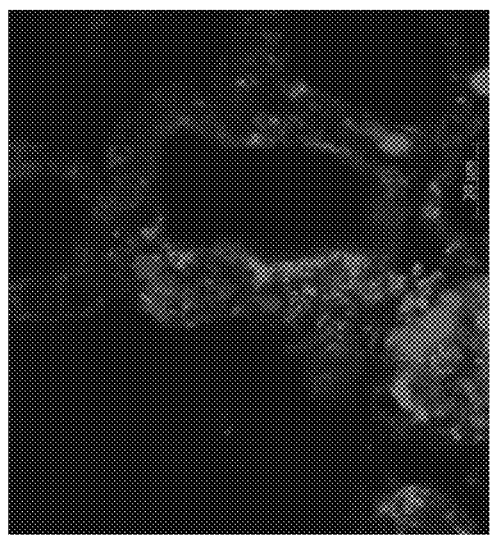
Figure 33B Engineered lung, 4 days
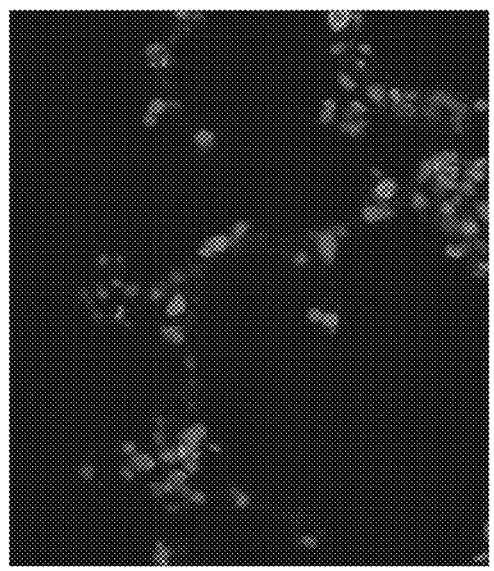
Figure 33A Native

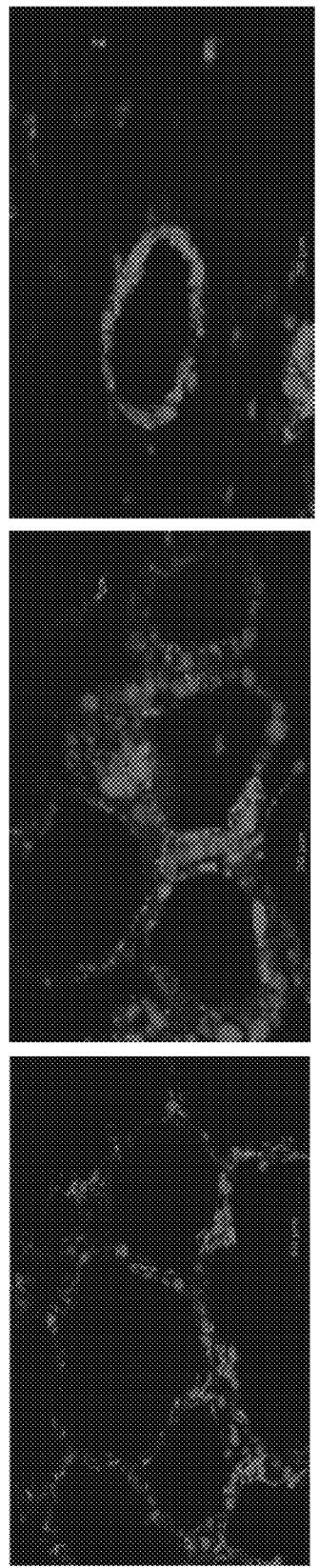
Figure 34A Native  Figure 34B Engineered lung, 4 days  Figure 34C Engineered lung, later time points

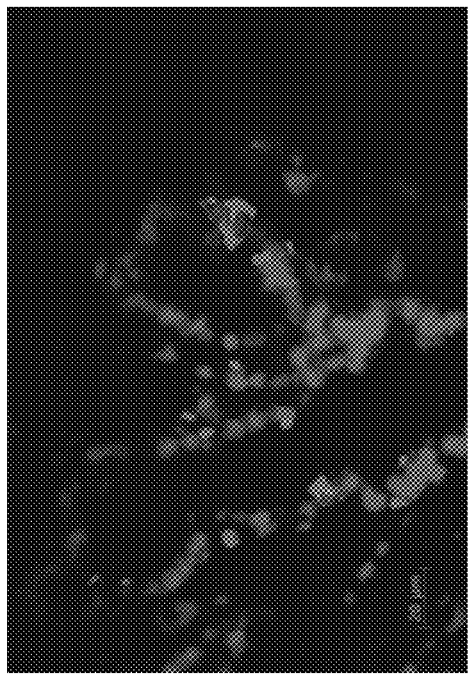
Figure 36A Native lung
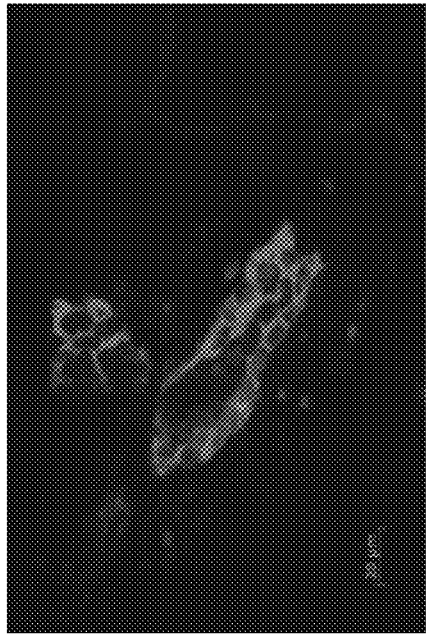
Figure 36B Engineered lung
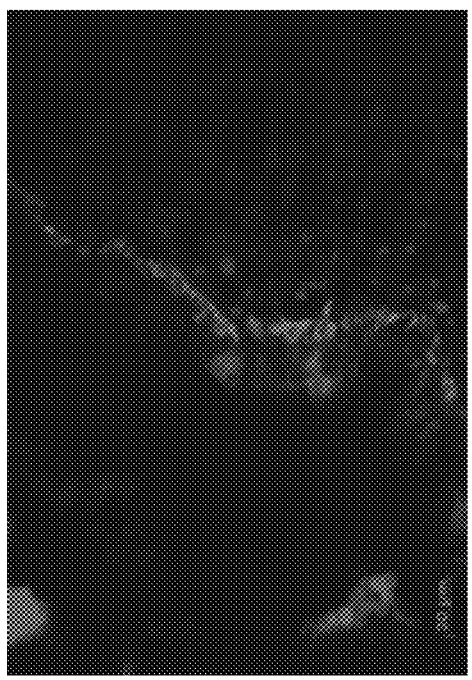
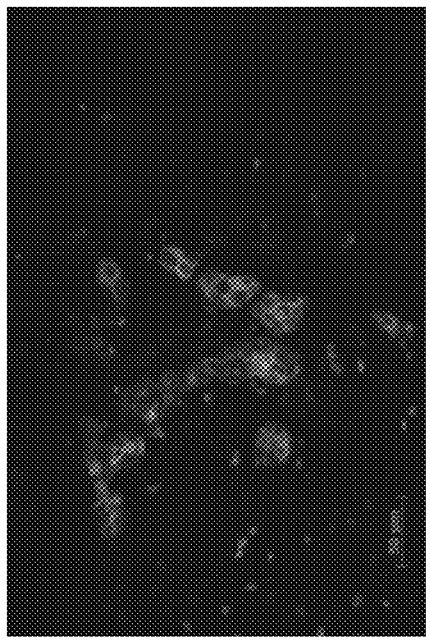
Figure 36C Engineered lung

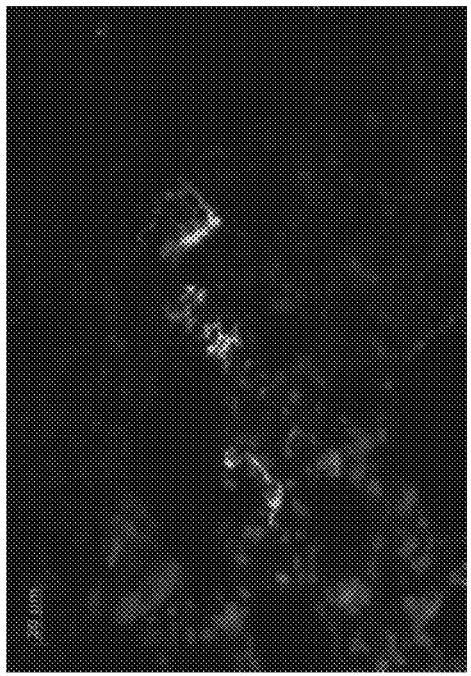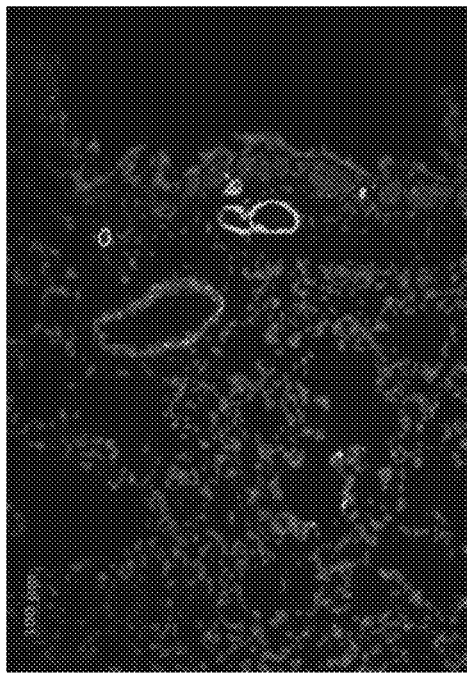
Figure 38A Native lung
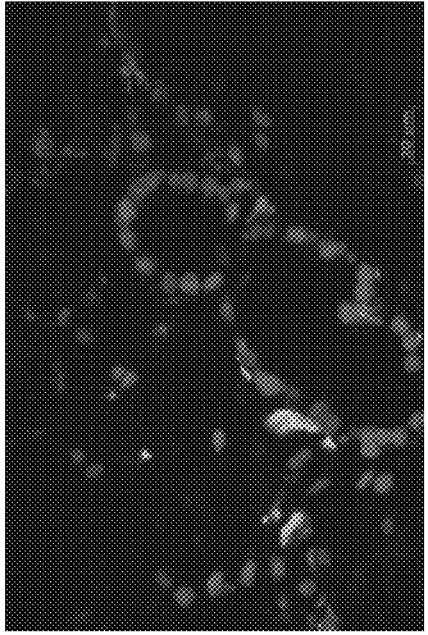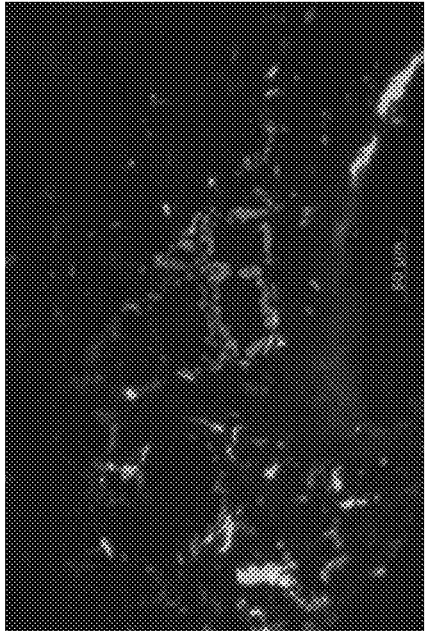
Figure 38B Engineered lung

Figure 39B    BGJb: PCNA
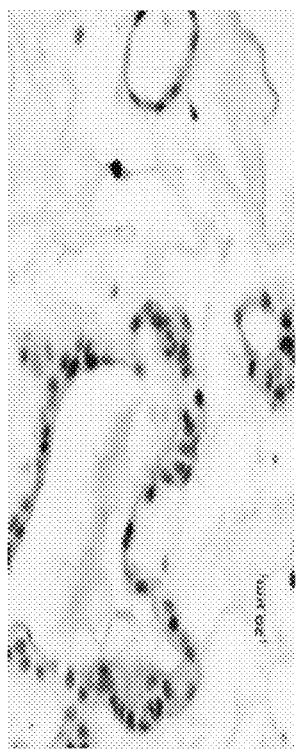
Figure 39A    DMEM+10%FBS: PCNA
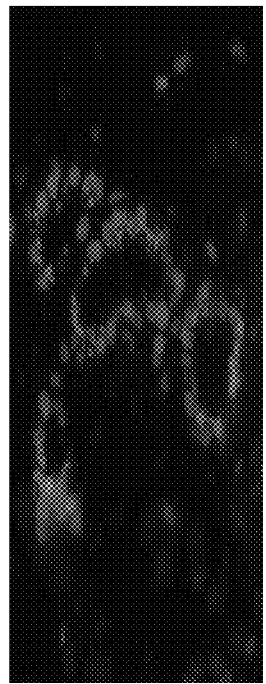
Figure 39D    BGJb: SPC
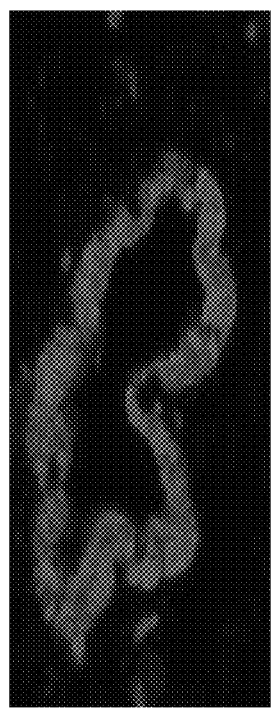
Figure 39C    DMEM+10%FBS: SPC
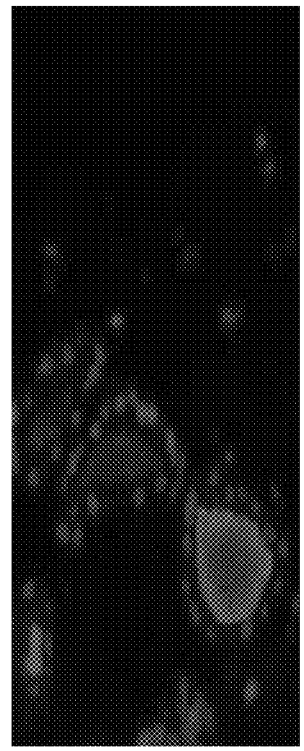
Figure 39F    BGJb: CCSP
Figure 39E    DMEM+10%FBS: CCSP

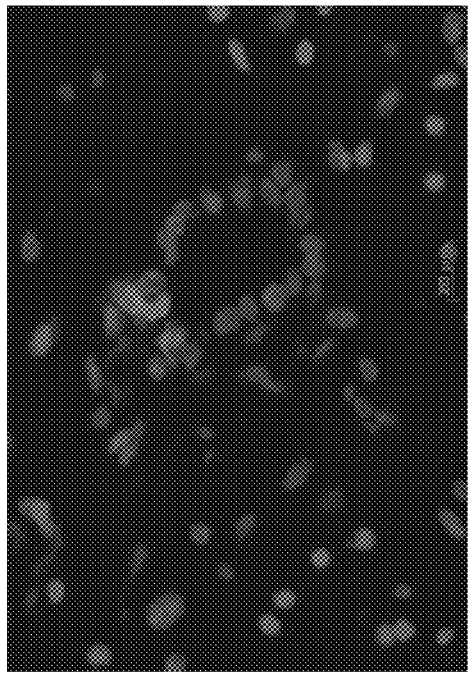
Figure 41A  Aquaporin
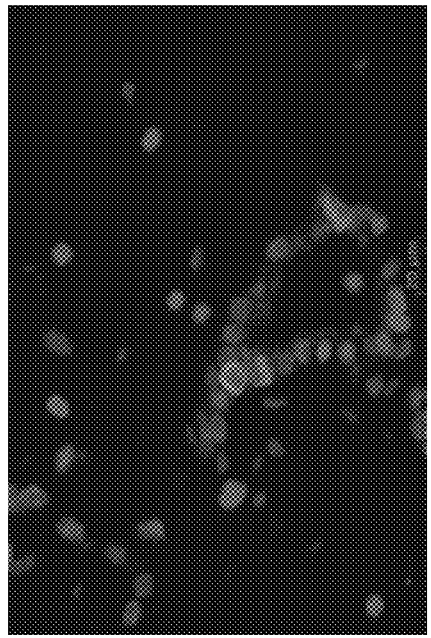
Figure 41C  CCSP
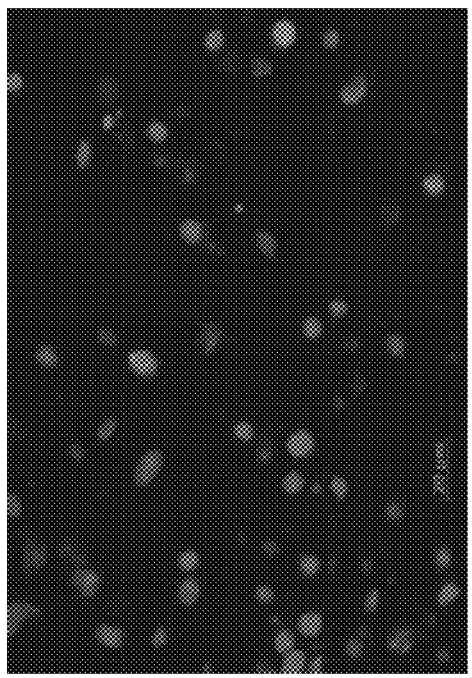
Figure 41B  SPC

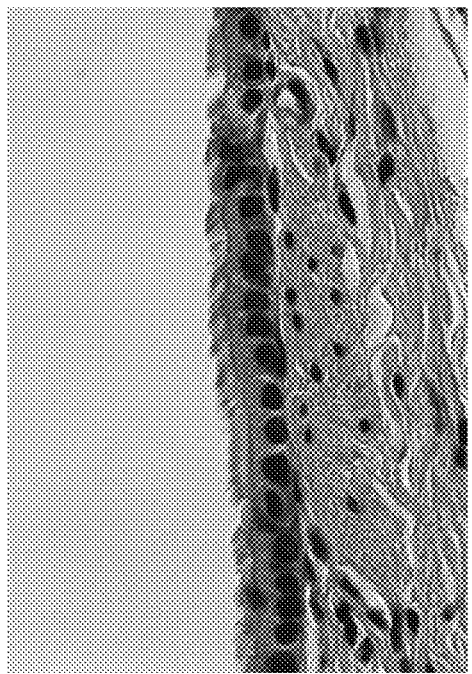
Figure 42A  Native lung
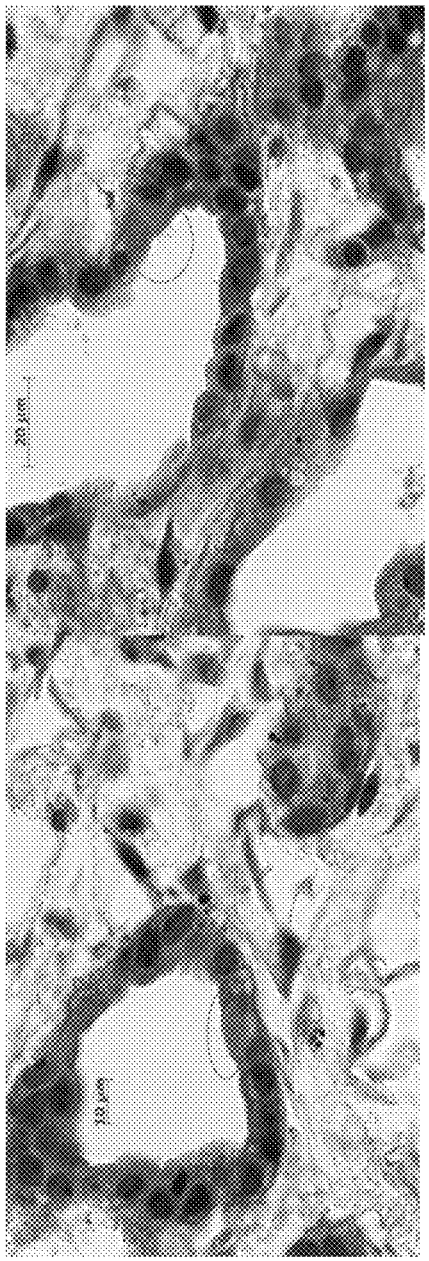
Figure 42B  Engineered lung

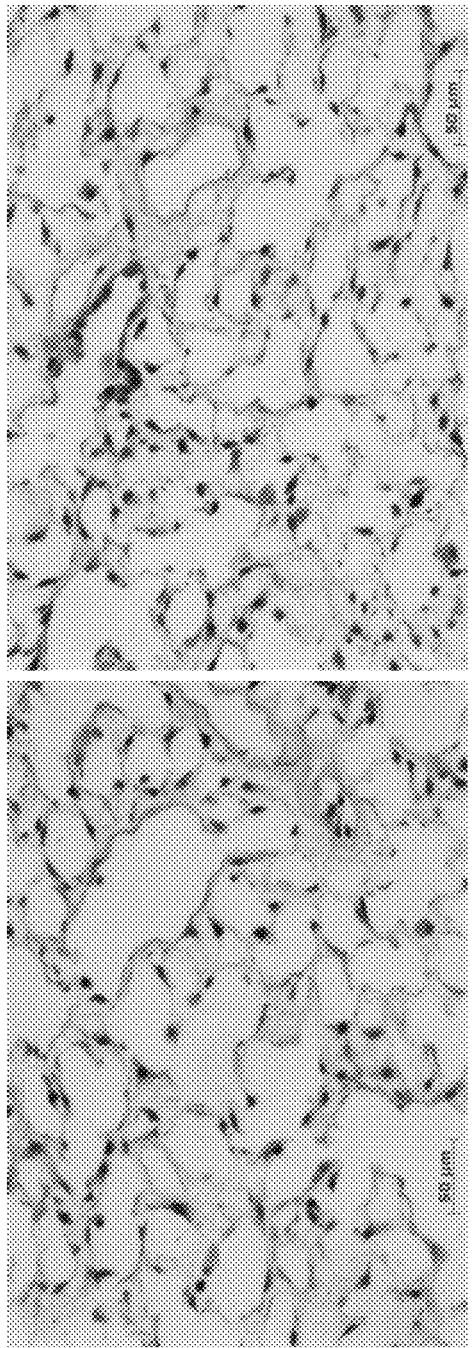
Figure 43A Ventilation
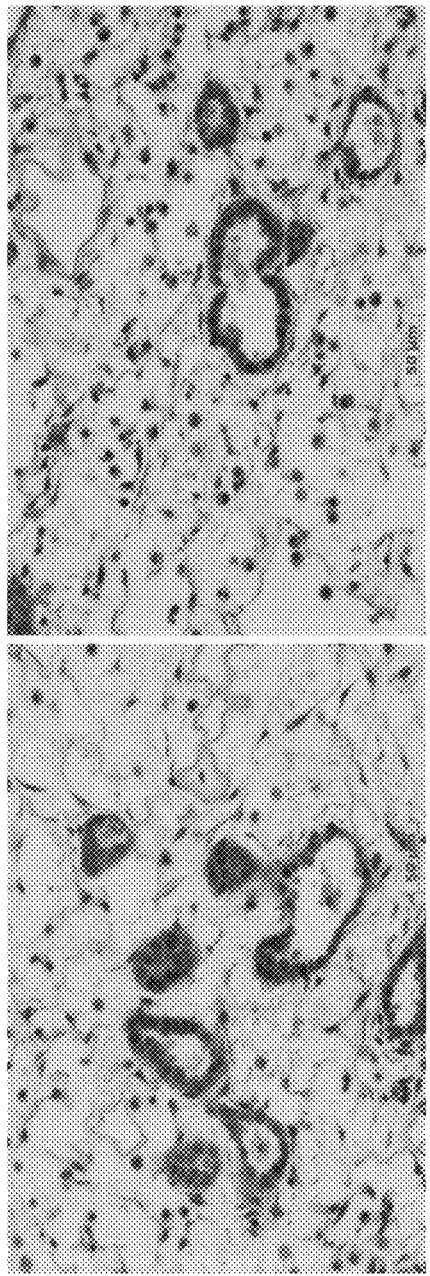
Figure 43B Perfusion

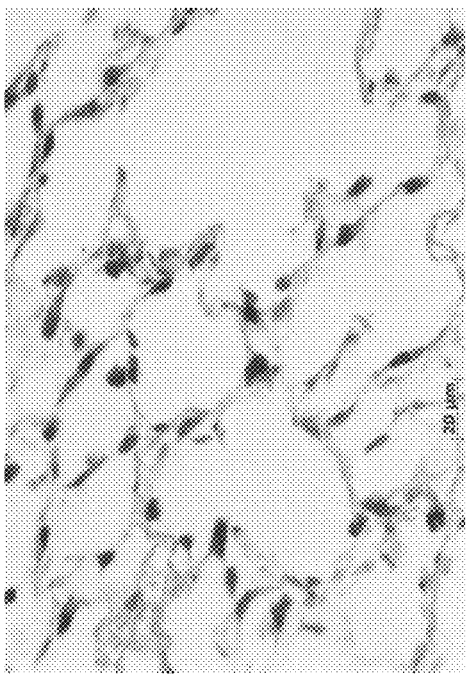
Figure 44B Ventilation: TUNEL
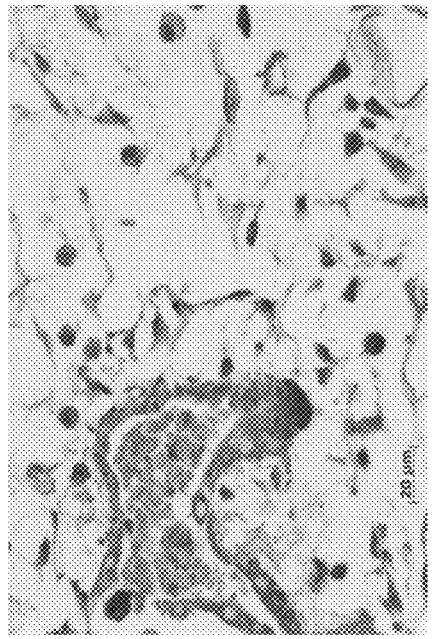
Figure 44D Perfusion: TUNEL
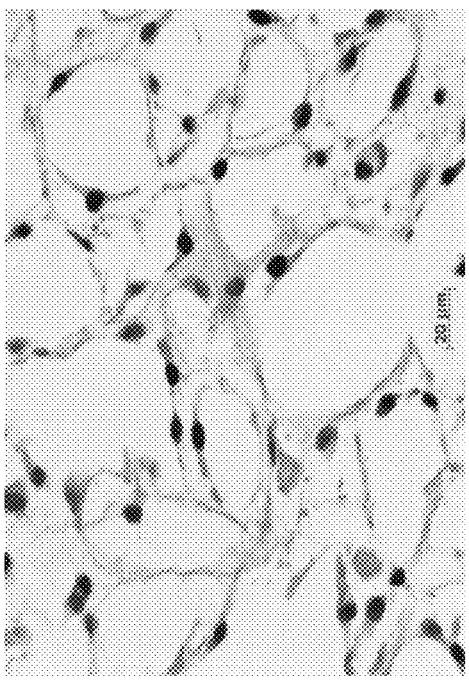
Figure 44A Ventilation: PCNA
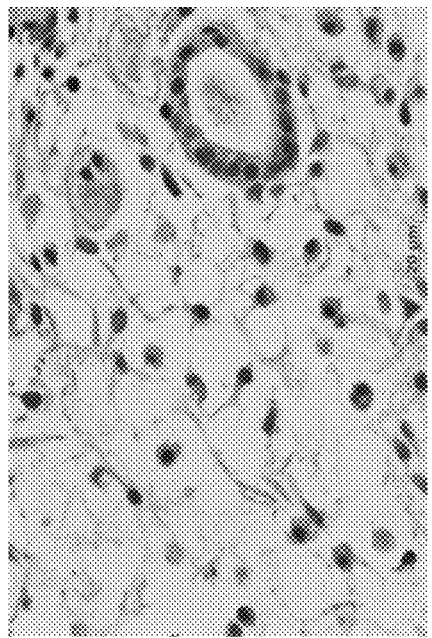
Figure 44C Perfusion: PCNA

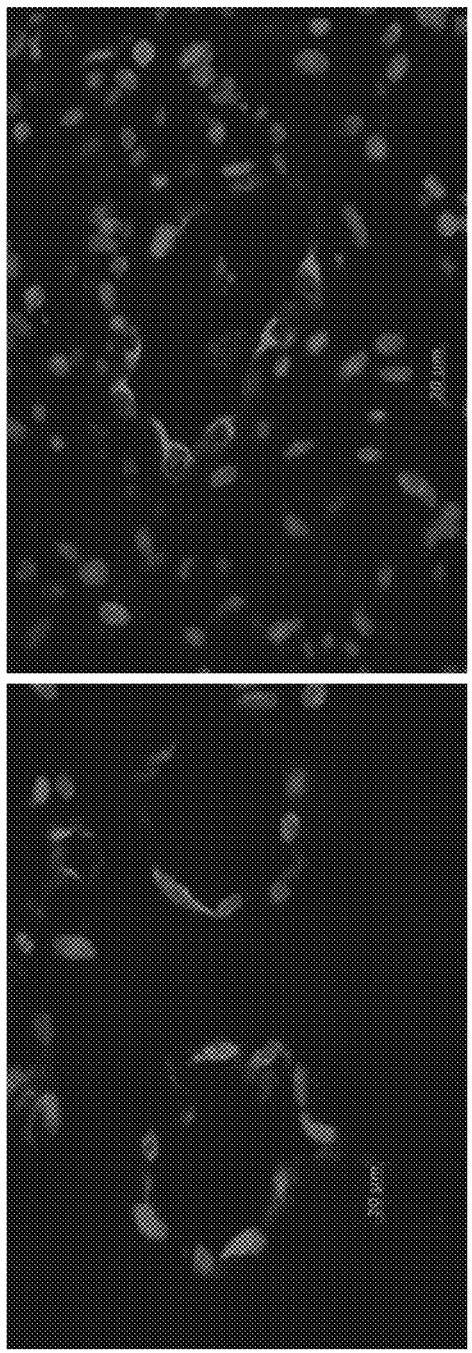
Figure 45A Ventilation
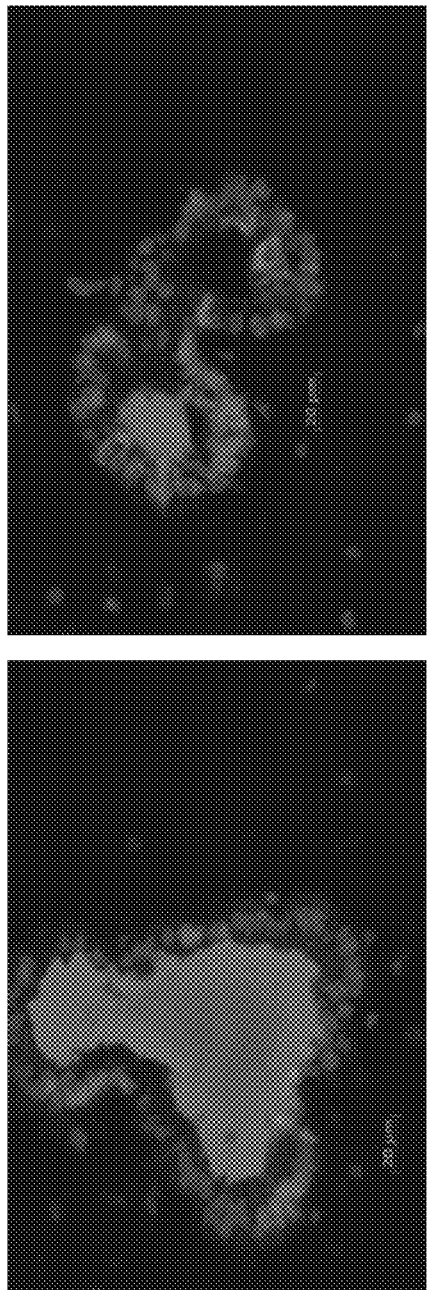
Figure 45B Perfusion

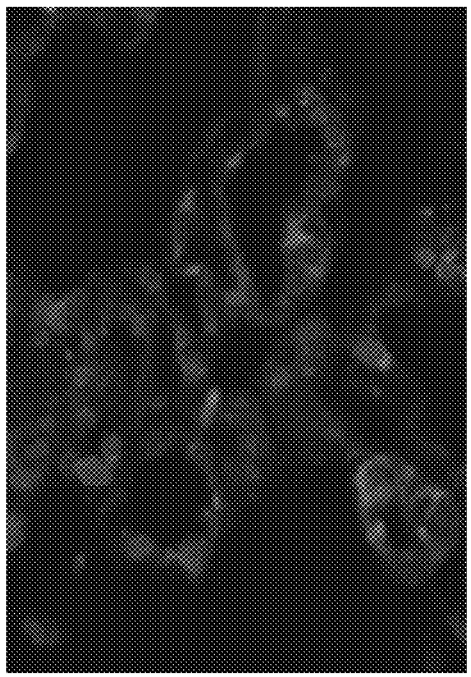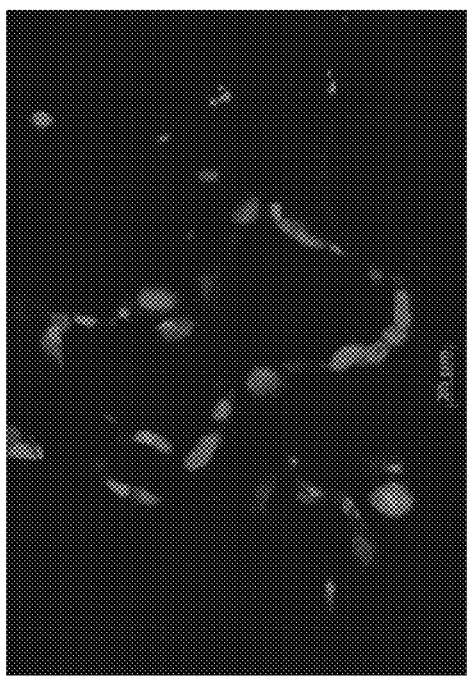
Figure 46A Ventilation
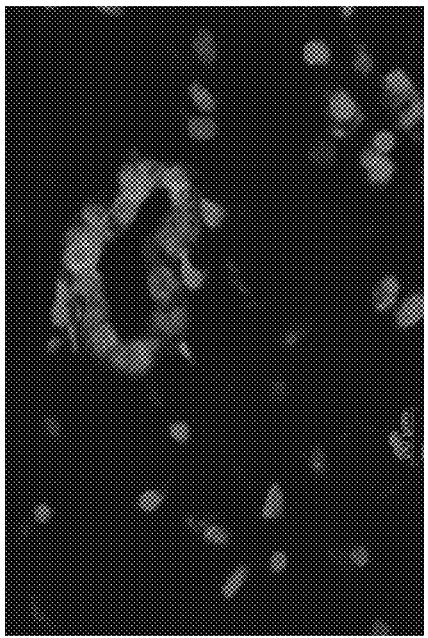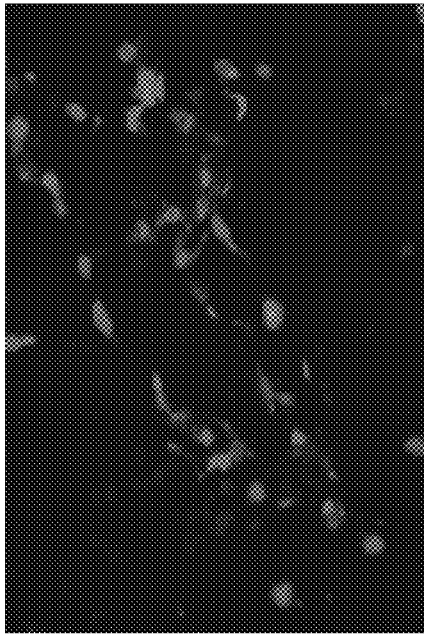
Figure 46B Perfusion

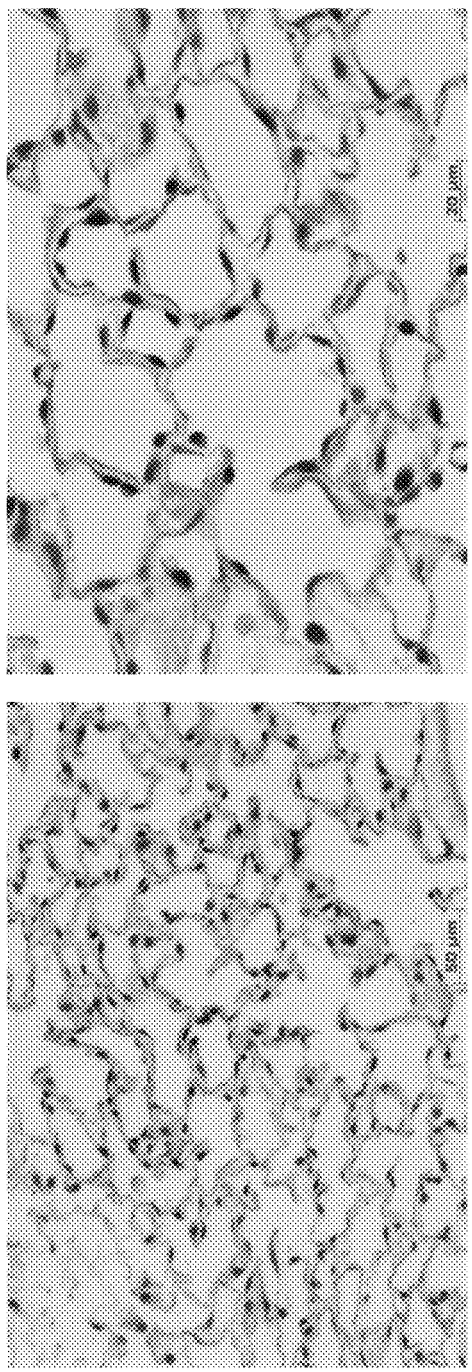 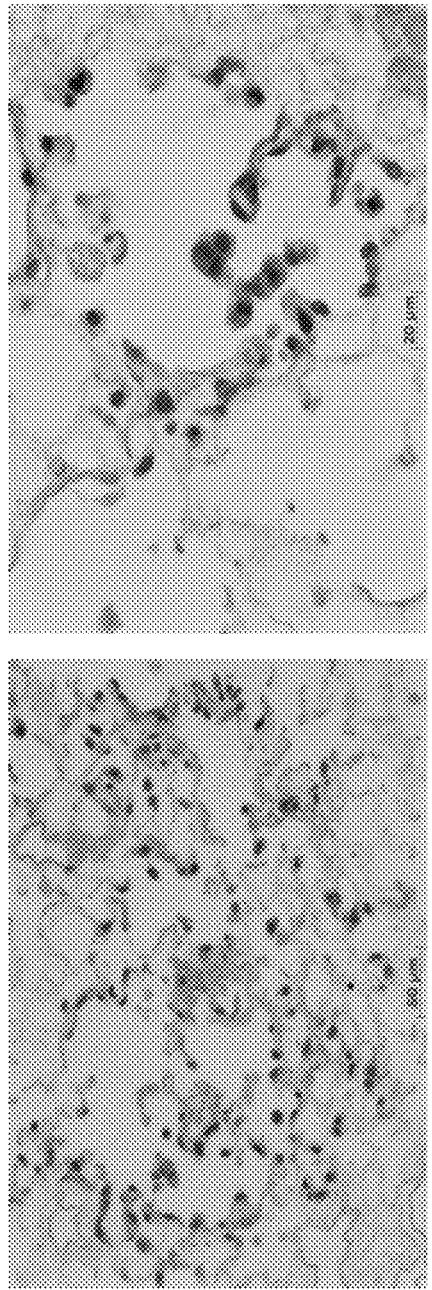
Figure 48A Engineered endothelium, with vascular perfusion at 3ml/min
Figure 48B Engineered endothelium, with ventilation at 1 breath/min

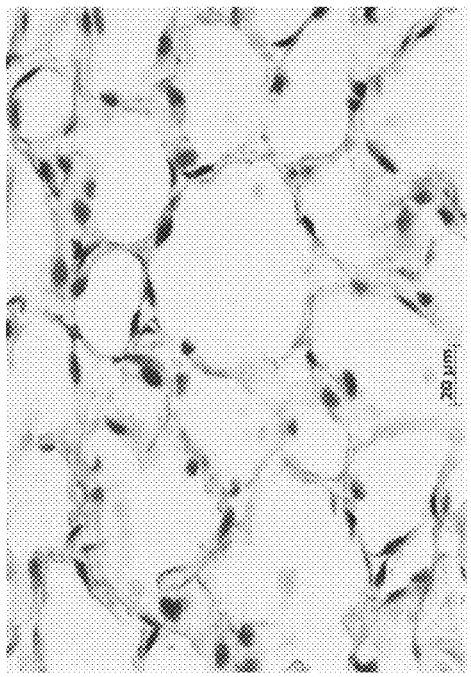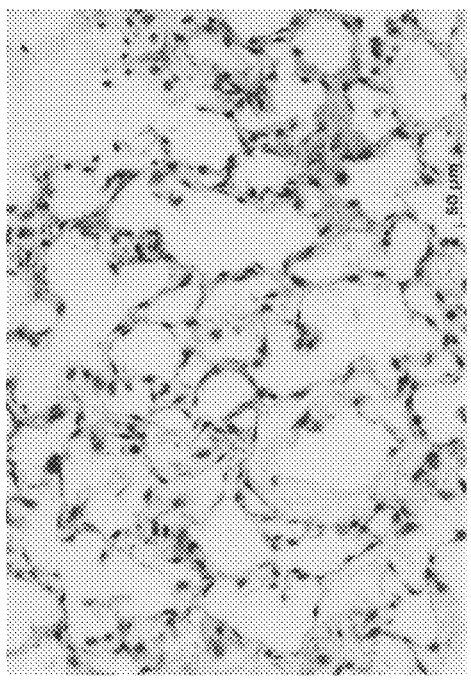
Figure 49A Engineered endothelium, with vascular perfusion at 3ml/min
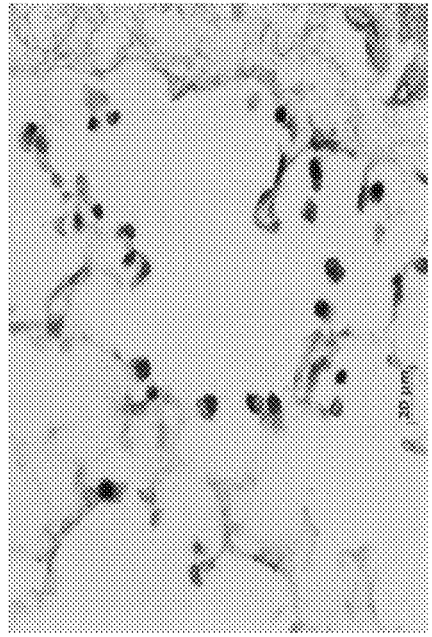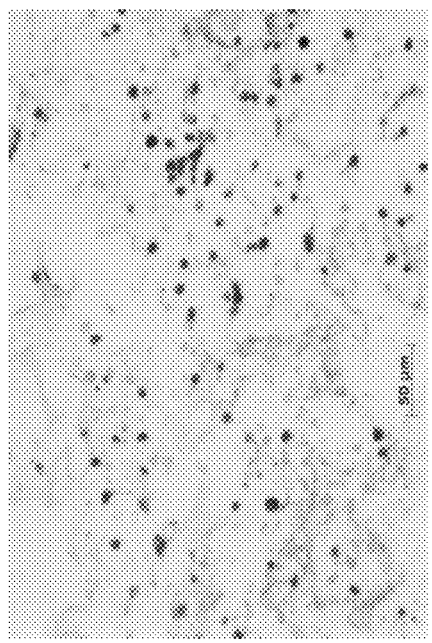
Figure 49B Engineered endothelium, with ventilation at 1 breath/min

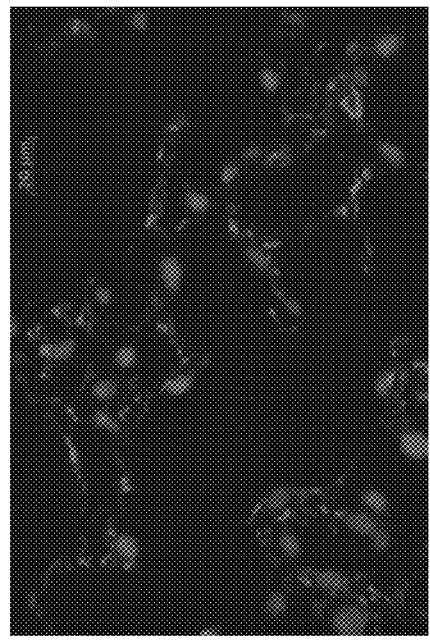
Figure 51B  Engineered perfused lung
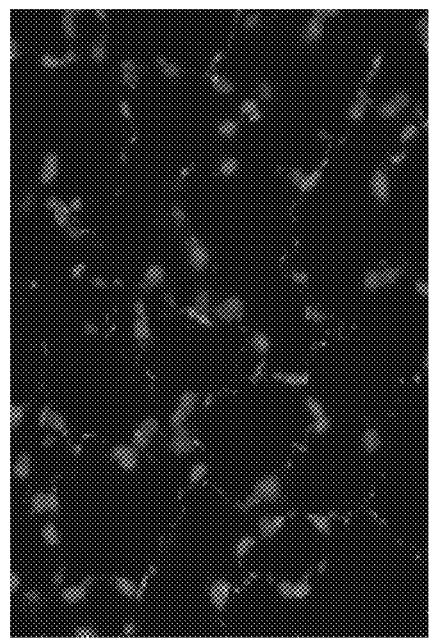
Figure 51A  Native lung

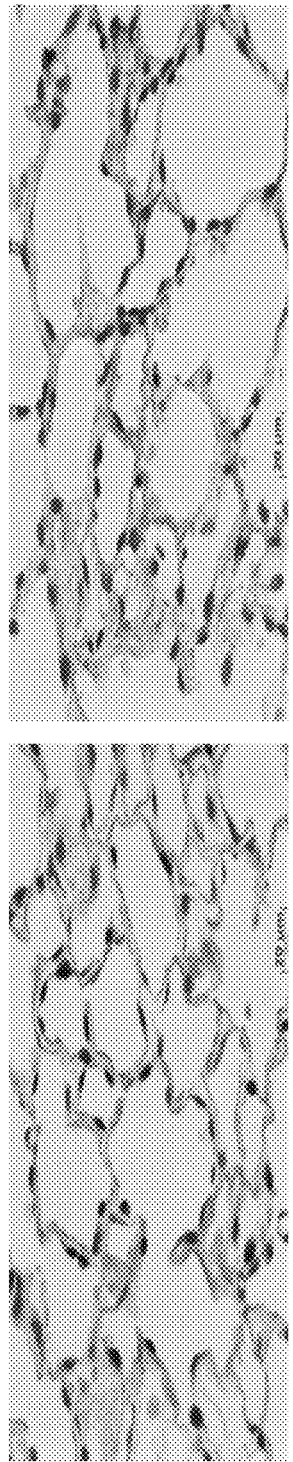
Figure 54A  MCDB-131 complete media, with 10%FBS and growth factors
Figure 54B  MCDB-131 with 10% FBS, no growth factors
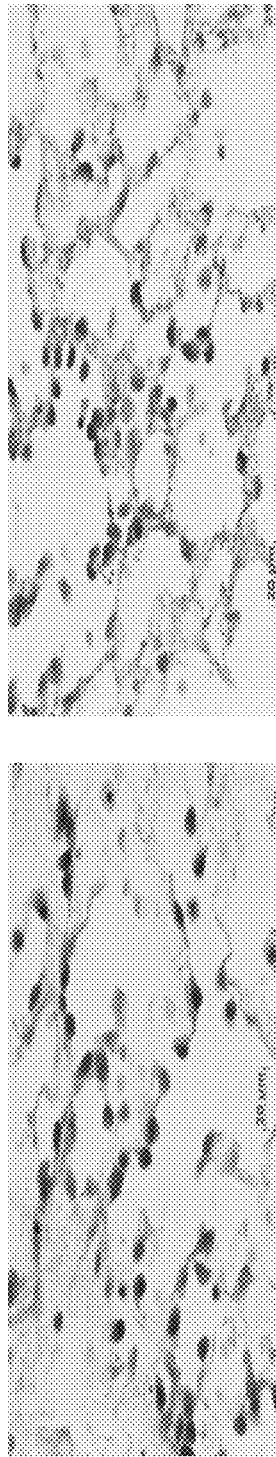
Figure 54C  DMEM with 10% FBS

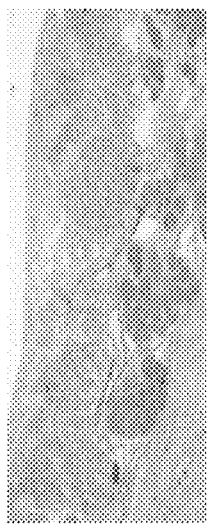 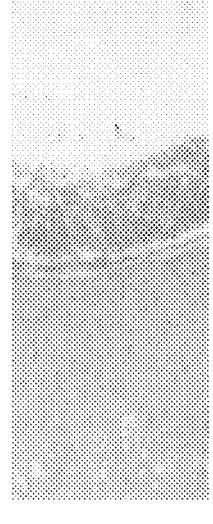 
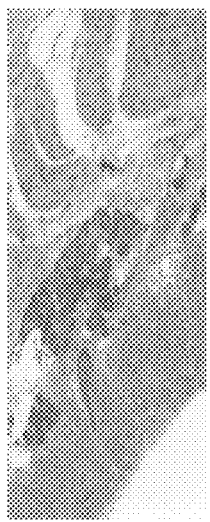 
Figure 55

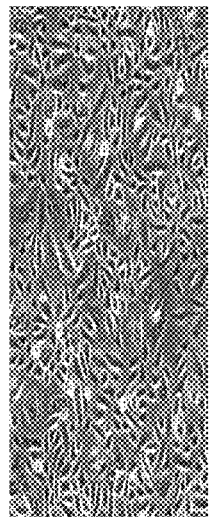 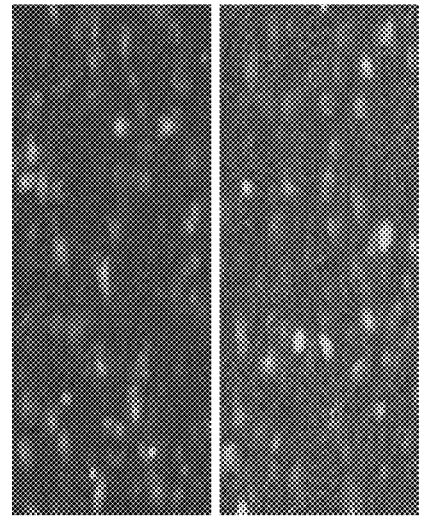
Figure 59

TISSUE ENGINEERING OF LUNG

CROSS-REFERENCE TO RELATED APPLICATIONS

This application is a divisional of U.S. patent application Ser. No. 14/625,080, filed Feb. 18, 2015, now U.S. Pat. No. 10,188,683, which is continuation of U.S. patent application Ser. No. 13/146,605, filed Oct. 10, 2011, now abandoned, which is a U.S. national phase application filed under 35 U.S.C. § 371 claiming benefit to International Patent Application No. PCT/US2010/023213, filed on Feb. 4, 2010, which is entitled to priority under 35 U.S.C. § 119(e) to U.S. Provisional Patent Application No. 61/206,799, filed on Feb. 4, 2009, each of which application is hereby incorporated herein by reference in its entirety.

BACKGROUND OF THE INVENTION

Every year, 400,000 Americans die of lung disease. Of further concern, the death rate due to lung disease is increasing, while the death rates for the other major disease categories are decreasing (heart disease, cancer and stroke). For several lung diseases, including cystic fibrosis, emphysema/COPD, and idiopathic pulmonary fibrosis, lung transplantation remains the only definitive treatment. However, patient survival after lung transplant is only 50% at 5 years and 24% at 10 years [Mondrinos et al., 2008, Tissue Eng 14:361-8]. There is therefore great demand for the development of engineered lung tissue that could be used for transplantation. One advantage of engineered lung tissue is that the tissue can be grown using a patient's own cells, thereby avoiding the need for strong immunosuppression, as is required with current lung transplantation. Immunosuppression is necessary to prevent rejection of the transplanted organ, but can lead to a wide range of problems, including infection, malignancy, kidney impairment, cardiovascular problems, and neurologic disorders [Pietra et al., 2000, J Clin Invest 106:1003-10; Christie et al., 2009, J Heart Lung Transplant 28:1031-49].

Tissue engineering is a growing field that seeks to combine cellular, molecular, technological and medical advances to create replacement tissues suitable for implantation. Promising work has been done on a variety of tissues, including blood vessels, urinary bladder, heart valves, and cardiac tissue [Nichols et al, 2008, Proc Am Thor Soc 5:723-30; Satchell et al., 2004, J Am Soc Nephrol 15:566-74; Atala et al., 2006, Lancet 367:1241-6; Orfanos et al., 2004, Intensive Care Med 30:1702-14]. However, lung is a difficult tissue to engineer in the laboratory. Lung requires a complex matrix that can withstand the mechanical pressures of breathing, that can support the growth of endothelial, epithelial and mesenchymal cells, and that provides a means for gas exchange between two very different yet intimately juxtaposed compartments.

Besides potential patient use in clinical settings, engineered lung tissue can be used in the laboratory to study a wide variety of important aspects of pulmonary biology and physiology. There are very few in vitro 3-dimensional lung culture models [Vandenbroucke et al., 2008, Ann NY Acad Sci 1123:134-45]. Furthermore, pulmonary endothelial and epithelial cells are more difficult to culture in the laboratory than many other cell types [Malda et al., 2004, Biomaterials 25:5773-80; Reichenspurner, 2005, J Heart Lung Transplant 24:119-30], and there has been relatively slow progress in the field of pulmonary progenitor and stem cell biology [Blaisdell et al., 2009, Stem Cells 27:2263-70; Muratore et al., 2008, J Surg Res 155(2):225-30]. Thus, there is a need in the art for the development of an in vitro lung tissue that replicates key features of the native pulmonary environment. The present invention satisfies this need in the art.

BRIEF SUMMARY OF THE INVENTION

The invention provides a decellularized tissue capable of supporting cell growth. Preferably, the decellularized tissue exhibits a characteristic of a corresponding natural tissue prior to decellularization. More preferably, the tissue is a lung.

In one embodiment, the decellularized tissue exhibits a morphology substantially similar to that of an otherwise identical tissue prior to decellularization.

In another embodiment, the decellularized tissue of claim 1 retaining an extracellular matrix of said corresponding natural tissue, wherein said extracellular matrix comprises an exterior surface, and wherein said exterior surface is substantially intact.

In another embodiment, immunogenic markers have been substantially removed from the decellularized tissue.

In one embodiment, the decellularized tissue exhibits mechanical properties substantially similar to that of a corresponding natural tissue.

The invention provides a composition comprising a three dimensional scaffold and a population of cells. Preferably, the composition is capable of supporting and maintaining the differentiation state of a lung cell.

In one embodiment, the three dimensional scaffold is a decellularized tissue.

In another embodiment, the composition exhibits an intact airway tree and vascular network.

In another embodiment, the population of cells comprises a stem cell.

In another embodiment, the population of cells comprises epithelial and endothelial cells.

In another embodiment, the cells are genetically modified. In one embodiment, the cell is genetically modified to express the CFTR gene.

In one embodiment, the composition is capable of supporting and maintaining the differentiation state of an alveolar epithelial cell.

In another embodiment, the scaffold comprises a biocompatible material selected from the group consisting of fibronectin, laminin, collagen, glycoprotein, thrombospondin, elastin, fibrillin, mucopolysaccharide, glycolipid, heparin sulfate, chondroitin sulfate, keratin sulfate, glycosaminoglycan, hyaluronic acid, proteoglycan, vitronectin, poly-D-lysine, polysaccharide, and combinations thereof.

In one embodiment, the cells exhibit gene expression associated with induction of branching morphogenesis.

In another embodiment, the composition comprises a characteristic of a lung tissue. In some instances, the characteristic is selected from the group consisting of branching morphogenesis, distal lung epithelial cytodifferentiation, epithelial growth, vascular development, and combinations thereof.

The invention provides a method of making an engineered three dimensional tissue capable of supporting and maintaining the differentiation state of a lung cell. The method comprises seeding a decellularized scaffold with a population of cells to produce a seeded scaffold.

The invention provides an in vitro method for screening a test agent for the ability of the test agent to modulate the health of a lung tissue. The method comprises contacting a test agent to an engineered three dimensional lung tissue model and measuring the effect the test agent has on the model. Any alteration to the model is an indication that the test agent is able to modulate the health of a lung tissue.

In one embodiment, the test agent is selected from the group consisting of a chemical agent, a pharmaceutical, a peptide, a nucleic acid, and radiation.

In another embodiment, the test agent is a delivery vehicle for a therapeutic agent.

In one embodiment, the method comprises determining the effect of the test agent on cell number, area, volume, shape, morphology, marker expression or chromosomal fragmentation.

In another embodiment, the method comprises the step of selecting an agent which has a desired effect on the lung tissue model.

The invention provides a method of alleviating or treating a lung defect in a mammal. The method comprises administering to a mammal a therapeutically effective amount of a composition comprising a three dimensional construct capable of supporting and maintaining the differentiation state of an lung cell, thereby alleviating or treating the lung defect in the mammal.

The invention provides an implantable composition comprising a decellularized tissue capable of supporting cell growth. Preferably, the decellularized tissue exhibits a characteristic of a corresponding natural tissue prior to decellularization.

In one embodiment, the implantable composition comprises a population of cells. Preferably, the implantable composition is capable of supporting and maintaining the differentiation state of a lung cell.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

FIGS. 1A through 1D are a series of images depicting H&E staining and quantitative DNA assay of native and decellularized lung. FIG. 1 demonstrates that cellular material was removed yet the architecture of the scaffold was retained. DNA was removed to ~1.2% of native levels. * indicates p<0.01. FIG. 1D is an image of decellularized lung.

FIGS. 2A and 2B are a series of images depicting staining for remnant DNA in decellularized scaffolds. DNA is stained using DAPI. Images were exposed for the same time to enable comparison.

FIGS. 4A and 4B are a series of images depicting collagen staining in native and decellularized lung. Collagen I is stained green, collagen IV is stained red, and nuclei are counterstained blue with DAPI. Collagen I is found near large vessels while collagen IV is distributed throughout the parenchyma. Note that in native lung, red blood cells in the parenchyma appear green due to autofluorescence.

FIGS. 5A and 5B are a series of images depicting scanning EM of native and decellularized lung. Alveolar septae are intact. Scale bars are 100 μm in left panels and 20 μm in right panels.

FIGS. 6A through 6C are a series of images depicting transmission EM of native and decellularized lung. The alveolar basement membrane is retained when decellularization perfusion pressure is maintained below 30 mmHg. C indicates capillaries, A indicates alveoli, and S indicates the alveolar septae. Scale bars are 2 μm in all panels.

FIG. 8 is a graph depicting retention of 5 μm microspheres by decellularized scaffolds. Microsphere assay demonstrates that low perfusion pressure (<30 mmHg) during decellularization enables the retention of 95% of 5 μm particles in the airway compartment. * indicates p<0.05 compared to native.

FIGS. 9A and 9B are a series of images of a Micro CT of the vasculature of native and decellularized lung. Overall, decellularized scaffolds appear similar to native, when imaged with a resolution of 58 μm.

FIGS. 10A and 10B are a series of images depicting high resolution micro CT of the vasculature of native and decellularized lung. Resolution of these scans is 6.5 μm.

FIGS. 12A through 12C are a series of images depicting collagen staining and content of native and decellularized lung. Masson's trichrome stain reveals wavy dark blue fibers in both native and decellularized lung. Quantitative assay demonstrates preservation of collagen in native and decellularized lungs, but loss of collagen after decellularization using sodium dodecylsulfate (SDS). * indicates p<0.01.

FIGS. 13A through 13C are a series of images depicting elastin histochemistry (Verhoff-van Geison) for native and decellularized lung. FIG. 13 depicts wavy dark elastin fibers in both native and decellularized lung. Quantitative assay demonstrates preservation of some elastin in decellularized lungs compared to native. * indicates p<0.01.

FIGS. 14A through 14C are a series of images depicting GAG histochemistry (Alcian blue) for native and decellularized lung. Depicted is blue GAG staining in native lung but their absence in decellularized lung. Quantitative assay demonstrates loss of sulfated GAGs in decellularized lungs compared to native lung. * indicates p<0.01.

FIGS. 15A and 15B are an image depicting stress-strain curves of native and decellularized lung. SDS indicates a lung treated with sodium dodecylsulfate.

FIGS. 17A and 17B are a series of images depicting schematic diagrams of the bioreactor used for in vitro lung culture.

FIGS. 18A and 18B are a series of images depicting pulmonary artery and tracheal pressures during in vitro lung culture. Perfusion rate is ~5 ml/min.

FIGS. 19A through 19C are a series of images depicting the effect of ventilation with air versus liquid on lung architecture and airway epithelium. Air ventilation causes airway dilation and destruction of the airway epithelium after a 3 day culture.

FIGS. 20A and 20B are a series of images depicting the effect of vascular perfusion and pressure on cell apoptosis and cell number during native lung culture. * indicates p<0.01 and # indicates p<0.05 compared to native.

FIGS. 21A through 21D are a series of images depicting a comparison of CCSP and SPC expression in native lung and perfused cultured lung. CCSP and SPC are stained in red, with nuclei counterstained blue with DAPI.

FIGS. 22A and 22B are a series of images depicting a comparison of PECAM expression in native lung and perfused cultured lung. PECAM expression is still noted for perfused lung culture (30 mmHg). PECAM is stained red, with nuclei counterstained blue with DAPI.

FIGS. 23A and 23B are a series of images depicting the effect of ventilation on cell apoptosis and cell number during native lung culture. * indicates p<0.01 and # indicates p<0.05 compared to native.

FIGS. 24A through 24C are a series of images depicting apoptotic nuclei in native and ventilated cultured lung. Ventilation with a single connection led to a much higher rate of apoptotic nuclei, as compared to native lung or ventilation with an airway 'loop'. Apoptotic nuclei are stained brown via TUNEL, with normal nuclei counterstained green.

FIGS. 25A through 25J are a series of images depicting alveolar structure in native and 7-day cultured lung. Cell morphology, alveolar structure, and septal architecture appear similar between native and cultured, ventilated lung. FIGS. 25C through 25J depicts maintenance of pulmonary cell differentiation after 7 days of in vitro ventilated lung culture.

FIGS. 27A and 27B are a series of images depicting H&E stain of the immortalized epithelial cell line MLE-12 cultured on decellularized scaffolds.

FIGS. 28A through 28F are a series of images depicting flow cytometry staining of a panel of pulmonary markers of isolated neonatal pulmonary cells. Blue or green curves are isotype control stains and red is the antigen indicated.

FIGS. 30A and 30B are a series of images depicting PCNA staining of engineered lung at 4 and 8 days of culture. Proliferating nuclei stain brown for PCNA; negative nuclei are counterstained with hematoxylin.

FIGS. 31A and 31B are a series of images depicting TUNEL staining of engineered lung at 4 and 8 days of culture. Positive nuclei are brown, while negative nuclei are counterstained with methyl green.

FIGS. 32A through 32C are a series of images depicting Clara Cell secretory protein (CCSP) staining of native and engineered lung at 4 days. CCSP is stained red, while nuclei are counterstained blue with DAPI.

FIGS. 33A through 33C are a series of images depicting surfactant protein C staining of native and engineered lung at 4 days and 8 days. SPC is stained red, while nuclei are counterstained blue with DAPI.

FIGS. 34A through 34C are a series of images depicting aquaporin-5 staining of native and engineered lung at 4 days. AQP is stained red, while nuclei are counterstained blue with DAPI.

FIGS. 36A through 36C are a series of images depicting cytokeratin-14 staining for basal cells in native and engineered lung. Cytokeratin stains red, while nuclei are counterstained blue with DAPI.

FIGS. 38A and 38B are a series of images depicting α-actin staining of native and engineered lung. α-actin is stained green, while nuclei are counterstained blue with DAPI.

FIGS. 39A through 39F are a series of images depicting the effect of media composition on epithelial development. Epithelial structures are driven towards apical expression of SPC granules with loss of CCSP expression when cultured in BGJb media. In DMEM media, cells retain expression of both SPC and CCSP, with SPC expression diffusely cytoplasmic.

FIGS. 41A through 41C are a series of images depicting the effect of ventilation with air on epithelial development in engineered lung tissue. AQP expression is noted in parenchymal cells (top left) that are also positive for SPC (FIG. 41B), as well as occasional strong expression in cuboidal epithelial cells (top right). CCSP expression of cuboidal epithelium is also noted (FIG. 41C).

FIGS. 42A and 42B are a series of images depicting ciliated epithelium in native and engineered lung. Ciliated cells are highlighted in red for engineered lung.

FIGS. 43A and 43B are a series of images depicting the effect of perfusion and ventilation on engineered lung culture.

FIGS. 44A through 44D are a series of images depicting the effect of perfusion and ventilation on cell proliferation and apoptosis in engineered lung culture.

FIGS. 45A and 45B are a series of images depicting the effect of perfusion and ventilation on CCSP expression in engineered lung tissue. CCSP is stained red, while nuclei are counterstained blue with DAPI.

FIGS. 46A through 46B are a series of images depicting the effect of perfusion and ventilation on SPC expression in engineered lung tissue. SPC is stained in red, and nuclei are counterstained blue with DAPI.

FIGS. 48A and 48B are a series of images depicting H&E staining of perfused versus ventilated engineered lung endothelium.

FIGS. 49A and 49B are a series of images depicting TUNEL staining of perfused versus ventilated engineered lung endothelium. EG cultured with ventilation only are substantially more apoptotic than perfused lung. Apoptotic nuclei stain brown via TUNEL while negative nuclei are counterstained with methyl green.

FIGS. 51A and 51B are a series of images depicting expression of VE-cadherin in native and engineered lung. VE-cadherin is stained red, with nuclei counterstained blue with DAPI.

FIGS. 54A through 54C are a series of images depicting medium impacts the growth of engineered endothelial tissue. Engineered perfused endothelium was cultured in the indicated medium type. H&E histology is shown in the left panels, while right panels show apoptotic nuclei in brown (via TUNEL) while normal nuclei are counterstained with methyl green.

FIG. 55 is a series of images demonstrating that decellularized trachea prepared with incubation in CHAPS buffer for 4-8 hours maintained collagen matrix and exhibited removal of most cells from the tissue.

FIG. 59 is a series of images demonstrating that NHBE infected with GFP lentivirus did not show obvious morphology change after 6 hours.

DETAILED DESCRIPTION OF THE INVENTION

Figure 1D:
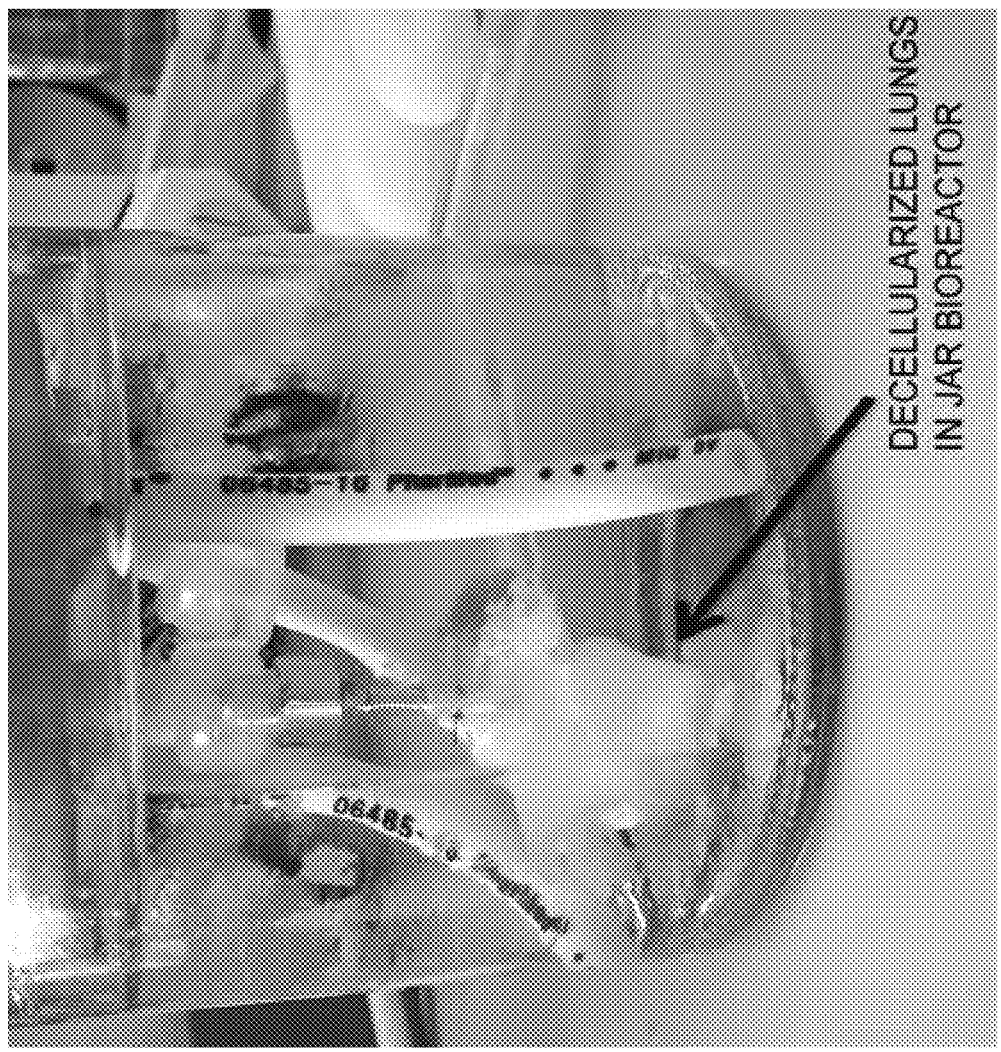

The present invention provides an engineered lung tissue. The present invention is partly based on the discovery that a three dimensional lung tissue can be generated to exhibit characteristics of a natural lung tissue.

In one embodiment, the engineered lung tissue is derived from a decellularized native lung tissue. The decellularized tissues are substantially devoid of cells and DNA. Preferably, the decellularized tissue is also devoid of immunogenic molecules. More preferably, the decellularized tissue retains several key extracellular matrix molecules that are important for cell attachment and proliferation.

The invention includes a method of decellularizing a tissue. The decellularization method includes removing cellular and nuclear material from the tissue while retaining key aspects of and minimizing any damage to the extracellular matrix of the lung. In one embodiment, the decellularization process also includes removing antigenic molecules from the tissue thereby rendering the tissue non-immunogenic. In one embodiment, the decellularization process of the invention includes generating a decellularized scaffold that is fully compatible with cell culture and at the same time provides a barrier function. Preferably, the decellularized scaffold is a lung scaffold that has an intact airway tree and vascular network.

The invention also includes a bioreactor. Preferably, the bioreactor is capable of supporting the in vitro culturing of any 3-dimensional tissue. In one embodiment, the bioreactor is capable of ventilating lungs via negative pressure as well as providing vascular perfusion and ventilation at physiologic rates and pressures. The bioreactor enables among other things the perfusion of media through the vasculature, the movement of media or air in and out of the airways, and the ventilation of the lungs via negative (as well as positive) pressure.

The in vitro three dimensional model of lung tissue of the invention is useful for investigating lung developmental biology. In addition, the model is useful for among other things, drug discovery, toxicity testing, disease pathology, and the like.

The invention is also related to the discovery that lung tissue can be generated in vitro. The in vitro model recapitulates the formation of structures reminiscent of alveolar forming units comprised of ductal epithelium tightly interfaced with the host circulation. Accordingly, the invention provides methods and compositions for the generation of vascularized pulmonary tissues as a form of regenerative medicine.

The invention also provides a method of alleviating or treating a lung defect in a mammal, preferably a human. The method comprises administering to the mammal in need thereof a therapeutically effective amount of a composition comprising a three dimensional construct of the invention, thereby alleviating or treating the lung defect in the mammal.

Definitions

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry, and nucleic acid chemistry and hybridization are those well known and commonly employed in the art.

Standard techniques are used for nucleic acid and peptide synthesis. The techniques and procedures are generally performed according to conventional methods in the art and various general references (e.g., Sambrook and Russell, 2001, Molecular Cloning, A Laboratory Approach, Cold Spring Harbor Laboratory Press, Cold Spring Harbor, N.Y., and Ausubel et al., 2002, Current Protocols in Molecular Biology, John Wiley & Sons, New York, N.Y.), which are provided throughout this document.

The articles "a" and "an" are used herein to refer to one or to more than one (i.e., to at least one) of the grammatical object of the article. By way of example, "an element" means one element or more than one element.

The term "about" will be understood by persons of ordinary skill in the art and will vary to some extent based on the context in which it is used.

The terms "precursor cell," "progenitor cell," and "stem cell" are used interchangeably in the art and as used herein refer either to a pluripotent or lineage-uncommitted progenitor cell, which is potentially capable of an unlimited number of mitotic divisions to either renew itself or to produce progeny cells which will differentiate into the desired cell type. In contrast to pluripotent stem cells, lineage-committed progenitor cells are generally considered to be incapable of giving rise to numerous cell types that phenotypically differ from each other. Instead, progenitor cells give rise to one or possibly two lineage-committed cell types.

The term "dedifferentiation", as used herein, refers to the return of a cell to a less specialized state. After dedifferentiation, such a cell will have the capacity to differentiate into more or different cell types than was possible prior to re-programming. The process of reverse differentiation (i.e., de-differentiation) is likely more complicated than differentiation and requires "re-programming" the cell to become more primitive.

As used herein, "scaffold" refers to a structure, comprising a biocompatible material, that provides a surface suitable for adherence and proliferation of cells. A scaffold may further provide mechanical stability and support. A scaffold may be in a particular shape or form so as to influence or delimit a three-dimensional shape or form assumed by a population of proliferating cells. Such shapes or forms include, but are not limited to, films (e.g. a form with two-dimensions substantially greater than the third dimension), ribbons, cords, sheets, flat discs, cylinders, spheres, 3-dimensional amorphous shapes, etc.

As used here, "biocompatible" refers to any material, which, when implanted in a mammal, does not provoke an adverse response in the mammal. A biocompatible material, when introduced into an individual, is not toxic or injurious to that individual, nor does it induce immunological rejection of the material in the mammal.

As used herein, "autologous" refers to a biological material derived from the same individual into whom the material will later be re-introduced.

As used herein, "allogeneic" refers to a biological material derived from a genetically different individual of the same species as the individual into whom the material will be introduced.

As used herein, a "graft" refers to a cell, tissue or organ that is implanted into an individual, typically to replace, correct or otherwise overcome a defect. A graft may further comprise a scaffold. The tissue or organ may consist of cells that originate from the same individual; this graft is referred to herein by the following interchangeable terms: "autograft", "autologous transplant", "autologous implant" and "autologous graft". A graft comprising cells from a genetically different individual of the same species is referred to herein by the following interchangeable terms: "allograft", "allogeneic transplant", "allogeneic implant" and "allogeneic graft". A graft from an individual to his identical twin is referred to herein as an "isograft", a "syngeneic transplant", a "syngeneic implant" or a "syngeneic graft". A "xenograft", "xenogeneic transplant" or "xenogeneic implant" refers to a graft from one individual to another of a different species.

As used herein, the terms "tissue grafting" and "tissue reconstructing" both refer to implanting a graft into an individual to treat or alleviate a tissue defect, such as a lung defect or a soft tissue defect.

As used herein, to "alleviate" a disease, defect, disorder or condition means reducing the severity of one or more symptoms of the disease, defect, disorder or condition.

As used herein, to "treat" means reducing the frequency with which symptoms of a disease, defect, disorder, or adverse condition, and the like, are experienced by a patient.

As used herein, a "therapeutically effective amount" is the amount of a composition of the invention sufficient to provide a beneficial effect to the individual to whom the composition is administered.

As used herein, the term "growth medium" is meant to refer to a culture medium that promotes growth of cells. A growth medium will generally contain animal serum. In some instances, the growth medium may not contain animal serum.

"Differentiation medium" is used herein to refer to a cell growth medium comprising an additive or a lack of an additive such that a stem cell, fetal pulmonary cell or other such progenitor cell, that is not fully differentiated, develops into a cell with some or all of the characteristics of a differentiated cell when incubated in the medium.

As used herein, the term "growth factor product" refers to a protein, peptide, mitogen, or other molecule having a growth, proliferative, differentiative, or trophic effect on a cell. Growth factors include, but are not limited to, fibroblast growth factor (FGF), basic fibroblast growth factor (bFGF), acidic fibroblast growth factor (aFGF), epidermal growth factor (EGF), insulin-like growth factor-I (IGF-T), insulin-like growth factor-II (IGF-II), platelet-derived growth factor (PDGF), vascular endothelial cell growth factor (VEGF), activin-A, bone morphogenic proteins (BMPs), insulin, growth hormone, erythropoietin, thrombopoietin, interleukin 3 (IL-3), interleukin 6 (IL-6), interleukin 7 (IL-7), macrophage colony stimulating factor, c-kit ligand/stem cell factor, osteoprotegerin ligand, insulin, nerve growth factor, ciliary neurotrophic factor, cytokines, chemokines, morphogens, neutralizing antibodies, other proteins, and small molecules. Preferably, the FGF is selected from the group selected from FGF2, FGF7, FGF10, and any combination thereof.

An "isolated cell" refers to a cell which has been separated from other components and/or cells which naturally accompany the isolated cell in a tissue or mammal.

As used herein, a "fetal pulmonary cells" (FPCs) refer to cells isolated from the lung tissue of an embryo. A mixed population of FPCs can include, but is not limited to epithelial, mesenchymal, and endothelial cells.

As used herein, "epithelial cell" means a cell which forms the outer surface of the body and lines organs, cavities and mucosal surfaces.

As used herein, "endothelial cell" means a cell which lines the blood and lymphatic vessels and various other body cavities.

As used herein, a "substantially purified" cell is a cell that is essentially free of other cell types. Thus, a substantially purified cell refers to a cell which has been purified from other cell types with which it is normally associated in its naturally-occurring state.

"Expandability" is used herein to refer to the capacity of a cell to proliferate, for example, to expand in number or, in the case of a population of cells, to undergo population doublings.

The term "lung specific" refers to a nucleic acid molecule or polypeptide that is expressed predominantly in the lung as compared to other tissues in the body. In a preferred embodiment, a "lung specific" nucleic acid molecule or polypeptide is expressed at a level that is 5-fold higher than any other tissue in the body. In a more preferred embodiment, the "lung specific" nucleic acid molecule or polypeptide is expressed at a level that is 10-fold higher than any other tissue in the body, more preferably at least 15-fold, 20-fold, 25-fold, 50-fold or 100-fold higher than any other tissue in the body. Nucleic acid molecule levels may be measured by nucleic acid hybridization, such as Northern blot hybridization, or quantitative PCR. Polypeptide levels may be measured by any method known to accurately measure protein levels, such as Western blot analysis.

"Proliferation" is used herein to refer to the reproduction or multiplication of similar forms, especially of cells. That is, proliferation encompasses production of a greater number of cells, and can be measured by, among other things, simply counting the numbers of cells, measuring incorporation of $^3$H-thymidine into the cell, and the like.

As used herein, "tissue engineering" refers to the process of generating tissues ex vivo for use in tissue replacement or reconstruction. Tissue engineering is an example of "regenerative medicine," which encompasses approaches to the repair or replacement of tissues and organs by incorporation of cells, gene or other biological building blocks, along with bioengineered materials and technologies.

As used herein "endogenous" refers to any material from or produced inside an organism, cell or system.

"Exogenous" refers to any material introduced into or produced outside an organism, cell, or system.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

An "isolated nucleic acid" refers to a nucleic acid segment or fragment which has been separated from sequences which flank it in a naturally-occurring state, i.e., a DNA fragment which has been removed from the sequences which are normally adjacent to the fragment, i.e., the sequences adjacent to the fragment in a genome in which it naturally occurs. The term also applies to nucleic acids which have been substantially purified from other components which naturally accompany the nucleic acid, i.e., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (i.e., as a cDNA or a genomic or cDNA fragment produced by PCR or restriction enzyme digestion) independent of other sequences. It also includes a recombinant DNA which is part of a hybrid gene encoding additional polypeptide sequence.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

The phrase "under transcriptional control" or "operatively linked" as used herein means that the promoter is in the correct location and orientation in relation to the polynucleotides to control RNA polymerase initiation and expression of the polynucleotides.

As used herein, the term "promoter/regulatory sequence" means a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

A "constitutive" promoter is a nucleotide sequence which, when operably linked with a polynucleotide which encodes or specifies a gene product, causes the gene product to be produced in a cell under most or all physiological conditions of the cell.

An "inducible" promoter is a nucleotide sequence which, when operably linked with a polynucleotide which encodes or specifies a gene product, causes the gene product to be produced in a cell substantially only when an inducer which corresponds to the promoter is present in the cell.

The term "tissue," as used herein includes, but is not limited to, bone, neural tissue, fibrous connective tissue including tendons and ligaments, cartilage, dura, pericardia, muscle, lung, heart valves, veins and arteries and other vasculature, dermis, adipose tissue, or glandular tissue.

A "tissue-specific" promoter is a nucleotide sequence which, when operably linked with a polynucleotide which encodes or specifies a gene product, causes the gene product to be produced in a cell substantially only if the cell is a cell of the tissue type corresponding to the promoter.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, and the like.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (i.e., naked or contained in liposomes) and viruses that incorporate the recombinant polynucleotide.

As used herein, the terms "subject" and "patient" are used interchangeably. As used herein, a subject is preferably a mammal such as a non-primate (e.g., cows, pigs, horses, cats, dogs, rats, etc.) and a primate (e.g., monkey and human), most preferably a human.

Description

The present invention provides an engineered three dimensional pulmonary tissue and methods of making the three dimensional pulmonary tissue. Preferably, the pulmonary tissue is a lung tissue. In one embodiment, the engineered pulmonary tissue exhibits branching morphogenesis exemplified by natural pulmonary tissue. Thus, the invention provides an in vitro model that mimics natural pulmonary tissue. The in vitro three dimensional pulmonary tissue model is useful for among other things, drug discovery, toxicity testing, disease pathology, and the like.

The invention is based on the discovery of a procedure useful for decellularizing lung tissue using a technique that removes cellular material but that retains key components of the extracellular matrix. The development of a decellularized lung matrix is important as a scaffold for tissue engineering applications. Accordingly, the invention includes a method for substantially decellularizing a tissue or organ. Preferably, the method significantly reduces or eliminates immunogenicity of the tissue or organ such that upon transplantation, the tissue or organ is not rejected by the recipient's immune system. The method includes removing the tissue from a donor, processing the tissue to remove substantially all of the cells of the tissue or organ. The method further includes repopulating the decellularized scaffold through seeding with cells including but not limited to stem cells, fetal cells and the like, for implantation into recipient. Preferably, the decellularized scaffold is seeded with non-immunogenic cells. In one embodiment, the decellularized scaffold is seeded with cells that are autologous to the intended recipient. Depending on the type of tissue being treated and to be replaced, different stem cells known in the art or which become known hereafter are selected such that appropriate tissues are formed upon implantation into a recipient of the seeded implant.

In some instances, the engineered three dimensional pulmonary tissue comprises cells cultured on the tissue. Any suitable cells can be used for culturing on the decellularized tissue of the invention. In some instances, stems cells are cultured on the decellularized tissue for regeneration of lung tissue. In some instances, fetal or neonatal pulmonary cells (NPCs) are cultured on the decellularized tissue. In some instances, a mixed population of NPCs are used, wherein the population of NPCs include, but are not limited to epithelial cells, mesenchymal cells, and endothelial cells.

After seeding, the cells on the scaffold are optionally subjected to an expansion medium or to a differentiation medium or cultured in the presence of tissue-specific growth factors. The composition is then implanted into a subject in need thereof. The subject may be a mammal, but is preferably a human and the source of the cells for growth and implantation is any mammal, preferably a human. The implanted composition supports additional cell growth in vivo, thus providing tissue reconstruction. Accordingly, the invention provides the use of engineered three dimensional pulmonary tissue for tissue grafting therapies.

The invention also includes generation of pulmonary tissue in vivo. Preferably, vascularized pulmonary tissue is generated in vivo. In one aspect, the fetal pulmonary cells are administered in the context of the decellularized tissue to a mammal to facilitate in vivo pulmonary tissue formation.

In the present invention, it is demonstrated that the decellularized tissue can be seeded with suitable cells, such as neonatal or adult pulmonary cells, and the resultant composition can be used as a vascularized three dimensional pulmonary tissue model for preclinical in vitro pharmacological, physiological, and scientific testing. In addition, the decellularized tissue can be seeded with suitable cells, such as neonatal pulmonary cells or autologous pulmonary cells, and the resultant composition can be used for tissue reconstruction in vivo.

The compositions and methods of the instant invention have myriad useful applications. The compositions may be used in therapeutic methods for alleviating or treating tissue defects in an individual. The compositions may also be used in vitro or in vivo to identify therapeutic compounds and therefore may have therapeutic potential.

Decellularization

The present invention provides an advancement over tissue engineering techniques known in the art. Specifically, the present invention provides a method of making engineered tissue scaffolds using a decellularized tissue as a starting source, preferably a decellularized natural tissue derived from a mammal.

The decellularization process relies on a chemical methodology. In one aspect, the chemical solution or otherwise referred to as the decellularization solution used for decellularization generally includes at least a hypertonic solution, a detergent, and a chelating agent. Preferably, the hypertonic solution is a hypertonic sodium chloride solution. Preferably, the detergent is a zwitterionic detergent such as CHAPS. Preferably, the chelating agent is EDTA.

In one embodiment, the decellularization solution can include a buffer (e.g., PBS) for osmotic compatibility with the cells. In some instances, the decellularization solution also can include enzymes such as, without limitation, one or more collagenases, one or more dispases, one or more DNases, or a protease such as trypsin. In some instances, the decellularization solution also or alternatively can include inhibitors of one or more enzymes (e.g., protease inhibitors, nuclease inhibitors, and/or collegenase inhibitors).

In one embodiment, the method to decellularize a tissue of the invention includes perfusing the tissue with the decellularization solution. The pressure for which the decellularization solution is perfused through the tissue can be adjusted to the desired pressure. Preferably, the decellularization solution is perfused through the tissue at perfusion pressure below about 30 mmHg. More preferably, the decellularization solution is perfused through the tissue at pressures less than about 20 mmHg.

In one embodiment, the decellularization solution can be introduced into the airway of the lung tissue to effect cell removal.

In one embodiment, the decellularized tissue of the invention consists essentially of the extracellular matrix (ECM) component of all or most regions of the tissue, including ECM components of the vascular tree. ECM components can include any or all of the following: fibronectin, fibrillin, laminin, elastin, members of the collagen family (e.g., collagen I, III, and IV), glycosaminoglycans, ground substance, reticular fibers and thrombospondin, which can remain organized as defined structures such as the basal lamina. Successful decellularization is defined as the absence of detectable myofilaments, endothelial cells, smooth muscle cells, epithelial cells, and nuclei in histologic sections using standard histological staining procedures.

Preferably, but not necessarily, residual cell debris also has been removed from the decellularized tissue.

In one embodiment, the decellularization process of a natural tissue preserves the native 3-dimensional structure of the tissue. That is, the morphology and the architecture of the tissue, including ECM components be maintained during and following the process of decellularization. The morphology and architecture of the ECM can be examined visually and/or histologically. For example, the basal lamina on the exterior surface of a solid organ or within the vasculature of an organ or tissue should not be removed or significantly damaged due to decellularization. In addition, the fibrils of the ECM should be similar to or significantly unchanged from that of an organ or tissue that has not been decellularized.

In one embodiment, one or more compounds can be applied in or on a decellularized tissue to, for example, preserve the decellularized tissue, or to prepare the decellularized tissue for recellularization and/or to assist or stimulate cells during the recellularization process. Such compounds include, but are not limited to, one or more growth factors (e.g., VEGF, DKK-1, FGF, BMP-1, BMP-4, SDF-1, IGF, and HGF), immune modulating agents (e.g., cytokines, glucocorticoids, IL2R antagonist, leucotriene antagonists), and/or factors that modify the coagulation cascade (e.g., aspirin, heparin-binding proteins, and heparin). In addition, a decellularized organ or tissue can be further treated with, for example, irradiation (e.g., UV, gamma) to reduce or eliminate the presence of any type of microorganism remaining on or in a decellularized tissue.

Use of the decellularization solution of the invention to generate a decellularized tissue provides a controlled, precise way to destroy cells of a tissue, while leaving the underlying ECM, including vascularization, and other gross morphological features of the original tissue intact. The decellularized scaffolds are then suitable for seeding with appropriate cells. Where the process is performed in vitro, the seeded tissue is suitable for implantation into the recipient as a replacement tissue. In addition to the decellularized tissues themselves, the invention includes methods of fabrication of engineered tissues built from such scaffolds.

The present invention provides a method suitable for producing a tissue scaffold for use in tissue engineering. Although the source of the tissue is not limited, in exemplary embodiments, the tissue is from a relatively large animal or an animal recognized as having a similar anatomy (with regard to the tissue of interest) as a human, such as a pig, a cow, a horse, a monkey, or an ape. In some embodiments, the source of the tissue is human, use of which can reduce the possibility of rejection of engineered tissues based on the scaffold. In preferred embodiments, the method leaves intact vascular structures of the tissue, such as alveolar architecture with preservation of the alveolar septae. As used herein, the term "intact" refers to a state of being whereby an element is capable of performing its original function to a substantial extent.

In one embodiment, the decellularized lung retains several key characteristics of normal lung matrix. For example, the decellularized lung comprises at least one or more of collagen, elastin, fibronectin, and proteoglycan The decellularized tissue does not retain either major histocompatibility complex (MHC) class I or II antigen, therefore the tissue does not elicit an adverse an immune response when administered to a recipient.

The decellularized tissue retains mechanics properties of normal native lung. The decellularized tissue also retains some of the barrier function of normal native lung.

Bioreactor

The invention provides a system (e.g., a bioreactor) for decellularizing and/or recellularizing tissue. The bioreactor enables the maintenance of cell viability, cellular differentiation state, and lung morphology. Decellularized scaffolds, when cultured in the bioreactor with a suitable cell source, can support the adherence and proliferation of a wide range of cell types, including pulmonary endothelial, epithelial, and mesenchymal cells. The bioreactor of the invention incorporates key features of the vivo environment. The bioreactor was designed to allow modifications for optimizing decellularization and/or recellularization processes. In one embodiment, the bioreactor is capable of perfusing media through the vasculature at a rate specified by the user and within the physiological flow and pressure levels of a mammal. In another embodiment, the bioreactor is capable of ventilating the tissue (e.g., lung) with air or media through the trachea. Preferably, negative pressure ventilation is used in order to be consistent with normal physiological conditions, though ventilation using positive pressure can also be done. In yet another embodiment, the bioreactor is capable of allowing different media types to bathe the vascular and airway compartments of the tissue. In another embodiment, the bioreactor allows for gas exchange into the culture medium, while simultaneously meeting the desired requirements for ventilation. In another embodiment, the bioreactor has ports to allow for pressure measurements, for example measurements of the pulmonary artery and tracheal pressures. Preferably, pressures are within normal physiological values. In another embodiment, the bioreactor has a means of allowing media exchange on a periodic basis.

The bioreactor of the invention generally includes at least one cannulation device for cannulating a tissue, a perfusion apparatus for perfusing media through the cannula(s), and means (e.g., a containment system) to maintain a sterile environment for the organ or tissue. A cannulation device generally includes size-appropriate hollow tubing for introducing into a vessel, duct, and/or cavity of a tissue. Typically, one or more vessels, ducts, and/or cavities are cannulated in a tissue. A perfusion apparatus can include a holding container for the liquid (e.g., a cellular disruption medium) and a mechanism for moving the liquid through the organ (e.g., a pump, air pressure, gravity) via the one or more cannulae. The sterility of a tissue during decellularization and/or recellularization can be maintained using the methods discussed elsewhere herein.

The bioreactor for can be used to decellularize and recellularize tissues as described herein. The process can be monitored for certain perfusion characteristics (e.g., pressure, volume, flow pattern, temperature, gases, pH), mechanical forces (e.g., ventricular wall motion and stress), and electrical stimulation (e.g., pacing). The effectiveness of perfusion can be evaluated in the effluent and in tissue sections. Perfusion volume, flow pattern, temperature, partial $O_2$ and $CO_2$ pressures and pH can be monitored using standard methods.

Sensors can be used to monitor the bioreactor and/or the tissue. Sonomicrometry, micromanometry, and/or conductance measurements can be used to acquire pressure-volume. For example, sensors can be used to monitor the pressure of a liquid moving through a cannulated organ or tissue; the ambient temperature in the system and/or the temperature of the organ or tissue; the pH and/or the rate of flow of a liquid moving through the cannulated organ or tissue; and/or the biological activity of a recellularizing tissue. In addition to having sensors for monitoring such features, a system for decellularizing and/or recellularizing a tissue also can include means for maintaining or adjusting such features. Means for maintaining or adjusting such features can include components such as a thermometer, a thermostat, electrodes, pressure sensors, overflow valves, valves for changing the rate of flow of a liquid, valves for opening and closing fluid connections to solutions used for changing the pH of a solution, a balloon, an external pacemaker, and/or a compliance chamber. To help ensure stable conditions (e.g., temperature), the chambers, reservoirs and tubings can be water-jacketed.

The bioreactor is capable of providing sufficient nutrient supply and mechanical stimulation to the lung tissue in order to support cell survival and differentiation. The bioreactor can be used for in vitro lung tissue culture and for engineered lung tissue culture. Preferably, the bioreactor is used to culture engineered lung tissue using the decellularized lung scaffolds of the invention.

The development of a bioreactor capable of the in vitro culture of true 3-dimensional segments of lung tissue is an important step in the development of clinically useful engineered lung tissue. For example, growth and maturation of the engineered lung tissue can take place in the bioreactor prior to implantation of the engineered lung into a recipient, thereby enhancing the functionality of the final implanted lung tissue in vivo. In addition, the bioreactor for in vitro lung culture can be used to assist the study of pulmonary biology, physiology, and development. That is, the interactions of lung endothelial and epithelial cells to form the alveolar-capillary barrier can be studied using the engineered lung tissue and bioreactor of the invention. A skilled artisan would be able to study lung behavior in a more controlled environment than the various animal models currently used. The engineered lung tissue and bioreactor could also be used for pharmacologic testing and investigation in human or animal tissue before proceeding to time-consuming and costly human or animal trials.

Compositions

Compositions of the invention include an engineered lung tissue. Preferably, the engineered lung tissue exhibits any one or more of the following properties: 1) vasculature and airway, where there is a patent, perfused vasculature and a patent airway tree that can be ventilated; 2) gas exchange, where the engineered lung is capable of exchanging sufficient gas between the airway and vascular compartments to support the physiological needs of the recipient; most preferably, the partial pressure of oxygen in the pulmonary vein is at least 50 mmHg; 3) mechanics, where the engineered tissue is strong enough to withstand all needed movements, in particular breathing motions and vascular perfusion, as well as manipulation during surgical implantation; 4) immunogenicity, where the engineered lung tissue does not provoke an immune response when implanted into the recipient.

The compositions and methods of the instant invention can be practiced using any suitable cell. Preferably, the suitable cell or cells are regenerative and can be used to recellularize the decellularized tissue of the invention. An example of a regenerative cells includes, but is not limited to, a stem cell, an embryonic stem cell, an adult stem cell, an umbilical cord blood cell, a tissue-derived stem or progenitor cells, bone marrow-derived step or progenitor cells, blood-derived stem or progenitor cell, a mesenchymal stem cells (MSC), a skeletal muscle-derived cells, a multipotent adult progenitor cell (MAPC), a fetal pulmonary cell, differentiated pulmonary epithelial cells, pulmonary progenitor cells, vascular progenitor cells, differentiated vascular cells and the like. Additional regenerative cells that can be used include bone marrow-derived stem cells such as bone marrow mononuclear cells (BM-MNC), endothelial or vascular stem or progenitor cells, and peripheral blood-derived stem cells such as endothelial progenitor cells (EPC).

Preferably, the suitable cell is isolated from a mammal, more preferably a primate and more preferably still, a human. The cells useful in the methods of the present invention are isolated using methods discussed herein, for example in the Examples section, or by any method known in the art. Following isolation, the suitable cells are cultured in a culture medium.

As a non-limiting example, neonatal pulmonary cells (NPCs) are described in more detailed with respect to culturing the cells. However, a skilled artisan will recognize that the culturing conditions can be modified to the suitable cell. Media formulations that support the growth of pulmonary cells include, but are not limited to, Minimum Essential Medium Eagle, ADC-1, LPM (bovine serum albumin-free), F10 (HAM), F12 (HAM), DCCM1, DCCM2, RPMI 1640, BGJ Medium (with and without Fitton-Jackson Modification), Basal Medium Eagle (BME—with the addition of Earle's salt base), Dulbecco's Modified Eagle Medium (DMEM—without serum), Yamane, IMEM-20, Glasgow Modification Eagle Medium (GMEM), Leibovitz L-15 Medium, McCoy's 5A Medium, Medium M199 (M199E—with Earle's salt base), Medium M199 (M199H—with Hank's salt base), Minimum Essential Medium Eagle (MEM-E—with Earle's salt base), Minimum Essential Medium Eagle (MEM-H—with Hank's salt base) and Minimum Essential Medium Eagle (MEM-NAA with nonessential amino acids), and the like.

Additional non-limiting examples of media useful in the methods of the invention may contain fetal serum of bovine or other species at a concentration at least 1% to about 30%, preferably at least about 5% to 15%, most preferably about 10%. Embryonic extract of bovine or other species can be present at a concentration of about 1% to 30%, preferably at least about 5% to 15%, most preferably about 10%.

Typically, the NPC culture medium comprises a base medium, serum and an antibiotic/antimycotic. One preferred base medium is DMEM/F12 (1:1). The preferred serum is fetal bovine serum (FBS) but other sera may be used, including horse serum or human serum. Preferably up to 20% FBS will be added to the above medium in order to support the growth of NPCs. However, a defined medium can be used if the necessary growth factors, cytokines, and hormones in FBS for NPC growth are identified and provided at appropriate concentrations in the growth medium. It is further recognized that additional components may be added to the culture medium. Such components include, but are not limited to, antibiotics, antimycotics, albumin, growth factors, amino acids, and other components known to the art for the culture of cells. Antibiotics which can be added into the medium include, but are not limited to, penicillin and streptomycin. The concentration of penicillin in the culture medium is about 10 to about 200 units per ml. The concentration of streptomycin in the culture medium is about 10 to about 200 µg/ml. However, the invention should in no way be construed to be limited to any one medium for culturing NPCs. Rather, any media capable of supporting pulmonary cells in tissue culture may be used.

In addition, the NPC culture medium can be supplemented with at least one growth factor. Preferably the growth factor is fibroblast growth factor (FGF). For example, any combination of FGF10, FGF7, FGF2 can be supplemented to the NPC culture medium. A preferred concentration of FGF7 is about 0.1-100 ng/ml (and any integer in between), more preferably the concentration is about 10 ng/ml. A preferred concentration of FGF10 is about 1-200 ng/ml (and any integer in between), more preferably the concentration is about 25 ng/ml. A preferred concentration of FGF2 is about 1-200 ng/ml (and any integer in between), more preferably the concentration is about 25 ng/ml.

Following isolation, NPCs may be incubated in culture medium, in a culture apparatus for a period of time or until the cells reach confluency before passing the cells to another culture apparatus. Following the initial plating, the cells can be maintained in culture for a period of about 6 days to yield the Passage 0 (P0) population. The cells may be passaged for an indefinite number of times, each passage comprising culturing the cells for about 6-7 days, during which time the cell doubling time can range between about 3 to about 5 days. The culturing apparatus can be of any culture apparatus commonly used in culturing cells in vitro.

NPCs may be cultured in culture medium supplemented with FGF in the for a period of time or until the cells reach a certain level of confluence. Preferably, the level of confluence is greater than 70%. More preferably, the level of confluence is greater than 90%. A period of time can be any time suitable for the culture of cells in vitro. NPC culture medium may be replaced during the culture of NPCs at any time. Preferably, the culture medium is replaced every 3 to 4 days. NPCs are then harvested from the culture apparatus whereupon they may be used immediately or cryopreserved to be stored for use at a later time. NPCs may be harvested by trypsinization, EDTA treatment, or any other procedure used to harvest cells from a culture apparatus.

NPCs described herein may be cryopreserved according to routine procedures. Preferably, about one to ten million cells are cryopreserved in culture medium containing 10% DMSO in vapor phase of liquid $N_2$. Frozen cells may be thawed by swirling in a 37° C. bath, resuspended in fresh growth medium, and expanded as described above.

The invention also provides cells that "seed" the scaffold. NPCs can be cultured on the scaffold. The cells can also differentiate in vitro by culturing the cells in differentiation medium. Alternatively, the cells can differentiate in vivo when they establish contact with a tissue within the mammal or when the cells are sufficiently close to a tissue to be influenced by substances (e.g., growth factors, enzymes, or hormones) released from the tissue. In other words, NPCs of the matrix can establish contact with a tissue, such as lung, by virtue of receiving signals from the tissue. Such signaling would occur, for example, when a receptor on the surface of a NPC, or on the surface of a cell descended from a NPC, binds and transduces a signal from a molecule such as a growth factor, enzyme, or hormone that was released by a tissue within the mammal. These agents guide differentiation so that the NPCs come to express some and possibly most (if not all) of the same proteins normally expressed by differentiated cells in the tissue in which they have been placed.

Alternatively, or in addition, NPCs of the matrix can be induced to differentiate by adding a substance (e.g., a growth factor, enzyme, hormone, or other signaling molecule) to the cell's environment. For example, a substance can be added to the biological scaffolding of the invention.

While NPCs and associated cellular matrix can eventually become fully differentiated, and while this is desirable in some circumstances (e.g., where the cells are used to recreate a histologically mature and complete tissue), not all of the cells administered need to be fully differentiated to achieve successful treatment; NPCs of the cellular matrix need only differentiate to a point sufficient to treat the mammal. That point can be reached either before or after the matrix is administered to the patient.

Differentiation occurs when a cell of the matrix expresses essentially the same phenotype as a mature cell at the site of implantation. For example, for the purpose of defining this invention, a NPC of a cellular matrix, having been implanted into the lung, is differentiated when it expresses essentially the same proteins expressed by the lung, e.g., an alveolar epithelial cell. Antibodies to lung markers are commercially available or otherwise readily attainable.

Differentiated cells can also be identified by their gross morphology and by the connections they form with other cells. For example, cells that differentiate into lung cells can develop complex morphology resembling bronchioles. For example, the invention is based on the novel discovery that culturing NPCs on a three dimensional scaffold can exhibit characteristics of mature lung cells.

The number of cells that is introduced into and onto a decellularized organ in order to generate an organ or tissue is dependent on both the organ (e.g., which organ, the size and weight of the organ) or tissue and the type and developmental stage of the regenerative cells. Different types of cells may have different tendencies as to the population density those cells will reach. Similarly, different organ or tissues may be cellularized at different densities. By way of example, a decellularized organ or tissue can be seeded with at least about 1,000 (e.g., at least 10,000, 100,000, 1,000,000, 10,000,000, or 100,000,000) regenerative cells; or can have from about 1,000 cells/mg tissue (wet weight, i.e., prior to decellularization) to about 10,000,000 cells/mg tissue (wet weight) attached thereto.

Cells can be introduced to a decellularized organ or tissue by injection into one or more locations. In addition, more than one type of cell (i.e., a cocktail of cells) can be introduced into a decellularized organ or tissue. For example, a cocktail of cells can be injected at multiple positions in a decellularized organ or tissue or different cell types can be injected into different portions of a decellularized organ or tissue. Alternatively, or in addition to injection, regenerative cells or a cocktail of cells can be introduced by perfusion into a cannulated decellularized organ or tissue. For example, cells can be perfused into a decellularized organ using a perfusion medium, which can then be changed to an expansion and/or differentiation medium to induce growth and/or differentiation of the regenerative cells. In the case of a lung tissue, the cells can be introduced into either or both of the airway compartment via the trachea, or the vascular compartment via the pulmonary artery or vein.

During recellularization, an organ or tissue is maintained under conditions in which at least some of the regenerative cells can multiply and/or differentiate within and on the decellularized organ or tissue. Those conditions include, without limitation, the appropriate temperature and/or pressure, electrical and/or mechanical activity, force, the appropriate amounts of $O_2$ and/or $CO_2$, an appropriate amount of humidity, and sterile or near-sterile conditions. During recellularization, the decellularized organ or tissue and the cells attached thereto are maintained in a suitable environment. For example, the cells may require a nutritional supplement (e.g., nutrients and/or a carbon source such as glucose), exogenous hormones or growth factors, and/or a particular pH.

Cells can be allogeneic to a decellularized organ or tissue (e.g., a human decellularized organ or tissue seeded with human cells), or regenerative cells can be xenogeneic to a decellularized organ or tissue (e.g., a pig decellularized organ or tissue seeded with human cells).

In some instances, an organ or tissue generated by the methods described herein is to be transplanted into a patient. In those cases, the cells used to recellularize a decellularized organ or tissue can be obtained from the patient such that the regenerative cells are autologous to the patient. Cells from a patient can be obtained from, for example, blood, bone marrow, tissues, or organs at different stages of life (e.g., prenatally, neonatally or perinatally, during adolescence, or as an adult) using methods known in the art. Alternatively, cells used to recellularize a decellularized organ or tissue can be syngeneic (i.e., from an identical twin) to the patient, cells can be human lymphocyte antigen (HLA)-matched cells from, for example, a relative of the patient or an HLA-matched individual unrelated to the patient, or cells can be allogeneic to the patient from, for example, a non-HLA-matched donor.

Irrespective of the source of the cells (e.g., autologous or not), the decellularized solid organ can be autologous, allogeneic or xenogeneic to a patient.

In certain instances, a decellularized tissue may be recellularized with cells in vivo (e.g., after the tissue has been transplanted into an individual). In vivo recellularization may be performed as described above (e.g., injection and/or perfusion) with, for example, any of the cells described herein. Alternatively or additionally, in vivo seeding of a decellularized organ or tissue with endogenous cells may occur naturally or be mediated by factors delivered to the recellularized tissue.

Genetic Modification

The present invention relates to the discovery that the decellularized tissues of the invention can be used to facilitate lung cell therapy in a mammal.

In another embodiment, decellularized lung tissue can be used to culture desired lung cells such as pulmonary epithelial cells. Whether genetically modified or not, the cells can be used to treat a lung disease including but not limited to emphysema, bronchiolitis obliterans, and cystic fibrosis. For example, the decellularized tissue of the invention can be used as a substrate for the culture of human pulmonary airway epithelial cells. The cultured human airway epithelial cells can then be delivered to a recipient via tracheal instillation, inhalation, or injection, among other ways. Such cells that are expanded in culture can be used to effect therapy in the recipient. The decellularized lung tissue (e.g., trachea) provides an outstanding platform for culturing and expanding the pulmonary epithelial cells, which are normally very difficult to grow in typical cell culture environment, such as tissue culture plastic.

In the context of gene therapy, the cells cultured on the decellularized tissue can be treated with a gene of interest prior to delivery of the cells into the lung of a recipient. In some cases, such cell-based gene delivery can present significant advantages of other means of gene delivery to the lung, such as inhalation of adenoviral gene delivery vectors. This superiority of cell-based gene delivery to a host stems from the observation that inhaled gene delivery vectors typically result in poor efficiency of cellular transduction, due to barriers imposed by the mucous layer and the host immune system. Delivery of a therapeutic gene that has been pre-inserted into cells avoids the problems associated with penetration of gene therapy vectors into recipient lung cells.

The decellularized lung tissue of the invention provides a convenient and efficient means to grow lung cells such as epithelial cells in a highly viable and differentiated state, as compared to culture on standard tissue culture plastic. In turn, the expansion of lung cells such as pulmonary epithelial cells on the decellularized matrix provides for a sufficiently large number of cells to be efficacious for cell therapy. In addition, the expansion of lung epithelial cells on the decellularized matrix provides a platform whereby cultured cells and be treated with gene therapy vectors in vitro. Cells that are transfected with a gene of choice in vitro can them be optionally purified to select for only those cells expressing the transgene of interest, and then introduced into a recipient in need of such cellular therapy. Such an approach could be of particular value in treating genetic lung diseases such as cystic fibrosis.

In one embodiment, the invention provides a method of treating cystic fibrosis. The method includes transfecting cells of interest such as epithelial cells with a normal version of the CFTR gene, a mutated version of which is the gene responsible for cystic fibrosis. Delivery of such transfected cells into a patient, either by instillation into the trachea, inhalation, or other means of introduction, alleviates the significant difficulties that have been associated with delivery of gene vectors into these patients. In this way, efficacious cellular therapy and gene delivery in cystic fibrosis may be realized. However, the invention should not be limited to only treating cystic fibrosis with cells transfected with the CFTR gene. Rather, the invention includes the treatment of any disease or disorder associated with lung cells.

Accordingly, the invention provides the use of genetically modified cells, such as pulmonary cells, that have been cultured on the decellularized tissue of the invention. Genetic modification may, for instance, result in the expression of exogenous genes ("transgenes") or in a change of expression of an endogenous gene. Such genetic modification may have therapeutic benefit. Alternatively, the genetic modification may provide a means to track or identify the cells so-modified, for instance, after implantation of a composition of the invention into an individual. Tracking a cell may include tracking migration, assimilation and survival of a transplanted genetically-modified cell. Genetic modification may also include at least a second gene. A second gene may encode, for instance, a selectable antibiotic-resistance gene or another selectable marker.

Proteins useful for tracking a cell include, but are not limited to, green fluorescent protein (GFP), any of the other fluorescent proteins (e.g., enhanced green, cyan, yellow, blue and red fluorescent proteins; Clontech, Palo Alto, Calif.), or other tag proteins (e.g., LacZ, FLAG-tag, Myc, His$_6$, and the like).

When the purpose of genetic modification of the cell is for the production of a biologically active substance, the substance will generally be one that is useful for the treatment of a given disorder. For example, it may be desired to genetically modify cells so that they secrete a certain growth factor product associated with bone or soft tissue formation. Growth factor products to induce growth of other, endogenous cell types relevant to tissue repair are also useful. For instance, growth factors to stimulate endogenous capillary and/or microvascular endothelial cells can be useful in repair of soft tissue defect, especially for larger volume defects.

The cells of the present invention can be genetically modified by having exogenous genetic material introduced into the cells, to produce a molecule such as a trophic factor, a growth factor, a cytokine, and the like, which is beneficial to culturing the cells. In addition, by having the cells genetically modified to produce such a molecule, the cell can provide an additional therapeutic effect to the mammal when transplanted into a mammal in need thereof. For example, the genetically modified cell can secrete a molecule that is beneficial to cells neighboring the transplant site in the mammal.

The pulmonary cells may be genetically modified using any method known to the skilled artisan. See, for instance, Sambrook et al. (2001, Molecular Cloning: A Laboratory Manual, Cold Spring Harbor Laboratory Press, Cold Spring Harbor, N.Y.), and in Ausubel et al, Eds, (1997, Current Protocols in Molecular Biology, John Wiley & Sons, New York, N.Y.). For example, a pulmonary cell may be exposed to an expression vector comprising a nucleic acid including a transgene, such that the nucleic acid is introduced into the cell under conditions appropriate for the transgene to be expressed within the cell. The transgene generally is an expression cassette, including a polynucleotide operably linked to a suitable promoter. The polynucleotide can encode a protein, or it can encode biologically active RNA (e.g., antisense RNA or a ribozyme). Thus, for example, the polynucleotide can encode a gene conferring resistance to a toxin, a hormone (such as peptide growth hormones, hormone releasing factors, sex hormones, adrenocorticotrophic hormones, cytokines (e.g., interferins, interleukins, lymphokines), etc.), a cell-surface-bound intracellular signaling moiety (e.g., cell adhesion molecules, hormone receptors, etc.), a factor promoting a given lineage of differentiation (e.g., bone morphogenic protein (BMP)), etc.

Within the expression cassette, the coding polynucleotide is operably linked to a suitable promoter. Examples of suitable promoters include prokaryotic promoters and viral promoters (e.g., retroviral ITRs, LTRs, immediate early viral promoters (IEp), such as herpesvirus IEp (e.g., ICP4-IEp and ICP0-IEEp), cytomegalovirus (CMV) IEp, and other viral promoters, such as Rous Sarcoma Virus (RSV) promoters, and Murine Leukemia Virus (MLV) promoters). Other suitable promoters are eukaryotic promoters, such as enhancers (e.g., the rabbit .beta.-globin regulatory elements), constitutively active promoters (e.g., the .beta.-actin promoter, etc.), signal specific promoters (e.g., inducible promoters such as a promoter responsive to RU486, etc.), and tissue-specific promoters. It is well within the skill of the art to select a promoter suitable for driving gene expression in a predefined cellular context. The expression cassette can include more than one coding polynucleotide, and it can include other elements (e.g., polyadenylation sequences, sequences encoding a membrane-insertion signal or a secretion leader, ribosome entry sequences, transcriptional regulatory elements (e.g., enhancers, silencers, etc.), and the like), as desired.

The expression cassette containing the transgene should be incorporated into a genetic vector suitable for delivering the transgene to the cells. Depending on the desired end application, any such vector can be so employed to genetically modify the cells (e.g., plasmids, naked DNA, viruses such as adenovirus, adeno-associated virus, herpesviruses, lentiviruses, papillomaviruses, retroviruses, etc.). Any method of constructing the desired expression cassette within such vectors can be employed, many of which are well known in the art (e.g., direct cloning, homologous recombination, etc.). The choice of vector will largely determine the method used to introduce the vector into the cells (e.g., by protoplast fusion, calcium-phosphate precipitation, gene gun, electroporation, DEAE dextran or lipid carrier mediated transfection, infection with viral vectors, etc.), which are generally known in the art.

Examples of techniques sufficient to direct persons of skill through in vitro amplification methods, including the polymerase chain reaction (PCR), the ligase chain reaction (LCR), and other DNA or RNA polymerase-mediated techniques are found in Sambrook et al., MOLECULAR CLONING: A LABORATORY MANUAL, volumes 1-3 ($3^{rd}$ ed., Cold Spring Harbor Press, NY 2001).

Once the nucleic acid for a protein is cloned, a skilled artisan may express the recombinant gene(s) in a variety of lung cells. It is expected that those of skill in the art are knowledgeable in the numerous expression systems available for expressing the desired transgene.

Present invention provides a engineered three dimensional tissue that mimics natural lung tissue. The capability to create composites and scaffolds that mimic natural lung tissue enables the repair and regeneration of tissues and collections of tissues to a greater degree than prior art methods, and exhibits more accurate histological structure and function than can be achieved using prior art methods. For example, the engineered lung tissue comprises cells that exhibit budding structures and elongating tubular structures. Furthermore, the cells express genes involved in morphogenesis and lung epithelial differentiation. Non-limiting genes involved in morphogenesis and lung epithelial differentiation include distal epithelial marker genes SpC and SpB, the mesenchymal-derived morphogen FGF10, FGFr2, and vascular endothelial growth factor A (VEGF).

Administration

The invention contemplates use of the engineered tissues in both in vitro and in vivo settings. Thus, the invention provides for use of the engineered tissues for research purposes and for therapeutic or medical/veterinary purposes. In research settings, an enormous number of practical applications exist for the technology. One example of such applications is use of the engineered tissues in an ex vivo cancer model, such as one to test the effectiveness of various ablation techniques (including, for example, radiation treatment, chemotherapy treatment, or a combination) in a lab, thus avoiding use of ill patients to optimize a treatment method. For example, one can attach a recently removed lung to a bioreactor and treat the lung to ablate tissue. Another example of an in vivo use is for tissue engineering.

The engineered tissues of the present invention have use in vivo. Among the various uses, mention can be made of methods of in vivo treatment of subjects (used interchangeably herein with "patients", and meant to encompass both human and animals). In general for certain embodiments, methods of treating subjects comprise implanting an engineered tissue according to the invention into or on the surface of a subject, where implanting of the tissue results in a detectable change in the subject. The detectable change can be any change that can be detected using the natural senses or using man-made devices. While any type of treatment is envisioned by the present invention (e.g., therapeutic treatment of a disease or disorder, cosmetic treatment of skin blemishes, etc.), in many embodiments, the treatment is a therapeutic treatment of a disease, disorder, or other affliction of a subject. As such, a detectable change may be detection of a change, preferably an improvement, in at least one clinical symptom of a disease or disorder affecting the subject. Exemplary in vivo therapeutic methods include regeneration of organs after treatment for a tumor, preparation of a surgical site for implantation of a medical device, skin grafting, and replacement of part or all of a tissue or organ, such as one damaged or destroyed by a disease or disorder. Exemplary organs or tissues include: heart, lung, liver, kidney, urinary bladder, brain, ear, eye, or skin. In view of the fact that a subject may be a human or animal, the present invention has both medical and veterinary applications.

In one embodiment, the method comprises exposing a tissue to the decellularization methods of the invention to kill cells of the treated tissue and to create a tissue scaffold. The method can further comprise seeding the tissue scaffold with cells, and allowing the seeded cells to proliferate in and on the tissue scaffold. Proliferation produces a regenerated tissue that contains healthy and functional cells.

The invention also provides methods of treating a patient by implanting an engineered lung tissue into a mammal in need thereof. In some instances, the engineered lung tissue comprises suitable cells, for example NPCs. However, the invention should not be limited to any particular type of cells. After implantation, the grafted cells can respond to environmental cues that will cause it to develop characteristics of the endogenous tissue. Preferably, the cells form histiotypic alveolar-like structures, comprised of differentiated distal epithelial cells (proSpC expressing) forming ductal structures. Thus, the implanted cells will develop characteristics that liken it to the surrounding tissue. Using these methods, the biological scaffolding can augment the tissue; the biological scaffolding of the invention can be used for tissue engineering and in any conventional tissue engineering setting.

Accordingly, the invention encompasses tissue regeneration applications. The objective of the tissue regeneration therapy approach is to deliver high densities of repair-competent cells (or cells that can become competent when influenced by the local environment) to the defect site in a format that optimizes both initial wound mechanics and eventual neotissue production. The composition of the instant invention is particularly useful in methods to alleviate or treat lung tissue defects in individuals. Advantageously, the composition of the invention provides for improved lung tissue regeneration. Specifically, the tissue regeneration is achieved more rapidly as a result of the inventive composition.

Advantageously, the compositions and methods of the invention represent an improvement over prior art methods. Preferably the composition for use in treating a lung tissue defect comprises NPCs, more preferably NPCs seeded on a scaffold and cultured in vitro to generate a 3-dimensional culture, as described elsewhere herein.

Model for Drug Discovery

The present invention provides an in vitro method suitable to allow evaluation of test compounds for therapeutic activity with respect to a pulmonary disease or disorder. Preferably, the method includes the use of an engineered three dimensional lung tissue.

The invention is based on a model developed using decellularized tissue. In some instances, the decellularized tissue can be seeded with suitable cells. In some instances, mixed populations of NPC which contain epithelial, mesenchymal, and endothelial cells are used to generate the three dimensional engineered lung tissue. For example, the NPCs are placed within a three dimensional decellularized lung tissue. Thus, the model incorporates the influence of NPC on the growth and cell-cell communication with neighboring cells. The three dimensional lung tissue mimics a natural lung tissue, for example the engineered lung tissue exhibits branching morphogenesis exemplified by natural lung tissue.

The model is useful for testing drugs on the pathology of a lung tissue. In addition, the model can be used to examine the effects of particular delivery vehicles for therapeutic agents on the pathology of lung tissue, for example, to compare the effects of the same agent administered via different delivery systems, or simply to assess whether a delivery vehicle itself (e.g. a viral vector) is capable of affecting lung pathology.

In one embodiment, the invention provides an in vitro method for screening a test agent for the ability of the test agent to modulate the health of a lung tissue. The method comprises contacting a test agent to an engineered three dimensional lung tissue model and measuring the effect that the test agent has on the lung tissue model. Any alteration to the model in the presence of the test agent is an indication that the test agent is able to modulate the health of a lung tissue.

In another embodiment, the present invention provides an in vitro method for observing an effect a test agent has on a lung tissue, comprising the steps of:
a) providing at least one three-dimensional lung tissue model, wherein the model is intended to model normal lung tissue;
b) contacting the test agent with the lung tissue model; and
c) observing the effect the test agent has the lung tissue model.

The tissue model is a construct which comprises a three-dimensional array of cells on a scaffold, for example a collagen matrix, and at least one test cell. The method comprises observing the effect of the test agent on the pathology of the lung tissue. However the method may further comprise the step of observing the effect of the test agent on individual cell types of the lung tissue.

The test agent may be any agent including chemical agents (such as toxins), pharmaceuticals, peptides, proteins (such as antibodies, cytokines, enzymes, etc.), and nucleic acids, including gene medicines and introduced genes, which may encode therapeutic agents such as proteins, antisense agents (i.e. nucleic acids comprising a sequence complementary to a target RNA expressed in a target cell type, such as RNAi or siRNA), ribozymes, etc. Additionally or alternatively, the test agent may be a physical agent such as radiation (e.g. ionizing radiation, UV-light or heat); these can be tested alone or in combination with chemical and other agents.

The model may also be used to test delivery vehicles. These may be of any form, from conventional pharmaceutical formulations, to gene delivery vehicles. For example, the model may be used to compare the effects on a therapeutic effect of the same agent administered by two or more different delivery systems (e.g. a depot formulation and a controlled release formulation). It may also be used to investigate whether a particular vehicle-could have effects of itself on the lung tissue. As the use of gene-based therapeutics increases, the safety issues associated with the various possible delivery systems become increasingly important. Thus the models of the present invention may be used to investigate the properties of delivery systems for nucleic acid therapeutics, such as naked DNA or RNA, viral vectors (e.g. retroviral or adenoviral vectors), liposomes, etc. Thus the test agent may be a delivery vehicle of any appropriate type with or without any associated therapeutic agent.

The test agent may be added to the model to be tested using any suitable means. For example, the test agent may be added drop-wise onto the surface of the model and allowed to diffuse into or otherwise enter the model, or it can be added to the nutrient medium and allowed to diffuse through the collagen gel. The model is also suitable for testing the effects of physical agents such as ionizing radiation, UV-light or heat alone or in combination with chemical agents (for example, in photodynamic therapy).

Observing the effect the test agent has on the model can be accomplished using a variety of methods. For example, a particular agent may induce a cell to enter apoptosis. Detectable changes in the cell may comprise changes in cell area, volume, shape, morphology, marker expression (e.g. cell surface marker expression) or other suitable characteristic, such as chromosomal fragmentation. Cell number may also be monitored in order to observe the effects of a test agent on cell proliferation; this may be analyzed directly, e.g. by counting the number of a particular cell type present, or indirectly, e.g. by measuring the size of a particular cell mass. These may be observed directly or indirectly on the intact model using, for example, suitable fluorescent cell staining. This can be by pre-labeling of cells with vital dyes or genetically introduced fluorescent markers (for example green fluorescent proteins) for serial analysis of the living model or by fixation and post-labeling with fluorescent substances such as propidium iodide or fluorescently labeled antibodies. Alternatively, models may be processed by normal histological methods, such as immunohistochemistry, using antibodies directed against a suitable cellular target, or in situ hybridization, to test for expression of a particular mRNA species. Moreover, this may be carried out in an automated/robotic or semi-automated manner, using computer systems and software to image the cells at various time points and detect any change in, for example, cell density, location and/or morphology. Confocal laser scanning microscopy in particular permits three-dimensional analysis of intact models. Thus it is possible to apply directly to the intact, three-dimensional lung tissue model, quantitative analysis of cell behavior which are normally only possible for cells in conventional two-dimensional culture. By this means quantitative, serial analysis of cell proliferation, apoptosis, necrosis, migration and matrix invasion, among others, are obtained in a three-dimensional lung tissue model which bridges the gap between conventional two-dimensional cell cultures and live animal models.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Example 1: Decellularization of Rat Lung and Morphological Characterization of Decellularized Scaffolds A decellularized organ offers several advantages for use as a tissue engineering scaffold. In one aspect, the decellularized scaffold contains the appropriate 3-dimensional organization required for tissue function, including a vascular system and airway network in the case of lung. In addition, extracellular matrix (ECM) components are widely conserved across species, thus reducing the likelihood of a decellularized scaffold inducing an immune response upon xenogeneic implantation [Bernard et al., 1983, Biochemistry 1983; 22:5213-23]. In another aspect, native ECM offers the optimal substrate for cell attachment, spreading, growth and differentiation.

The goal of the decellularization process of the present invention is to remove cellular and nuclear material while retaining key aspects of and minimizing any damage to the ECM of the lung. The results presented herein demonstrate that native lung tissue can be decellularized to remove cellular components and antigenic molecules, yet retain key extracellular matrix molecules. In one aspect, a goal of the decellularization process of the invention is to generate a decellularized lung scaffold that is fully compatible with cell culture and at the same time provide a barrier function. In addition, it is desirable for the decellularized lung scaffold to have an intact airway tree and vascular network.

A chemical methodology for decellularization was used in the present study. The chemicals used in this study included sodium chloride, CHAPS, and EDTA. A hypertonic sodium chloride solution can efficiently lyse cells, although it does not assist in removing cellular components from the tissue. CHAPS is a zwitterionic detergent, which allows efficient solubilization and thus removal of cellular material. EDTA is a chelating agent that binds key divalent ions (i.e. $Ca^{2+}$) that aids in disrupting cell attachment to the ECM. In addition, the solution is of high alkalinity, which helps solubilize cytoplasmic cellular components as well as GAGs which otherwise clog the matrix [Gilbert et al., 2008 J Surg Res 152(1):135-9].

The materials and methods employed in these experiments are now described.

Materials and Methods

Organ Harvest

Lungs were harvested from young adult (3 month-old) male Fischer 344 rats. All animal experimental work was performed with approval from the Yale University Institutional Animal Care and Use Committee. Animals were anesthetized via intraperitoneal injection of sodium pentobarbital (Sigma, 40 mg/kg). After induction of anesthesia, the abdomen was entered via a transverse incision just below the costal margin. The diaphragm was punctured, and the rib cage was cut to reveal the lungs. The lungs were perfused via the right ventricle with PBS containing 50 U/ml heparin (Sigma). After perfusion was complete, the heart, lungs and trachea were dissected free and removed en bloc.

Bioreactor Components

Bioreactor components were obtained from Cole-Parmer (Vernon Hills, Ill.). A silicone stopper and 500 ml glass jar formed the basis of the bioreactor. PharMed tubing (Westlake, Ohio), sizes L/S 14 and L/S 16, was inserted through the silicone stopper to enable the necessary connections to the lung, including a perfusion loop and air ventilation. Pressure was monitored using a TruWave pressure transducer (Edwards Lifesciences, Irvine, Calif.) between the perfusion pump and the connection to the pulmonary artery. Perfusion was accomplished using a Masterflex L/S variable speed roller pump (Masterflex, Vernon Hills, Ill.).

Decellularization Process

Fluid used for decellularization was 8 mM CHAPS, 1M NaCl, 25 mM EDTA in PBS. All chemicals were obtained from Sigma, and PBS was obtained from Gibco. The bioreactor was filled with decellularization fluid, and the bioreactor was transferred to an incubator kept at 37° C. The perfusion pressure was monitored at the inflow to the pulmonary trunk and kept below 30 or 20 mmHg. The decellularization fluid was replaced with fresh fluid at the following time points: 30 min, 1 hour, 2 hours, 4 hours, 6 hours. For most conditions, decellularization was stopped after 4 or 6 hours.

DNA Assay

DNA content of tissues was quantified using the Quant-iT PicoGreen dsDNA assay kit (Invitrogen, Eugene, Oreg.), following manufacturer's instructions. Briefly, tissue samples were weighed and lyophilized, diluted in TE buffer and mixed with the Quant-iT PicoGreen reagent. Fluorescence was measured at 535 nm with excitation at 485 nm, and DNA content was quantified using a standard curve. At least 4 samples were measured for both native and decellularized samples.

Western Blot

Tissues for Western blotting were digested in cold RIPA buffer (Boston Bioproducts) with added protease inhibitors (Sigma) and homogenized at 15,000 rpm for 30 seconds. After incubation for 1 hour at 4° C., insoluble particles were removed by centrifugation at 14,000 g for 25 min. Protein concentration was quantified via Bradford assay [Bradford, 1976, Anal Biochem 72:248-54], then boiled in Laemmli's reducing buffer (Boston Bioproducts) for 25 min at 65° C. Samples were stored at −80° C. until analysis. Samples were run on variable percent polyacrylamide gels, using 25-30 µg of protein. After electrophoresis, protein was transferred to a nitrocellulose membrane. Membranes were rinsed in TBS, then blocked for 1hour in 5% non-fat dry milk (NFDM) or 3% bovine serum albumin in TBS with 0.05% tween-20 (TBS-T). Primary antibodies were applied overnight in 2% NFDM or 3% BSA in TBS-T. Secondary antibodies were from Santa Cruz and were raised in either donkey or goat, and were applied for 1 hour at room temperature at a dilution of 1:2000. Protein was detected using substrate from Supersignal West Pico, which was applied for 5 minutes before film development.

Immunofluorescence

Tissue blocks were fixed for 4 hours in 3.7% formaldehyde (Sigma), then transferred to 70% ethanol and embedded in paraffin. Thin (5 µm) sections were prepared by the Yale University Histology core facility. Tissue sections were deparaffinized in xylene, rehydrated through an ethanol gradient, and rinsed in buffer (PBS+0.2% triton-X) for 15 minutes. Antigen retrieval was performed in 0.01M citric acid, pH 6.0, at 70° C. for 20 minutes. After cooling to room temperature, sections were rinsed in buffer, then blocked in PBS with 5% bovine serum albumin (BSA) and 0.75% glycine for 1 hour at room temperature. Primary antibodies were applied at the appropriate concentrations in blocking buffer overnight at 4° C. Slides were rinsed 3 times in buffer and then secondary antibodies were applied at 1:500 dilution in blocking buffer for 1 hour at R.T. Secondary antibodies were AlexFluor 555 donkey anti-goat or goat anti-rabbit and AlexaFluor 488 chicken anti-rabbit, obtained from Invitrogen. Slides were mounted using DAPI-containing mounting media (Vector Labs), and images acquired using a Zeiss Axiovert 200M inverted fluorescent microscope.

Scanning Electron Microscopy

Samples were fixed using 2% glutaraldehyde and 2.5% paraformaldehyde in 0.1M cacodylate buffer (EMD Biosciences, Gibbstown, N.J.) for 2 hours at room temperature, then rinsed in cacodylate buffer, sliced, and dehydrated through an ethanol gradient. Samples were further dehydrated in hexamethyldisilizane for 10 min and dried overnight, then sputter coated with gold and analyzed using a JOEL JXA-8600 at the Yale University Geology and Geophysics facility.

Transmission Electron Microscopy

Samples were fixed using 4% paraformaldehyde in PBS and then placed in 2% glutaraldehyde and 2.5% paraformaldehyde in 0.1M sodium cacodylate buffered fixative (pH 7.4) for 2 hours at room temperature. The samples were rinsed 3 times in 0.1M sodium cacodylate buffer and post-fixed in 1% osmium tetroxide for 1 hour, then en bloc stained in 2% uranyl acetate in maleate buffer pH 5.2 for a further hour. Then, the samples were rinsed, dehydrated through a graded ethanol series and infiltrated with epon resin and baked overnight at 60° C. Hardened blocks were cut using a Leica UltraCut UCT and 60 nm sections were collected on nickel grids and stained using 2% uranyl acetate and lead citrate. Samples were viewed on a FEI Tencai Biotwin TEM at 80 kV. Images were taken using a Morada CCD digital camera using iTEM (Olympus) software.

Microsphere Retention

Decellularized or native lungs were attached to cannulae as described elsewhere herein, and the lung was inflated via the trachea with PBS containing 5 µm microspheres. The vasculature was then flushed with 3 rinses of 10 ml PBS. Microspheres were washed twice in $dH_2O$ to remove debris and lyse any cells that would otherwise affect the native lung readings. Using a Coulter counter set to measure particles between 4.9 µm and 5.1 µm, the microsphere concentration in each sample was quantified and compared to a baseline reading taken before microsphere injection.

Micro CT Imaging

Native or decellularized lungs were fixed in 10% neutral buffered formalin (Sigma) and injected with contrast agent through either the airway or vasculature. Contrast agent was 20% bismuth and 5% gelatin (Sigma) in PBS. After injection of contrast, the lung was cooled in an ice bath to polymerize the gelatin.

For the whole lung, the pulmonary vasculature was imaged with a micro-CT imaging system (GE eXplore Locus SP, GE Healthcare), set to a 0.029-mm effective detector pixel size. The micro-CT was operated at 60 kV peak x-ray tube voltage, 80 mA tube current, 1600 millisecond per frame, 22 detector binning model, 720 views, and 0.5o increments per view. For the high resolution imaging of one lobe (right superiorlobe), samples were positioned on a computer-controlled rotation stage and scanned 360 around the vertical axis in rotation steps of 0.4°. The tube is operated at an 80 kV peak and 80 mA. The exposure time for each view was typically 3000 millisecond, with detector binning model set to 1×1 and resolution of 0.0065 mm. Both acquisitions resulted in a set of contiguous axial VFF-formatted images through the lung or one lobe.

With the use of Microview Software (GE Healthcare), the raw data was corrected and reconstructed with voxels of dimensions 58 µm×58 µm×58 µm to visualize the whole vascular tree in the lung. For the high-quality of the vascular tree (one lobe), voxels of dimensions was set to 6.5 µm×6.5 µm×6.5 µm. This software was also used to reconstruct maximum intensity projection images from the raw data.

Multiplanar reformation, spatial filtering, and volume rendering techniques allowed for the data set to be viewed in transverse, sagittal, coronal, hybrid planes, and 3D format. Binarized images were used for object extraction and region-of-interest measurements. Three-dimensional volume images are reconstructed from the angular views by using a modified Feldkamp filtered back-projection algorithm. However, with this system, an entire rat lung (field of view, approximately 3.0 cm) may be studied, with images having typical cubic voxel dimensions as small as 58 µm. The opacity of each voxel is represented by a 16-bit grayscale value.

The results of the experiments are now described.

Decellularization Method

The results presented herein demonstrate a decellularization method that removes cellular material from complete lobes of intact rodent lungs. It was observed that that decellularization using 1M NaCl, 8 mM CHAPS and 25 mM EDTA was optimal to remove cellular material and yet did not appear to remove collagen or elastin fibers (based on histology) or damage the structural integrity of the matrix (based on mechanical testing). In comparison, decellularization with solutions containing SDS were found to damage the mechanical strength of the matrix. Other conditions were found to either not efficiently remove cellular material or cause significant declines in the matrix integrity.

Histological Analysis

Histology was used to characterize many decellularized lung scaffolds. Based on H&E staining and DAPI-staining for nuclei and DNA, the decellularized lungs did not show a single intact cell. On occasion, unwound DNA or cellular antigen was observed, but intact cells were not observed. FIGS. 1A-C demonstrates H&E staining of native and decellularized lung, while FIGS. 2A-B shows DAPI-staining for remnant DNA. Preservation of the pulmonary structure was also observed based on the fact that alveolar septae appeared intact on standard histological sections, as do the larger airways and blood vessels.

DNA Content

The complete removal of cellular material is important for several reasons. First, if the scaffold is intended to be used for tissue engineering applications, one must be certain that all the cells from the scaffold are removed before seeding the scaffold with a new cell source. In addition to complicating the evaluation of the reseeded scaffolds, any remaining cellular material would cause immune complications if the engineered tissue is used for in vivo applications [Conconi et al., 2005, Transpl Int 18:727-34; Macchiarini et al, 2008, Lancet 372(9655):2023-30; Alexander et al., 2009, Cell Transplant 18:255-9]. As a result, the scaffold of the present invention has been confirmed that both MHC Class I and II antigens are not present in the decellularized scaffolds. Second, in order to evaluate separately the contributions of the extracellular matrix to lung mechanics, all cellular components should be removed. The two classes of components that can contribute to peripheral lung mechanics are cellular material and the extracellular matrix. Extracellular matrix can be further divided primarily into collagen, elastin, and proteoglycans [Cavalcante et al., 2005, J Appl Physiol 98:672-9; Dunsmore et al., 1996, Am J Physiol 270:L3-27; Ito et al., 2005, J Appl Physiol 98:503-11; Suki et al., 2005, J Appl Physiol 98:1892-9]. By ensuring removal of cellular components from the decellularized scaffolds, mechanical properties of the scaffold can be assessed.

In order to document removal of cellular material, a quantitative DNA assay was performed. A drastic reduction in DNA content in decellularized scaffolds compared to native lung was observed (FIG. 1C). Decellularized scaffolds contained approximately 1.2% of the DNA found in native lung, which corresponded to 1.83±0.29 ng of DNA per mg dry weight. This compares to 38.7±5.8 ng/mg for native lung. While extensive rinsing of the scaffolds can be generally used to minimize remnant DNA, complete removal of all DNA was difficult and small amounts of DNA remained, as demonstrated by DAPI stains showing small clusters of unwound DNA in FIGS. 2A-B. The drastic reduction in DNA content was indicative of cellular removal, and together with the histological findings confirmed that all viable cellular material was absent from the scaffolds.

In the decellularized scaffolds, it has been demonstrated that almost 99% of DNA has been removed. A small amount of DNA remains in the matrix, but is present as elongated strands of DNA, as shown in FIGS. 2A-B. It has been observed that no organization of this remnant DNA in nuclear structures, based on DAPI staining.

It has been observed that removal of 98.8% of DNA compared to native lung, with a remaining DNA concentration of 1.83 ng DNA per mg of tissue (dry weight). This compares favorably to levels of 16.6 ng/mg remnant DNA seen by others for decellularized heart tissue [Ott et al., 2008, Nat Med 14:213-21], especially considering that level is standardized to wet weight, not dry weight as in this and other studies [Gilbert et al., 2008 J Surg Res 152(1):135-9]. However, the levels of remnant DNA observed are higher than those seen for commercially available and laboratory produced ECM scaffolds used for skin grafts, where most scaffolds show less than 0.2 ng DNA per mg dry weight, although some scaffolds had as much as 1.13 ng/mg remnant DNA [Gilbert et al., 2008 J Surg Res 152(1):135-9].

Immunogenicity

Figure 3:
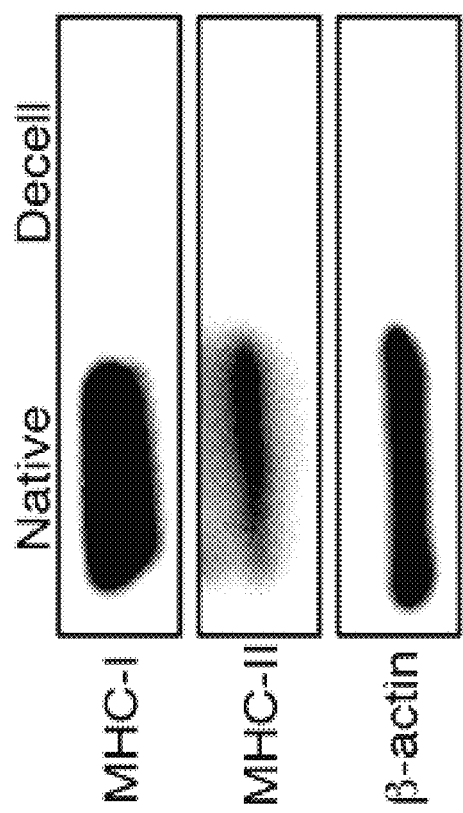
FIG. 3 is a Western blot for MHC Class I and II antigen, demonstrating lack of MHC Class I or II antigen in decellularized scaffolds.
Figure 7:
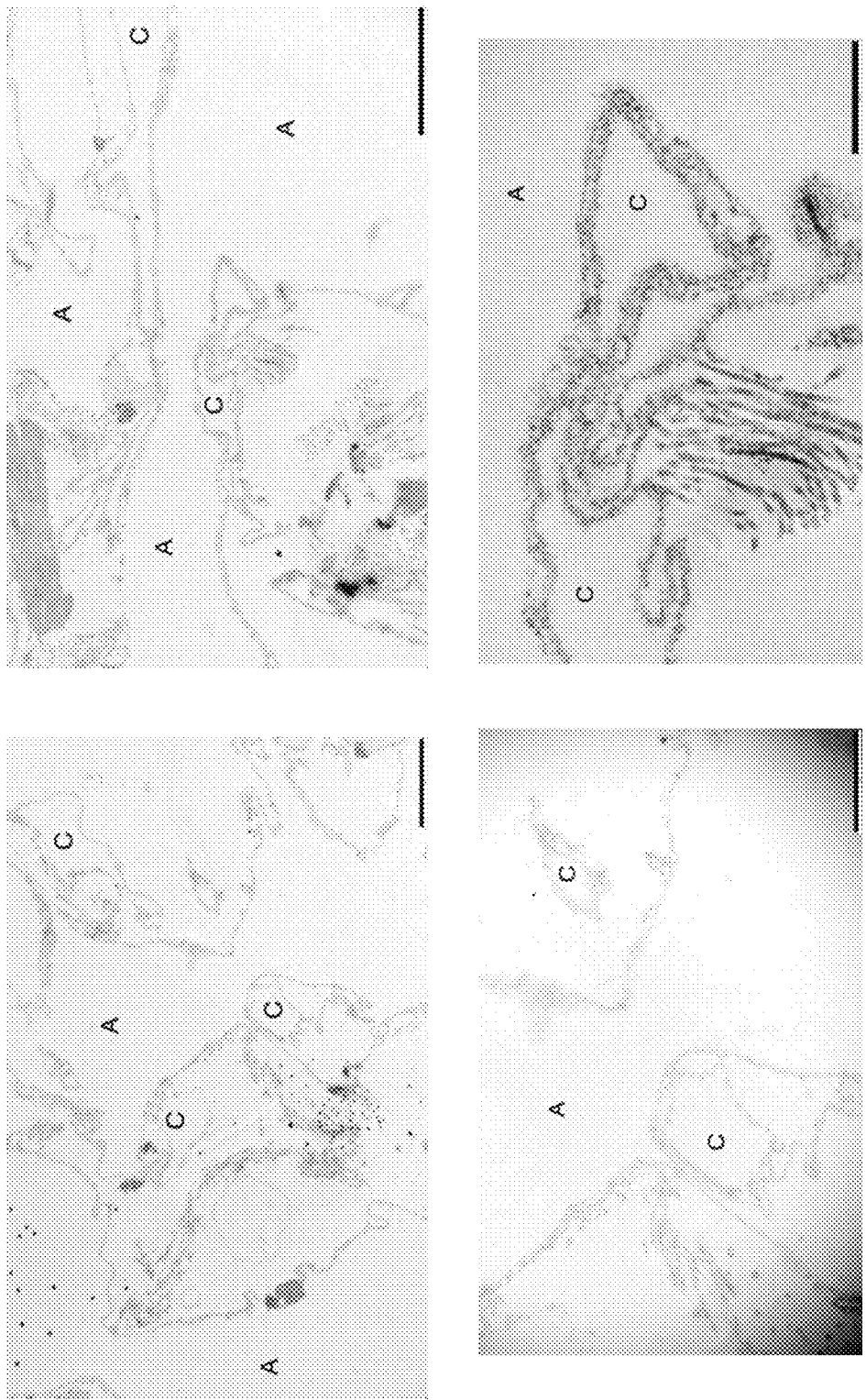
FIG. 7 is an image depicting transmission EM of decellularized lung demonstrating preserved capillaries. Perfusion pressure for decellularization was less than 20 mmHg. C indicates capillaries, while A indicates alveoli. Dimensions of alveoli and capillaries appear smaller than occur in vivo, due to compression of the decellularized matrix. Scale bars are 2 μm on top panels, 1 μm on bottom left panel, and 500 nm on bottom right panel.

Immunogenicity of the decellularized scaffolds were characterized by staining for Major histocompatibility complex (MHC) Class I and II antigens. MHC class I and II proteins are membrane glycoproteins that are important in the antigen-specific immune response. MHC Class I antigen is expressed on all nucleated cells, while MHC Class II antigen is found on specialized cells of the immune system. MHC Class I antigens allow an organism to recognize 'self' from 'non-self', and are thus important to remove from the decellularized scaffold in order to avoid immune problems upon future implantation of engineered lung tissue into an animal model. FIG. 3 depicts Western blotting results for MHC Class I and II antigen as well as β-actin. Complete loss of both MHC Class I and II antigens was observed by immunoblotting, confirming that the decellularized scaffolds would not be expected to provoke a significant immune response if used for tissue engineering applications. β-actin was also lost, consistent with the absence of cellular material. It is believed that the scaffolds are unlikely to provoke an immune response if implanted into a host.

Extracellular Matrix Characterization

Collagen: Collagen is the most important structural component of the lung, being principally responsible for the overall mechanical strength of the tissue. Immunofluorescence was used to characterize the distribution of collagens I and IV in native and decellularized lung, as shown in FIGS. 4A-B. Both collagen I and IV are retained by the decellularized matrix, with collagen I noted principally around the larger airways and vasculature, and collagen IV noted throughout the parenchyma. Similar staining patterns were noted for both native and decellularized lung. The preservation of these collagen subtypes in their anatomically appropriate locations may enable the selective deposition of cell types during the development of engineered lung tissue.

Scanning EM Evaluation of Decellularized Scaffolds

Scanning electron microscopy (SEM) was used to evaluate the microstructure of the decellularized lung scaffolds. FIGS. 5A-B shows sample images, demonstrating cellular removal yet overall maintenance of alveolar architecture. The alveoli in decellularized lungs appeared slightly deflated, which is an artifact of fixation. Native lung was fixed by inflating the lung with fixative; the decellularized lung, however, cannot contain the fixative fluid within the alveolar compartment when pressurized, thus giving the lung a deflated appearance. However, there is a general similarity in alveolar architecture with preservation of the alveolar septae. These results, together with findings from histology studies, indicate that the overall pulmonary airway architecture and alveolar structure, including alveolar septae, were intact in the decellularized scaffolds.

Impact of Perfusion Pressure on Scaffold Ultrastructure

In addition to the scanning EM studies, transmission EM (TEM) was used to study the capillary-alveolar basement membrane. This is a critical feature of the decellularized scaffolds as the presence of an intact capillary network allows the decellularized scaffold to resist macromolecular transit into the alveolar spaces and also provides a suitable substrate for the growth of capillary endothelium in engineered lung tissues.

FIGS. 5A and 5B depict TEM images of native lung and lung that was decellularized without control of vascular perfusion pressures. Under such conditions, the alveolar basement membrane was at times not identifiable and no capillaries could be found. Without wishing to be bound by any particular theory, it is believed that damage to the basement membrane and ultrastructure could be reduced by minimizing the perfusion pressures during the decellularization process and maximally vasodilating the vasculature before beginning decellularization. Although the decellularization fluid was perfused through the vasculature at subphysiologic flow rates, vascular perfusion pressure can become supraphysiologic during decellularization due to massive cell lysis and buildup of cellular protein and DNA in the vasculature. Therefore the pulmonary arterial pressure was carefully monitored and the decellularization bioreactor and perfusion rate was modified in order to keep this pressure strictly below ~20-30 mmHg. The vasodilator sodium nitroprusside was utilized to minimize the initial perfusion pressures.

FIG. 6C shows TEM images of scaffolds decellularized with pressures kept below ~30 mmHg. Under these conditions, an intact, continuous alveolar basement membrane was observed. Collagen fibers and other matrix components are retained within the alveolar septae. However, we do not notice the presence of any clear capillary structures, which should be present in abundance surrounding the alveoli.

Retention of Capillary Structures in Decellularized Scaffolds

Figure 8:
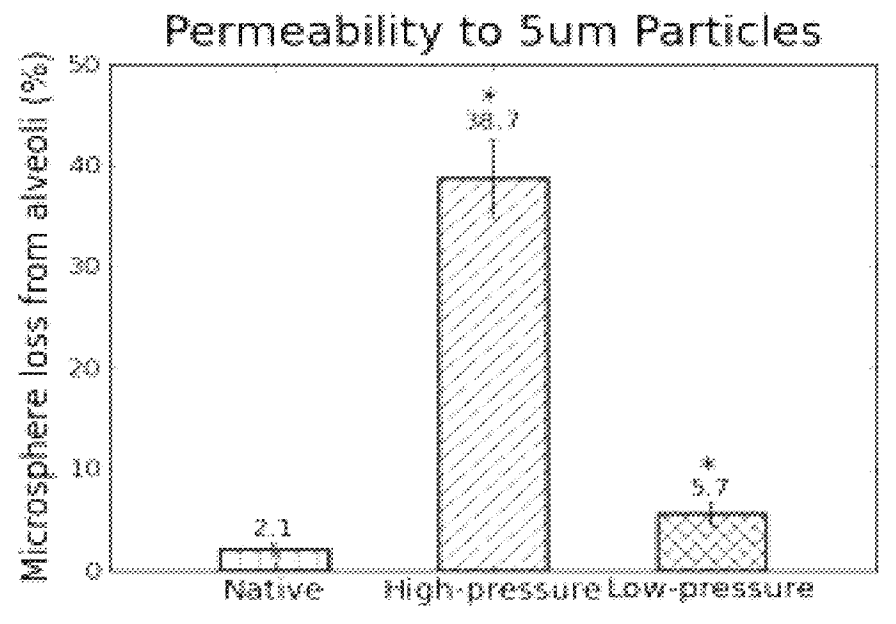

The typical pressure in the pulmonary vascular system of the rodent is less than 15 mmHg [Lee et al., 1999, Cell 99:301-12], significantly lower than the 30 mmHg utilized in the above studies. Despite reducing the perfusion flow rate and using a vasodilator to lower perfusion pressures, it was difficult to maintain the decellularization perfusion pressure below 30 mmHg. However, it was discovered that a slight modification in the decellularization protocol enabled perfusion during decellularization at pressures less than ~20 mmHg. Of significance, this enabled the retention of capillary structures. This modification encompassed lavaging the airway compartment with decellularization fluid before beginning perfusion of the decellularization fluid through the vasculature. The result was the significant lowering of the vascular perfusion pressure, especially at the beginning of the decellularization process. As shown in FIG. 8, this technique enabled the retention of capillary structures in the decellularized scaffolds. It is believed that the retention of capillaries is a significant development in the creation of decellularized lung scaffolds.

The scaffold should retain an intact airway tree and vascular network. Using scanning and transmission electron microscopy in addition to micro-CT imaging, it has been demonstrated that, overall, the scaffold is remarkably well preserved after the decellularization process. Scanning EM, as well as routine histology, demonstrated that the scaffold was grossly intact without large defects (i.e. alveoli and alveolar septae appear intact). Transmission EM demonstrated that the alveolar basement membrane was well preserved and that at least some capillaries were retained. Micro-CT imaging demonstrated that the vasculature was intact down to vessels of 100 µm diameter.

Permeability Assessment

In order for a lung to function in vivo, it must possess a continuous, patent and non-leaky vasculature in order to avoid massive blood loss into the alveolar and interstitial spaces. The ability of decellularized lung scaffolds to retain 5 µm microspheres in the airway compartment, without allowing transport of these macromolecules into the vasculature was evaluated. Five µm particles were use in order to mimic the size of red blood cells, the principle component of blood, which would need to be retained in the vasculature. Therefore, the leak of 5 µm particles out of the airway and into the vasculature was evaluated, with the assumption that there was no significant directionality to the movement of such particles across a decellularized membrane.

The permeability of native lungs, lungs decellularized with uncontrolled perfusion pressures (constant perfusion flow rate), and lungs decellularized after vasodilation and with controlled perfusion pressures (less than 30 mmHg) was determined. The results are shown in FIG. 8, and confirmed the TEM findings on a larger scale. It was observed that decellularization with high (uncontrolled) perfusion pressure lead to a 39% leak, compared to 5.7% for low-pressure decellularization and 2.1% for native lung.

Micro-CT Imaging

Micro-CT imaging was used to evaluate the patency of the airway and vascular compartments of decellularized lung scaffolds. This technique allows obtaining 3-dimensional images of the lung scaffolds, and facilitate the identification of the degree of patency of the airway and vascular compartments.

FIGS. 9A-B shows images of the vasculature, with resolution of 58 µm. At this resolution, the large vessels are shown to be intact (top panels of FIGS. 9A-B), and the native and decellularized samples are generally similar, shown in the lower and middle panels. Higher resolution images (6.8 µm) of the vasculature are shown in FIGS. 10A-B, where vessels are shown as 3-dimensional projections (maximal intensity projections). In these images, slight vascular leak was identified as the haziness shown in some areas of the decellularized scaffold.

A critical feature of the decellularized matrix is the preservation of the native 3-dimensional structure. In order to evaluate the extent to which the structure of the decellularized scaffolds was preserved, a combination of scanning and transmission EM, micro-CT, and a microsphere permeability assay was used. The ultrastructural characteristics of decellularized lung was examined using SEM, and demonstrated maintenance of alveolar architecture and alveolar septae. Transmission EM demonstrated a completely intact alveolar basement membrane as well as collagen and elastin fibers. These EM findings are consistent with other work in decellularizing lung matrix, where such structures are retained [Lwebuga-Mukasa et al., 1986, Exp Cell Res 162: 423-35]. With strict control of vascular perfusion pressure during decellularization, the results presented herein demonstrate the retention of capillaries. Micro-CT imaging demonstrated retention of the vascular network down to vessels of 100 µm diameter, based on conservative estimates, with a substantial number of smaller vessels also intact.

Example 2: Contribution of Extracellular Matrix Components to the Mechanical Integrity of Decellularized Lung Tissue The following experiments were designed to evaluate the composition of the decellularized scaffolds in more detail with a focus on the mechanical properties of the scaffolds. Without wishing to be bound by any particular theory, it is believed that that decellularized lung scaffolds retain salient mechanical features of native lung, due principally to contributions from collagen and elastin. The results presented herein demonstrate the utility of the decellularized lung tissue as a platform to study lung mechanics independent of cellular contributions.

The results presented herein demonstrate that collagen content is retained, elastin content is retained at ~40% of native levels, while glycosaminoglycans are largely lost from the decellularized scaffolds.

The materials and methods employed in these experiments are now described.

Materials and Methods

Organ Harvest and Decellularization

Lung tissue was harvested and decellularized as described elsewhere herein.

Histological Analysis

Histology was used to characterize many decellularized lung scaffolds, and to confirm the removal of cellular material. Tissues were fixed, paraffin-embedded and sectioned. Analysis was performed with standard hematoxylin and eosin staining (H&E), Masson's trichrome for collagen, Verhoff van Gieson for elastin, and Alcian blue for proteoglycans, as well as staining for DNA using 4',6-diamidino-2-phenylindole (DAPI).

Collagen Assay

Collagen was quantified with a colorimetric assay to detect OH-Proline using a modified Grants method [Grant, 1964, 1964, J Clin Pathol 17:685-6]. Lung samples were lyophilized and weighed, then incubated in papain (140 µg/ml) at 60° C. overnight (Sigma). Papain-digested samples were incubated in 6 N HCl at 115° C. for 18 hours, neutralized, oxidized with chloramine-T, and reacted with p-dimethylaminobenzaldehyde. Absorbance was measured at a wavelength of 550 nm and a 1:10 w/w ratio of hydroxyproline to collagen was used to calculate the collagen content of the tissue. At least 4 samples were measured for native and decellularized samples.

Elastin Assay

Elastin was quantified using the Fastin Elastin assay kit (Biocolor, Belfast, N. Ireland). Lung samples were first lyophilized and weighed, and then the elastin was extracted following the method described in Foronjy et al. [Foronjy et al., 2008, Am J Physiol Lung Cell Mol Physiol 294:L1149-57]. Samples were incubated with 0.25M oxalic acid at 100° C., then centrifuged at 10,000 g and the supernatant saved. The supernatant from 5 extractions was pooled, and the supernatant from the 6th extraction was also measured to ensure that no more elastin remained in the tissue. The oxalic acid was cleared using a 10,000 molecular weight cutoff filter (Millipore), then resuspended in dH2O and analyzed using the Fastin Elastin kit according to the manufacturer's instructions. At least 4 samples were measured for native and decellularized samples.

Sulfated Glycosaminoglycan Assay

Sulfated glycosaminoglycans (sGAGs), including chondroitin, dermatan, heparan and keratan sulfates, were quantified using the Blyscan GAG assay kit. Papain-digested samples (prepared as described for the collagen assay, above) were assayed according to the manufacturer's instructions. Briefly, sulfated GAGs were labelled with 1,9-dimethyl-methylene blue dye and absorbance was measured at 650 nm.

Mechanical Testing

Figure 11:
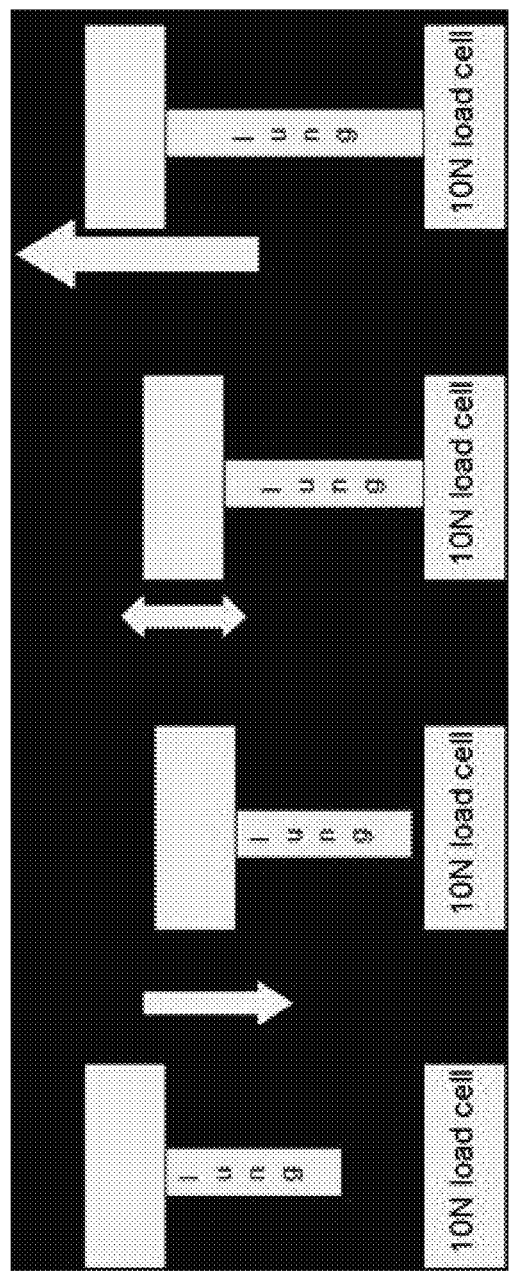
FIG. 11 is a schematic depicting a mechanical testing protocol. Briefly, a strip of lung tissue is attached to the upper plate, which is then lowered and the tissue attached to the lower plate. The tissue is cyclically stretched to 20% strain and then stretched until failure.

Native and decellularized lung samples were analyzed using an Instron 5848 equipped with a 10N load cell. Slices of tissue of known dimensions were cyclically pre-stretched for 10 cycles to 20% strain to investigate elastic properties and then stretched until failure to evaluate ultimate tensile strength (UTS). See FIG. 11 for a schematic of the testing protocol. Using tissue dimensions, engineering stress and engineering strain were calculated from force and distance.

The results of the experiments are now described.

Collagen and Elastin Content

As shown in FIG. 12C, collagen content in decellularized scaffolds was indistinguishable from native lung. This preservation of collagen is important as collagen plays a key role in the mechanical strength of the lung. Collagen content was also maintained on histochemical staining via Masson's trichrome, shown in FIGS. 12A-C. Also shown in FIG. 12C, collagen content was decreased in scaffolds decellularized with SDS, one of the decellularization methods that was not found to be suitable. It is believed that this loss of collagen correlates with decreased mechanical integrity in SDS decellularized scaffolds.

Elastin content is also preserved, although diminished, in the decellularized scaffolds, as demonstrated by both quantitative assay and histological staining (FIGS. 13A-C). Elastin fibers allow for the elasticity of the lung, critical to the natural recoil of the tissue that plays a key role in the relaxation and thus exhalation of the lung after inhalation. The retention of these fibers through the decellularization process is critical, as it allows the lung scaffold to be properly ventilated during efforts at reseeding the scaffold with pulmonary cell populations. Although the scaffolds lost 60% of the native elastin content, the remaining elastin was sufficient to allow elastic function of the lungs, as seen from the mechanical testing results discussed elsewhere herein.

Overall, the retention of these key ECM components allowed the scaffold to undergo physiological levels of mechanical stress, which is important as a variety of developmental and cell differentiation processes rely on mechanical stimuli. In addition, the ECM is critical in aiding cell attachment to the matrix, and the retention of these native ECM components facilitate cell attachment and spreading and thus the development of bioengineered lung tissues.

Proteoglycan Content

Proteoglycans consist of a core protein linked to one or more glycosaminoglycan (GAG) chains. Most GAGs are sulfated, enabling their detection via quantitative assay, the results of which are shown in FIGS. 14A-C. It was observed that the GAG content of the decellularized scaffolds was significantly lower than native lung (~6% of native lung levels). Proteoglycans are found either on the cell surface or within the extracellular matrix [Ferdous et al., 2007, Tissue Engineering 13:1893-904], and their removal is due in part to the removal of cell-bound GAGs. However, the GAGs found within the ECM can also be solubilized via the decellularization solutions. FIGS. 14A-C, is an alcian blue histological staining for proteoglycans, which show that the amount of GAGs remaining in the decellularized lung scaffolds was diminished compared to native lung, confirming the quantitative assay results.

Mechanical Characterization

Mechanical testing of peripheral lung strips was used to evaluate the quasistatic mechanics of both native and decellularized lung samples. The elastic regions of the stress-strain curves indicate that both native and decellularized samples demonstrated hysteretic behavior. Hysteresis demonstrates that lung is a viscoelastic material, and the difference between the expanding and relaxing curves represents energy that is not recovered during relaxation. In addition, samples did not creep, as shown in FIG. 15. If lung tissue were to creep, it would not deflate to its original position after an inflation; thus, the lung would never fully deflate and gas exchange would be impaired. This preservation of appropriate elastic lung behavior is important for a lung scaffold because loss of pulmonary elasticity is seen in several disease states, notably emphysema [Gelb et al., 2002, Chest 121:715-21].

Figure 16:
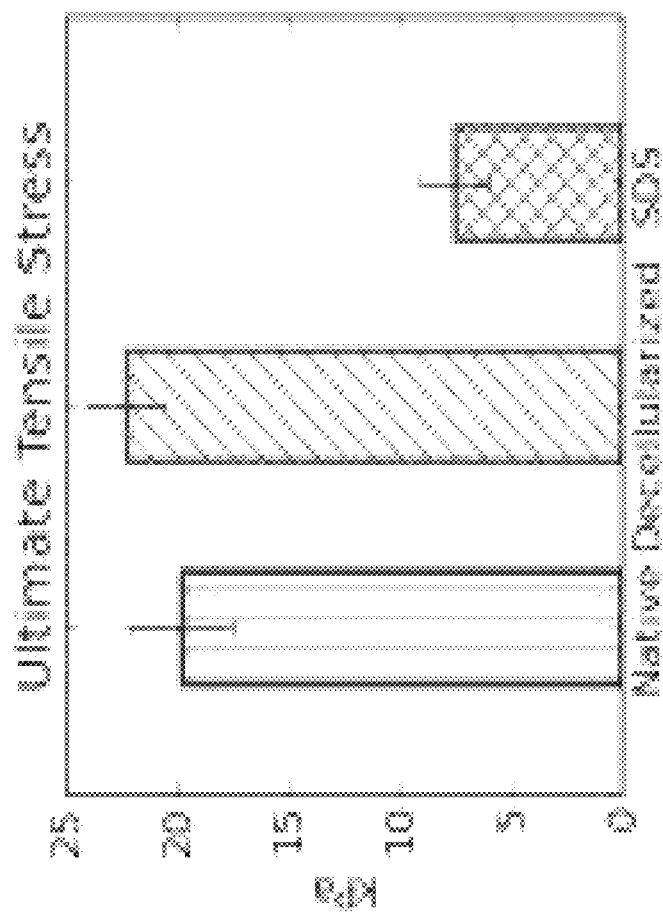
FIG. 16 is a chart depicting ultimate tensile strengths of native, decellularized and SDS-decellularized lung. SDS indicates a lung decellularized using sodium dodecylsulfate. * indicates p<0.01 compared to native.

Ultimate tensile strength (UTS) is the stress on a sample at failure, and is a measure of a material's strength. As demonstrated in FIG. 16, the UTS of decellularized samples was indistinguishable from that of native samples. If samples were decellularized in buffers containing sodium dodecyl sulfate (SDS), however, mechanical integrity was compromised as demonstrated by the decrease in UTS. SDS can degrade collagen, causing fragmentation and swelling of tissues [Bodnar et al., 1986, Thorac Cardiovasc Surg. 34(2):82-5; Gilbert et al., 2006, Biomaterials 27:3675-83] and has also been shown to increase tissue extensibility [Mirsadraee et al., 2006, Tissue Eng 12:763-73]. SDS is a highly ionic, amphipathic detergent, and its hydrophobic region can interact with proteins while the hydrophilic portion, especially when negatively charged, binds water and causes tissue swelling [Bodnar et al., 1986, Thorac Cardiovasc Surg. 34(2):82-5]. Although other studies have not always seen a decrease in UTS with SDS treatment [Mirsadraee et al., 2006, Tissue Eng 12:763-73], this may be due to tissue differences. Mirsadraee et al. studied pericardial tissue, which contains much more densely packed collagen fibers than lung. In lung, due to the geometry of the tissue, collagen fibers are highly distributed, and SDS-induced swelling can much more easily lead to collagen removal, as seen in the quantitative collagen assay.

The results presented herein demonstrate that the decellularized scaffolds can withstand relevant in vivo physiological forces.

The results presented herein confirmed that both collagen and elastin was preserved at functional levels. These findings confirmed that the principal contributors to lung mechanics are from collagen and elastin, and not from cellular constituents or proteoglycans. The results presented herein demonstrate the production of decellularized lung scaffolds that display characteristics of native lung, which make them promising substrates for tissue engineering applications as well as a platform for the study of detailed matrix mechanics and lung biology, development and physiology.

Example 3: Design and Validation of a Bioreactor for the In Vitro Culture of 3-Dimensional Lung Tissues A bioreactor can be used to culture 3-dimensional lung tissue in vitro. The development of such a bioreactor would be beneficial not only to research on the growth of engineered lung tissue, but to the study of pulmonary biology. There are currently no available systems that allow the long term in vitro culture of adult lung tissue.

The following experiments were conducted for the design of a bioreactor for the in vitro culturing of whole lung tissue. The bioreactor was designed to meet a series of design constraints aimed at the ability to provide sufficient nutrient supply and mechanical stimulation to the lung tissue in order to support cell survival and differentiation. Experiments were designed to evaluate whether the bioreactor could support the in vitro culture of whole lobes of lung tissue, demonstrated by maintenance of cell viability and differentiation state. In the process of evaluating the bioreactor, the effects of perfusion and ventilation on lung survival in the bioreactor was assessed. The results presented herein demonstrate that the bioreactor can be used for in vitro lung tissue culture and therefore applicable for engineering lung tissue.

The materials and methods employed in these experiments are now described.

Materials and Methods

Whole Lung Culture

Lungs were harvested from young adult (3 month-old) male Fischer 344 rats. All animal experimental work was approved by the Yale University Institutional Animal Care and Use Committee. Animals were anesthetized via intraperitoneal injection of sodium pentobarbital (Sigma, 40 mg/kg). After induction of anesthesia, the chest and abdomen were sprayed with ethanol and a transverse incision made just below the costal margin, entering the abdominal cavity. The diaphragm was punctured, and the ribs retracted, taking care not to touch the lungs. The inferior vena cava was severed and the lungs perfused via the right ventricle with 20-30 ml of PBS containing 50 U/ml heparin (Sigma) and 1 µg/ml sodium nitroprusside (Sigma). The trachea was then dissected and cut as high as possible. All remaining connections to the heart and lungs were dissected free, allowing removal of the heart, lungs and trachea en bloc from the animal.

Cannula Attachment

After removal of organs, cannulae were connected to the trachea and to the pulmonary artery trunk via the right side of the heart. The apex of the heart was cut off with a scalpel, and a right angle cannula was inserted through the right ventricle and into the pulmonary trunk. A syringe was attached to this cannula and 5-10 ml of heparinized saline was injected to ensure proper cannula placement and adequate perfusion of the lungs without leakage. This cannula was then secured with suture to the heart. A separate straight, barb-end cannula was inserted into the trachea and secured with suture. The lungs were then connected to the bioreactor, and decellularized following the protocol described elsewhere herein.

Cannulae were attached to the pulmonary artery via the right ventricle and to the trachea, and the lung was connected to the bioreactor. The airway was lavaged with 2% amphotericin, penicillin and streptomycin in PBS, followed by two lavages with PBS, and the bioreactor was then filled with media and culture begun. Vascular perfusion and ventilation were performed as dictated by the experimental conditions.

Bioreactor Components and Assembly

Bioreactor components were obtained from Cole-Parmer (Vernon Hills, Ill.) unless otherwise noted. A silicone stopper and 500 ml glass jar formed the basis of the bioreactor. PharMed tubing (Westlake, Ohio), sizes L/S 14 and L/S 16, was inserted through the silicone stopper to enable the necessary connections to the lung, including a perfusion loop, tracheal connection, air ventilation, and media exchange ports. Pressure was monitored using a TruWave pressure transducer (Edwards Lifesciences, Irvine, Calif.) between the perfusion pump and the connection to the pulmonary artery. Perfusion was accomplished using a Masterflex L/S variable speed roller pump (Masterflex, Vernon Hills, Ill.). Ventilation was performed using a multichannel programmable syringe pump (Cole Parmer), with inhalation and exhalation each performed over 30 seconds using a volume of 10 ml. A diagram of the bioreactor is shown in FIGS. 17A-C.

Histology and Immunofluorescence

After the desired culture period, lungs were fixed, paraffin-embedded and sectioned. Routine histology (H&E) was performed, as well as immunofluorescence for aquaporin-5 (type I epithelium), surfactant protein C (type II epithelium), CCSP (Clara cells), and PECAM-1 (endothelium). Sections were deparaffinized in xylene, rehydrated, and incubated with PBS with 0.2% triton-X (buffer) for 15 minutes. Antigen retrieval was performed using 0.02M citric acid in PBS for 20 min at 75-85° C., after which sections were rinsed in buffer. Blocking was performed for 1 hour at room temperature with PBS+1% bovine serum albumin and 0.75% glycine. Primary antibodies were rinsed off with buffer and secondary antibody was applied for 1 hour at room temperature at 1:500 dilution. Secondary antibodies were obtained from Invitrogen (AlexaFluor 555 or AlexaFluor 488x). Images were acquired with a Zeiss Axiovert 200M inverted fluorescent microscope.

Cell proliferation was assessed via staining for proliferating cell nuclear antigen (PCNA) (Zymed, San Francisco, Calif.), and apoptotic nuclei were detected with terminal deoxynucleotidyl transferase dUTP nick end labeling (TUNEL) stain (Calbiochem, San Diego, Calif.). Manufacturer's instructions were followed for both assays.

Microsphere Ventilation Assay

In order to determine if ventilation of lungs in the bioreactor was sufficient to induce movement of media to perfuse the vasculature, a simple assay was developed using 5 μm polystyrene microspheres (SPI Supplies, West Chester Pa.). Lungs were connected to the bioreactor, as described elsewhere herein, and ventilated but not perfused. The bioreactor chamber was filled with 100 ml of media containing 10 million microspheres (0.1 million microspheres per ml of media). The culture was allowed to proceed, with ventilation only, for 3 hrs. The lung was then fixed, paraffin-embedded, sectioned and analyzed using routine histology (H&E).

The results of the experiments are now described.

Bioreactor Design Requirements

The bioreactor incorporates key features of the rodent in vivo environment but was also designed allow the user to modify several key parameters depending upon the desired conditions. The design goals are as follows:

System must be capable of perfusing media through the vasculature at a rate specified by the user and within the physiological levels.

System must be capable of ventilating the lungs with air or media through the trachea. Negative pressure ventilation and the ability to constantly ventilate the lungs is preferable, in order to be consistent with normal physiological conditions.

Bioreactor should preferably allow for different media types to bathe the vascular and airway compartments of the lung.

Bioreactor must allow for gas exchange into the culture medium, while simultaneously meeting the above requirements for ventilation.

Bioreactor must have ports to allow for pressure measurements of the pulmonary artery and tracheal pressures. Pressures should ideally be within normal physiological values, with a pulmonary artery pressure of less than 15-30 mmHg [Li et al., 2004, Proc Natl Acad Sci USA 101:11488-93].

Bioreactor must have a means of allowing media exchange on a periodic basis.

Bioreactor must be small and self-contained such that it can fit within the physical confines of a standard tissue culture incubator.

All bioreactor components must be inexpensive and easily available.

Bioreactor and all components must be able to be sterilized, preferably via autoclave.

A bioreactor was designed and built that met the above criteria. A schematic of the bioreactor is shown in FIGS. 17A-C.

Bioreactor Perfusion System

Perfusion to the lung was provided via a roller pump that circulates media from the main bioreactor into the pulmonary artery. The perfusion rate can be specified by the user. The heart of the rat is kept attached to the lung in order to facilitate the connection of a cannula to the pulmonary arterial trunk through the right ventricle of the heart. However, the pulmonary vein was not connected directly to the perfusion loop. Rather, the pulmonary veins drained through the left side of the heart directly into the main bioreactor reservoir. The venous drainage of the lung exits directly into the main bioreactor.

The perfusion rate through the lungs can be set to a user's specifications. Physiologic flow rates in the adult rat are 40-80 ml/min, although for engineered tissue culture the flow rate is typically much less than this value. In an adult rat, the entire blood volume must pass through the lungs in order to become oxygenated, whereas during engineered tissue culture, only sufficient media to support the growth of the pulmonary cells must perfused. Thus, perfusion rates during engineered culture are closer to that in a fetal rat, where the blood flow to the lung is only 8-10% of the cardiac output due to a normal physiologic shunt [Hislop et al., 2000, Ped Resp Rev 1:321-7]. The pressure profile can be controlled to a limited degree using vasodilators such as sodium nitroprusside, which can be used to reduce pulmonary vascular pressure. Typically the perfusion pressure is kept below ~30 mmHg, the maximum value typically seen in the pulmonary arterial system [Li et al., 2004, Proc Natl Acad Sci USA 101:11488-93].

Bioreactor Ventilation System

The bioreactor was capable of both positive and negative pressure ventilation. In vivo, breathing is normally accomplished via negative pressure ventilation. The diaphragm contracts and the rib cage expands to create a negative pressure within the thoracic cavity, causing air to flow into the lung to relieve this pressure imbalance. After inhalation, the breathing muscles relax and the lung passively deflates.

Negative pressure ventilation is the primary mode of ventilation in the bioreactor. In order to effect a negative pressure surrounding the lungs, the main chamber of the bioreactor must be completely airtight. This is accomplished by closing off all air and pressure-monitoring vents. Then, a syringe pump is used to withdraw a set volume of air from the main bioreactor, creating a negative pressure. The only pathway for this pressure to be relieved is for media (or air) to flow into the lungs via the trachea, which is connected to a separate reservoir. The syringe pump then reverses direction to push air back into the main bioreactor. This reverses the buildup of negative pressure inside the chamber, and media (or air) flows back into the tracheal reservoir. The lung deflates passively during this time.

Tracheal Cannula Utilizes One-Way Valve:

As depicted in FIGS. 17A-C, the connection to the trachea involves a Y-connector and a one-way valve open to the main bioreactor. This type of connection is necessary due to leakage of fluid out of the airway compartment. During inhalation, a volume of media enters the lung. However, some of this media leaks across the alveolar membrane into the interstitial space or vasculature. Therefore, not all of the media that entered the lung during inhalation can be returned to the tracheal reservoir during exhalation. The design shown in FIGS. 17A-C, incorporates the feature of allowing all the media to enter the lung during inhalation. However, during exhalation, media can return to the tracheal reservoir either from the lung or from the main bioreactor via the one-way valve.

The bioreactor can also utilize positive pressure ventilation, by connecting the syringe pump directly to the tracheal cannula or tracheal reservoir.

Tracheal Inlet Modification:

In the context of the bioreactor, it was observed that during ventilation, the lung airway compartment was not supplied with sufficient fresh media. Without wishing to be bound by any particular theory, it is believed that this was because largely the same media was being ventilated in and out of the trachea due to the volume of media contained in the tubing between the trachea and the separate tracheal reservoir, with insufficient fresh media entering the trachea. The "dead space" in the airway medium flow loop prevented fresh medium from reaching the lung tissue during breathing. As a result, the bioreactor was modified such that the media followed a different path into and out of the lung during ventilation, as outlined in FIGS. 17A-C. Due to this modification, most of the media entering the trachea with each breath was sourced directly from the tracheal reservoir (and thus 'fresh' compared to the media that is exiting the trachea).

Oxygen Supply During Bioreactor Culture:

The oxygen content of tissue culture medium in the bioreactor during lung cultures was measured, in order to ensure that there was sufficient oxygen content. In particular, it is necessary to ensure that there is sufficient oxygen delivery during negative pressure ventilation, during which the main bioreactor is air-tight and the only portal for oxygen entry is via the tracheal reservoir. It was found that the oxygen tension does not drop significantly over the course of culture, and remained at 6.0-7.0 mg/L, which is the same as the level in normal tissue culture media. These levels exceed normal physiological levels of 80-100 mmHg (6-7 mg/L corresponds to a partial pressure of 137-159 mmHg).

Bioreactor Pressure Profiles

The pressure profiles in the trachea and pulmonary artery of engineered lung tissue cultured in the bioreactor was measured, in order to ensure pressures are within expected or physiological limits. FIGS. 18A-B shows representative profiles. The perfusion pressure was typically kept between ~2 and 30 mmHg. In the example given, the baseline perfusion pressure varied between 10-17 mmHg. However, the effects of the negative pressure ventilation were superimposed on this profile, thus lowering the perfusion pressure to 0-7 mmHg during a negative pressure 'breath'. This effect is seen physiologically, wherein the pressure drops in the pulmonary vasculature with inspiration. In the bioreactor, the pulmonary vein drained directly into the main chamber, which also served as the 'thorax', which is where negative pressure was created in order to ventilate the lung. This served to increase transmission of negative pressures from the bioreactor to the perfused vasculature.

From the perfusion pressure profile, the maximum negative 'thoracic' pressure was ~−12 mmHg, approximately consistent with physiological values. Therefore, during an inhalation, this negative pressure was exerted on the airways, driving fluid (or air) into the lungs from the tracheal reservoir. This pressure gradually decreases up the airway tree, and was −3 mmHg at the tracheal inlet. Of note, the pressure at the inlet to the trachea was essentially zero physiologically, as it is tied to atmospheric pressure. However, in the bioreactor, this pressure remained slightly negative during inhalation due to the length of tubing between the trachea and the tracheal reservoir, where the pressure reaches zero.

Media and Oxygen Requirements

The following results show a series of calculations intended to help determine the volume of media and air required for a rodent lung cultured in the bioreactor.

Tissue Culture Comparison:

During in vitro tissue culture, it is common to feed 5 million cells with 12 ml medium every 3 days. If it is assumed that the adult rodent lung contains 100 million cells, which corresponds to a media requirement of at most 240 ml every 3 days. However, this would be an overestimate as cells in tissue culture are generally actively replicating, while many cells in an intact rodent lung are quiescent and thus have lower media requirements.

Glucose Consumption Requirements:

It has been demonstrated that the glucose consumption of a perfused rat lung is 43 µmol per gram dry weight per hour [Kerr et al., 1979, Am J Physiol 236:E229-33]. The lung of an adult rat has a dry weight of ~150-250 mg [; Inokawa et al., 2006, Ann Thorac Surg 82:1219-25] while tissue culture medium typically contains 5.5 mmol/L glucose. Therefore, the lung of an adult rat would require 28-47 ml of tissue culture media per day in order to supply its glucose consumption requirements.

Oxygen Requirements:

Pulmonary artery endothelial cells consume 6 nmol of oxygen per million cells per minute [Xu et al., 2007, Proc Natl Acad Sci USA 104:1342-7], while rat type II epithelial cells consume 1.25 nmol per minute [Dobbs et al., 1980, Biochim Biophys Acta 618:510-23]. Assuming 100 million cells in an adult rat lung and assuming all cells in the lung consume oxygen at the higher rate, a rat lung would require at most 26 mg of oxygen per day. Tissue culture media contains approximately 6 mg of oxygen per liter, and the bioreactor contains approximately 300 ml of media. Thus, the media can provide 1.8 mg of oxygen with each exchange of fresh media (every 3 days). In addition, oxygen is contained in the air in the bioreactor; there is approximately 200 ml of air in the main bioreactor. Air in the incubator contains ~20% $O_2$, which at sea level and 37° C., corresponds to ~260 mg of oxygen per liter of air. Therefore the air in the bioreactor contains ~52 mg of oxygen.

The bioreactor of the invention can provide the media and oxygen requirements of a cultured rodent lung based on the above calculations. Routinely, a total of 240 ml of medium can be supplied in the bioreactor (180 ml in the main bioreactor and 60 ml in the tracheal reservoir), and the air in the bioreactor can be exchanged daily. These conditions are believed to be sufficient to provide more than enough nutrients and oxygen to a cultured lung.

Whole Lung Culture

In order to validate and optimize the design of the lung bioreactor, in vitro culture of whole native rodent lungs was used. Lungs were cultured for up to 7 days in the bioreactor. It has been demonstrated that the bioreactor provided sufficient nutrient supply and mechanical stimulation to maintain cell survival and differentiation as well as lung morphology.

The culture of native lung was also used in the bioreactor to examine the effects of bioreactor conditions on cell survival, lung morphology, and maintenance of cellular differentiation state. The effects of air versus liquid (media) ventilation on lung morphology was initially compared. The effects of ventilation technique and nutrient delivery on cell survival was then evaluated. The effect of vascular perfusion pressure on cell survival and differentiation was also evaluated. The ability of the bioreactor to maintain cellular differentiation during 7-day cultures was also evaluated.

Effects of Ventilation with Air Versus Media on Overall Lung Morphology:

The effects of ventilating lungs cultured in the bioreactor with either media or room air (~20% $O_2$) was evaluated. It is believed that ventilation with media would offer improved cell survival as this would provide improved nutrient delivery, which may be more important in the bioreactor as there is no perfused bronchial circulation to supply the large airways. However, ventilation with air is the condition to which adult lungs are conditioned, and pulmonary epithelium is frequently cultured in the presence of an air-liquid interface, which has been shown to enable appropriate pulmonary development in fetal rat lungs [Funkhouser et al., 1976, Biochem Biophys Res Comm 70:630-7]. Therefore, experiments were also designed to examine whether ventilation with media would result in loss of epithelial differentiation state, due to the lack of an air-liquid interface.

After 3 days of culture, significant differences were noted between lungs ventilated with media versus air. As shown in FIGS. 19A-C media ventilation appeared similar to native lung; however, air-ventilated lungs showed greatly dilated airways, with cell debris evident in the airway (FIG. 19C). Furthermore, the center panel of FIG. 19C shows that the bronchial and bronchiolar epithelium of air-ventilated lung was completely absent, a finding that was consistent across the entire lung. In addition, dilated peripheral airspaces were evident, as shown in the right panel of FIG. 19C.

It was also observed that the airway epithelium was also denuded if media perfused through the vasculature (in addition to ventilation with air), while if media perfused through the vasculature with no ventilation, the airway epithelium was intact. This suggests that the loss of airway epithelium is not due to a lack of sufficient media, but is related to effects of air ventilation. It was observed that bronchial circulation was not perfused for any cultures.

Epithelial cells are often cultured at an air-liquid interface, consistent with their physiologic locations. An air-liquid interface (ALI) is often utilized to induce epithelial differentiation [Gruenert et al., 1995, Am J Physiol 268:L347-60; Wong et al., 2009, J Clin Invest 119:336-48; Hosokawa et al., 2007, Connect Tissue Res 48:9-18], and a lack of an air-liquid interface can lead to reduce ciliogenesis [Ostrowski et al., 1995, Exp Lung Res 21:957-70; Yeh et al., 2007, Laryngoscope 117:1439-44]. In addition, an air-liquid interface enables the maintained secretion of surfactant by type II epithelium when cultured in vitro [Mason et al., 2002, Am J Physiol Lung Cell Mol Physiol 282:L249-58]. Therefore, it was expected that differences in cellular differentiation state in the absence of an ALI would occur. However, significant changes in the expression patterns of Clara cell secretory protein (CCSP), surfactant protein C (SPC), or aquaporin (AQP) in lungs ventilated with media, as shown for cultures performed out to 7 days in FIG. 25B was not observed.

Effect of Perfusion on Cell Survival:

The effect of vascular perfusion on cell survival and cellular differentiation in cultured native lungs in the bioreactor was examined, with the aim of determining if perfusion alone could support in vitro lung culture, and if so what perfusion pressure was optimal. Complicating these experiments was the fact that, after explantation of a lung, vascular permeability was rapidly increased. Isolated lung perfusion using pressures of 10mmHg can cause pulmonary edema within 10 minutes [Wierup et al., 2005, J Heart Lung Transplant 24:379-85]. Vascular leak was observed within 5-10 minutes of explantation, with 3-4% of small particles (28 nm radius) leaking across the alveolar-capillary membrane. Extensive pulmonary microvascular leak could result in less or even no media delivery to the distal capillaries and venous structures. Therefore, higher vascular perfusion pressures than the physiological levels of ~1-10 mmHg may be required in order to deliver flow distally and keep distal capillaries patent [Li et al., 2004, Proc Natl Acad Sci USA 101:11488-93].

The effect of vascular perfusion pressures on cell survival during 3 day native lung culture in the bioreactor was examined. As demonstrated in FIGS. 20A-B, higher perfusion pressures of up to 30 mmHg resulted in fewer apoptotic cells as well as higher cell density, compared to pressures of 10 or 20 mmHg. However, regardless of perfusion pressure, maintenance of cellular differentiation was poor with vascular perfusion. Substantially lower CCSP and SPC levels were observed (FIGS. 21A-D), while aquaporin expression was almost completely absent. PECAM expression was observed in the larger vessels of the vasculature, but decreased expression was observed in capillaries, as shown in FIGS. 22A-B. These experiments demonstrated that perfusion alone was not sufficient to maintain sufficient cell survival or cellular differentiation.

Effect of Media Flow Path in the Airway Compartment on Cell Survival:

While ventilation with media permitted the maintenance of lung morphology and cell differentiation, significantly higher rates of apoptotic cells in ventilated cultured lungs compared to native was observed (see FIGS. 23A-B and 28A-F). It is believe that this was due to insufficient fresh media delivery, and thus experiments were designed to modify the bioreactor in order to increase the delivery of fresh media to the airway compartment during ventilation. As shown in FIGS. 17A-C and described elsewhere herein, there is a single line connecting the main bioreactor to the tracheal reservoir. This length of tubing is approximately 40-45 cm and contains 3-3.5 ml of media. During ventilation, ~2.5-3.0 ml of media is drawn into the lung during a negative pressure inhalation, and the same volume of media is returned via the tubing to the tracheal jar. Therefore, of the ~2.5-3.0 ml of media that enters the lung during each 'breath', this media is not fresh but simply returns into the lung from the tubing. Therefore, the actual media delivery to the lung is far less than would be delivered by ventilation with fresh media.

The bioreactor design was modified to add a second connection between the lung in the main bioreactor and the tracheal reservoir. Using one-way check valves, one connection was used for media delivery during inhalation and the other connection was used for media return during exhalation. This modification reduced the 'recycled' media from ~2.5-3.0 ml to only ~0.75 ml with each ventilation cycle, and therefore greatly increased the delivery of fresh media.

The effects of this bioreactor modification are shown in FIGS. 24A-C, where the additional breathing line was shown to improve cell survival. The percent of apoptotic cells was reduced to 3.9% for 'loop' ventilation from 21.5% for ventilation with a single line ('vent only' on FIGS. 27A-B). This compares to 0.5% for native lung.

While 'loop' ventilation increases the delivery of media to the lung by reducing the amount of 'recycled' medium, media delivery can also be increased with the addition of vascular perfusion. Perfusion together with ventilation reduced cell apoptosis to 7.9% from 21.5% for single-line ventilation alone (FIGS. 23A-B). The 'loop' ventilation modification slightly increased overall cell number compared to single-line ventilation (FIG. 23B), but this was not a significant difference. For both single-line and 'loop' ventilation, cell number was reduced compared to native but not statistically significant.

The results presented herein demonstrate that ventilation alone enables the survival of native lung tissue in the bioreactor for during 3-day cultures, provided sufficient fresh media is delivered to the lung using either the 'loop' ventilation modification or supplemental vascular perfusion. Loop ventilation demonstrates the best overall results, minimizing cellular apoptosis while maximizing cell number in cultured lung tissues.

Cellular Morphology, Cellular Differentiation, and Alveolar Structure:

In order to more fully validate the bioreactor design, 7 day cultures of native lung were performed. These cultures utilized ventilation with media with the 'loop' modification described elsewhere herein, but without any vascular perfusion. Vascular perfusion was not utilized, although future studies could explore the addition of perfusion to long-term ventilated cultures using 'loop' ventilation.

Lungs were evaluated via histology for cell proliferation, apoptosis, and maintenance of cellular differentiation via staining for aquaporin-5 (type I epithelium), surfactant protein C (type II epithelium), Clara cell secretory protein (Clara cells), and PECAM-1 (endothelium). Overall pulmonary architecture was preserved, including alveolar structure, as shown in FIGS. 25A and 25B. Lower magnification images were not distinguishable from those shown in FIGS. 19A-C for media breathing. In addition, as shown in FIGS. 25C through 25J, patterns of expression of cellular markers were not substantially different from native lung.

Figure 26:
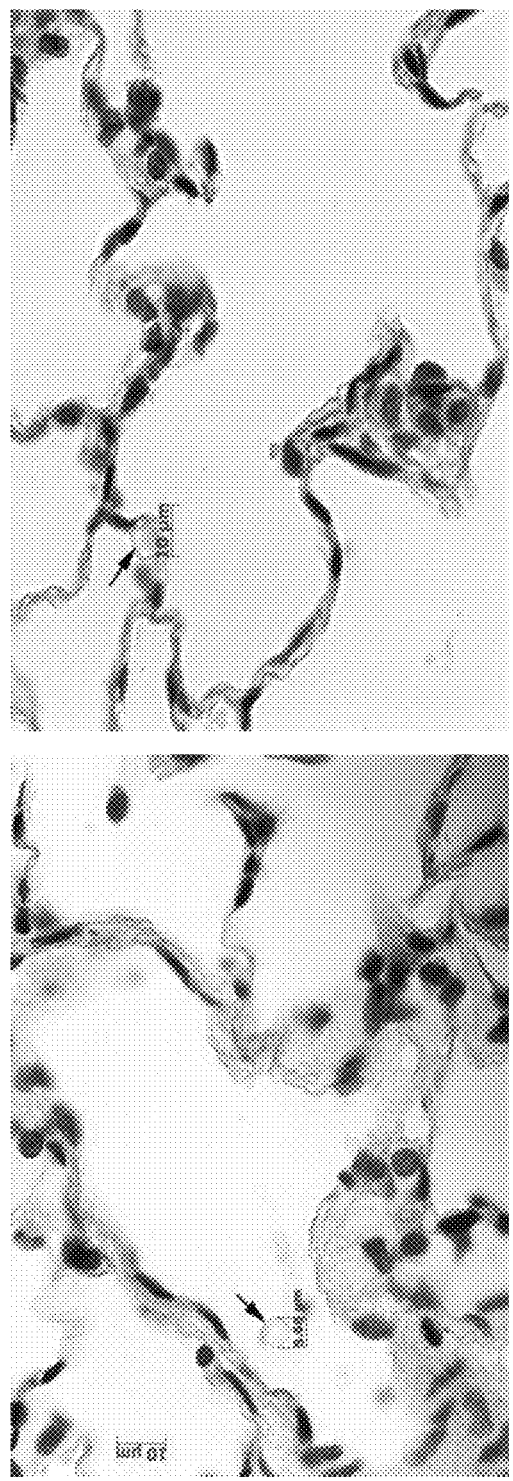
FIG. 26 is an image demonstrating that ventilation enables passive perfusion of pulmonary vasculature. Microspheres are found in vessels and capillaries due solely to ventilatory motions of the lung during in vitro culture.

Ventilation Alone Enables Passive Perfusion of the Vasculature of the Lung:

It has been demonstrated that ventilation alone can enable cell survival and maintenance of cellular phenotype of several key lung cell types, including endothelium, for up to 7 days. However, this is in the absence of active perfusion of medium through the vasculature, which was initially surprising. In order to investigate why the lack of perfusion did not affect endothelial survival or differentiation, an experiment using 5 μm microspheres to investigate the effect of ventilation on the movement of fluid into the vasculature was performed. It is believed that the physical movements induced by ventilation were sufficient to cause passive movement of media into and out of the vasculature, which is open to the media in the bioreactor. In this experiment, lungs were ventilated for 3 hours in the bioreactor which was filled with media containing 5 μm microspheres. If microspheres were observed in the vasculature of the lung, this indicates that passive perfusion was induced by ventilation. As demonstrated in FIG. 26, microspheres were found in both large vessels as well as some capillaries. These results indicate that ventilation alone is sufficient to induce media movement in the vasculature, thus allowing maintenance of the endothelium despite the lack of perfusion.

This movement of media in the vasculature is a result of the physical motion of the lung due to ventilation. Diffusion alone would be insufficient to move such large particles into the vasculature. The expected microsphere movement into the vasculature due to diffusion using Fick's second law can be approximated.

Supporting Cell Survival and Differentiation

The results presented herein demonstrated that vascular perfusion alone was not sufficient to support cell survival and cell differentiation, including surfactant production by type II epithelium. However, negative pressure ventilation with media was sufficient to support extensive cell survival (to 95.1% of native levels) as well as maintain the differentiation of epithelium and endothelium.

The overall objective of the experiments of the Example was to demonstrate the valid design of a bioreactor capable of culturing whole rodent lungs in vitro for long time periods, with the objective of using this bioreactor for the future culture of engineered lung tissues. The results demonstrate a successful design that is suitable for use in engineered lung culture.

Example 4: Epithelial Development in Engineered Lung Tissues

The results presented herein demonstrate that the decellularized scaffolds are not cytotoxic and support the adherence and proliferation of a wide range of pulmonary cell types, including epithelial, endothelial, and mesenchymal cells. In some instances, stem cells can be used to engineer a lung tissue. In order for engineered lung tissue to be useful, it must be able to connect to a vasculature and an airway. The airway must be continuous with alveoli, while the vascular connections must lead to a dense capillary network surrounding the alveoli.

The results presented herein demonstrate that the development of engineered lung tissues is affected by key bioreactor conditions, including medium type, perfusion, ventilation, and the presence of an air-liquid interface. In some instances, ventilation with culture medium (i.e. "liquid ventilation") aids in the differentiation of airway structures and epithelial cells. In addition, static culture of small pieces of engineered tissue at an air-liquid interface exhibited significant effects on tissue growth, and that in the bioreactor, ventilation with air affects cellular differentiation and the development of epithelial structures.

The materials and methods employed in these experiments are now described.

Materials and Methods

Scaffold Preparation

The lungs of adult Fischer 344 rats were harvested and decellularized as described elsewhere herein. Following the decellularization procedure, the scaffolds were rinsed in 10 changes of sterile water, followed by rinsing for at least 12 hours in 10% penicillin/streptomycin in PBS. In later cultures, lungs were also rinsed in 10% FBS to aid removal of DNA remnants. The lungs were then transferred to a new, sterile bioreactor with a complete perfusion and breathing system attached. The lungs were subsequently rinsed twice in PBS and once in the media to be used for culture.

Neonatal Cell Isolation

Lungs were isolated from neonatal (~7 day-old) rats as discussed elsewhere herein. Lungs were then rinsed for 10 sec in 70% ethanol and rinsed twice in Dulbecco's modified Eagle's medium (DMEM, Gibco), and then transferred to a sterile, dry Petri dish. Lungs were minced for 5 minutes with a scalpel, and then transferred to a conical tube for elastase digestion. DNase, collagenase and elastase were obtained from Worthington Biochemical (Lakewood, N.J.). Elastase digestion was performed for 20 minutes at room temperature with agitation, using 4 U/ml elastase in DMEM with 100 U/ml DNase. Tissue chunks were subsequently filtered through a 70 µm nylon filter and rinsed with DMEM. Undigested chunks were transferred to a clean tube and digested with collagenase for 1 hour at room temperature with agitation, in a solution of 1mg/ml collagenase in 1:1 DMEM:PBS with Ca2+ and Mg2+. Collagenase-digested tissue was again filtered through a 70 µm filter and undigested pieces were physically crushed using a syringe plunger. The remaining tissue was rinsed with DMEM and filtered through a 70 µm filter. Cells from the collagenase and elastase digestions were combined, then washed three times in DMEM and once in the media to be used for culture. Cell viability was assessed using trypan blue dye exclusion and cells were then seeded into the decellularized scaffolds as described elsewhere herein.

Neonatal Cell Seeding

After pulmonary cell isolation and preparation of the decellularized scaffold, the isolated cells were suspended in the medium to be used for culture. For seeding of the airway compartment, 15 ml of cell suspension per bioreactor was injected into the tracheal reservoir and cells were seeded by negative pressure ventilation to transfer the cells into the airway compartment of the lung. For seeding of the vasculature, 3 ml of cell suspension per bioreactor was injected into the pulmonary artery. The cells were allowed to adhere overnight without perfusion or ventilation, after which perfusion and/or ventilation was begun depending on experimental conditions.

Engineered Tissue Culture

After seeding, the lungs were cultured statically overnight, after which perfusion or ventilation was begun. Perfusion and ventilation were varied according to experimental conditions. Culture medium was replaced twice weekly. For ventilation conditions, lungs were ventilated continuously except for a brief pause daily in order to allow manual exchange of air in the bioreactor. For the culture of pieces of engineered tissue, after overnight seeding, scaffolds were removed from the bioreactor and cut into small (1-3 mm) pieces using sterile scissors. The pieces were transferred to Petri dishes for culture and, if indicated, later transferred to a Petri dish with a 0.4 µm filter insert for air-liquid interface culture.

Flow Cytometry

After cell isolation, cells were rinsed in buffer (PBS with 2 mM EDTA and 0.5% bovine serum albumin). For staining of intracellular antigens, cells were fixed with 1% formaldehyde for 15 minutes at room temperature, then permeabilized with 0.2% triton-X in PBS. Primary antibodies were applied in buffer for 30 minutes at R.T. at 1:100 dilution. After 3 rinses in buffer, secondary antibodies were applied for 20 minutes at room temperature at 1:100 dilution. Cells were analyzed on Becton-Dickinson FACSCalibur machines at the Yale School of Medicine Cell Sorting Facility.

The results of the experiments are now described.

Scaffold is Not Cytotoxic

Initially, MLE-12, a tumor-derived lung epithelial cell line was used for preliminary culture experiments on the decellularized lung scaffolds. These experiments were performed to demonstrate that the scaffold was not cytotoxic, as well as to demonstrate the first-order validity of the bioreactor system for cultures utilizing decellularized scaffolds. It was observed that the MLE-12 cell line exhibited robust cell growth during culture periods of up to 10 days on decellularized scaffolds in the bioreactor, with perfusion of media through the vasculature. Histology is demonstrated in FIGS. 27A-B. Cells appeared to form very primitive alveolar structures at 3 days, but subsequently proliferated extensively, and uncontrolled cell growth is shown by 7 days, an expected outcome as this is a tumor-derived cell line. These experiments were a preliminary step in the validation of the bioreactor and the decellularized lung scaffolds, and justified the subsequent experiments using freshly isolated neonatal pulmonary cells.

Harvest of Neonatal Pulmonary Cells

Neonatal pulmonary cells were chosen for several reasons, including the ability to isolate a large number of cells which represent a heterogeneous mix of pulmonary cell types, because rodent lung epithelium is diffcult to culture in vitro and because the pulmonary cells of neonatal rats are young and relatively plastic [Massaro et al., 1985, J Clin Invest 76:1297-305; Meyrick et al., 1982, Am Rev Respir Dis 125:468-73].

Conditions for cell isolation were optimized based on cell number, viability, and distribution of cell types based on flow cytometry. Primary markers used were surfactant protein C (SPC; type II pneumocytes), aquaporin-5 (AQP; type I pneumocytes), Clara cell secretory protein (CCSP; Clara cells), and platelet endothelial cell adhesion molecule-1 (PECAM-1; endothelial cells). Conditions for cell isolation were chosen as a result of iterated experiments that optimized overall cell number and viability. The selection of enzymes and incubation conditions was optimized based on cell yield and viability, as assessed by total cell number, trypan blue dye exclusion, and flow cytometry analysis.

Flow cytometry data of a sample lung isolation that was obtained under an 'optimized' isolation regimen is shown in FIGS. 28A-F. In a typical isolation, 5-10% of cells are CCSP-positive, 40-60% of cells are SPC-positive, 2-8% of cells are AQP-positive, 1-2% of cells are cytokeratin-14-positive, 10-30% of cells are PECAM-1 positive, and 5-10% of cells are α-actin-positive. Using cytospin preparations, staining for CCSP and SPC was confirmed. While most of these percentages are within expected range, one would expect higher yield of type I pneumoytes (AQP-positive), based solely on its prevalence in native lung. However, type I pneumocytes are very fragile and many of them are unlikely to survive the cell harvesting process. Total cell yield from a litter of pups (7-12 pups) was approximately 100 million cells, with viability of 75-85%.

Preliminary Identification of Bioreactor Conditions for Engineered Lung Culture

Experiments were designed to explore various variables and suitable conditions based primarily on cell density, viability and morphology via histology, as well as some evaluation of protein expression. The conditions that were evaluated are briefly addressed below.

Medium choice: Several medium compositions, varying both the base medium and serum concentration were evaluated. Epithelial repopulation, principally type II epithelium, using several medium conditions, including BGJb (serum-free), DMEM with 10% FBS, EGM-2 with 15% FBS, and a 3 part to 1 mix of EGM-2+15% FBS and BGJb was observed. The medium types BGJb and DMEM+10% FBS provided superior conditions for overall epithelial growth, based on histology and immunofluorescence staining. As a result, these media were used for subsequent experiments. However, the invention should not be limited to any specific medium. This is because any medium that promotes the desired proliferation and differentiation can be used.

Perfusion and ventilation: Both perfusion and ventilation was used during the preliminary experiments. For example, cultures were perfused at 2-5 ml/min in order to provide a nutrient supply. The effect of ventilation once-daily with a single breath was also evaluated. However, significant differences in the resulting engineered lung cultures was not detected. Despite not observing a clear benefit from the once-daily ventilation, it was decided that this minimal level of ventilation would provide a more physiological culture environment. Therefore, for the majority of subsequent experiments, the cultures were perfused and ventilated once daily with a single breath.

Decellularized Scaffolds Support the Growth of Epithelial, Endothelial and Mesenchymal Cells The following experiments were designed to demonstrate the validity of the decellularized scaffolds, the lung bioreactor, and the isolated neonatal pulmonary cell population for the development engineered lung tissue. The precise conditions used in the culture of these engineered tissues are identified in Table 1. Also described in the table are conditions that were specifically probed to evaluate the effects of those conditions on engineered tissue growth. However, the invention is not limited to these conditions. Rather, any applicable condition is encompassed in the invention so long as the conditions promote generation of an engineered lung in the context of the bioreactor.

TABLE 1

Bioreactor conditions for engineered lung culture

| Condition | Media | Ventilation | Perfusion | Length of culture |
|---|---|---|---|---|
| Validation | BGJb; DMEM + 10% FBS | Continuous; Once daily | 2 ml/min | 4-8 days |
| Perfusion | DMEM + 10% FBS | None | 2 ml/min | 8 days |
| Ventilation | DMEM + 10% FBS | Continuous with media | 2 ml/min | 8 days |
| Air-liquid interface | DMEM + 10% FBS | Continuous with media for 4 days, then air for 4 days | None | 8 days |
| Media screen | DMEM + 10% FBS to BGJb transition | Continuous | None | 8 days |

Demonstration of Epithelial Cell Repopulation

The results presented herein demonstrate the adherence and proliferation of epithelial cells on decellularized lung scaffolds. For these experiments, DMEM+10% FBS medium, perfusion of the vasculature at 2 ml/min, once daily ventilation, uncoated decellularized scaffolds, and unsorted neonatal pulmonary cell populations (the 'optimized' conditions described elsewhere herein) was used.

Figure 29:
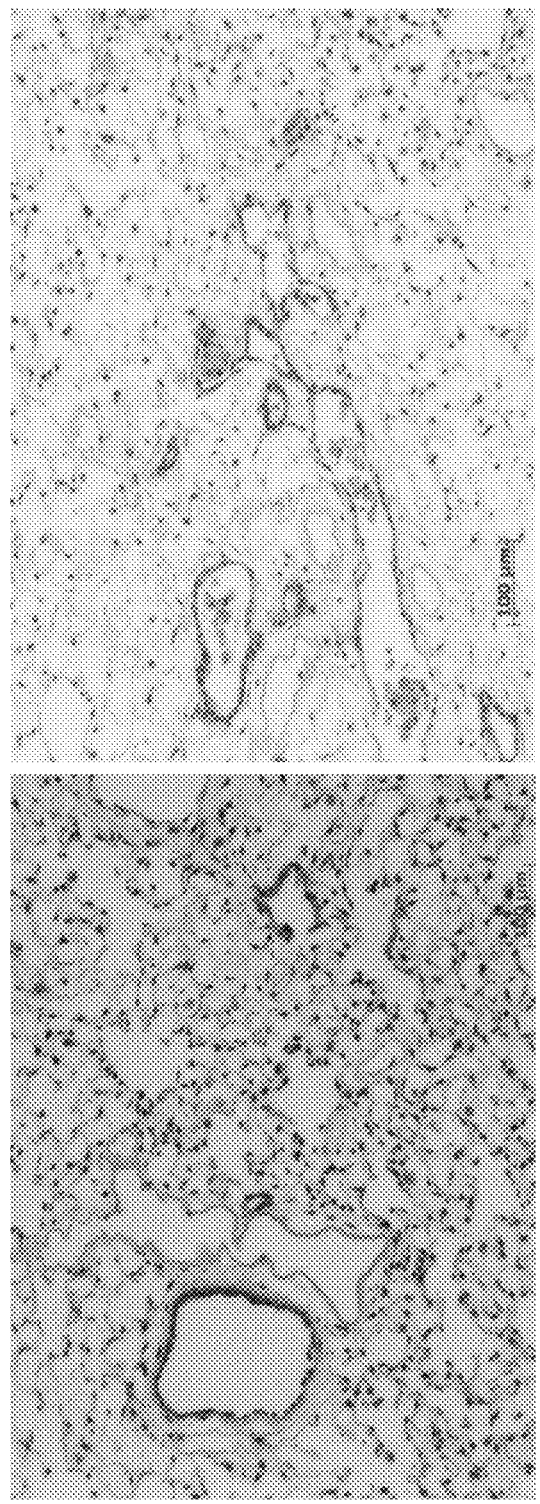
FIG. 29 is an image depicting H&E stain of engineered lung at 8 days of culture. Conditions here are optimized for epithelial cell growth.

FIG. 29 shows H&E staining of engineered lung tissue. At 4 days, a significant number of organized, cuboidal-epithelial-lined developing epithelial structures was observed, while at 8 days, fewer such structures were observed and many cells adopted a more mature phenotype. At 4 days, many cells were proliferating, while at 8 days, fewer proliferating cells were observed (FIGS. 30A-B). At both 4 and 8 days, no significant numbers of apoptotic cells was observed (FIGS. 31A-B).

Immunofluorescence was used to document the expression of key epithelial cell markers, using aquaporin-5 for type I pneumocytes, surfactant protein C for type II pneumocytes, and Clara cell secretory protein for Clara cells. Type II epithelial cells generally predominated in the cultures, especially at later time points, as shown in FIGS. 33A-C. Clara cells were observed at high densities at 4 days, with fewer cells at 8 days (FIGS. 32A-C). Staining for aquaporin at 4 days was also observed, although significantly less aquaporin staining was observed at later time points (FIGS. 34A-C).

It was observed that aquaporin staining for type I epithelium depicts cells that are cuboidal in shape at 4 days of culture, which is contrary to their usual flat morphology, as the cells that line alveoli in functioning lungs. In addition, these cuboidal cells also frequently stained positive for either SPC or CCSP, as seen in FIGS. 36A-C and 37. Therefore, it is unlikely that the cells that express aquaporin at 4 days are mature type I epithelium, as would be suggested by a flattened morphology and expression of aquaporin without other markers.

Type I pneumocytes are derived in vivo from type II epithelial cells, which are a locally resident precursor cell for alveolar epithelium. In native lungs during development, type I pneumocytes do not achieve final differentiation state in the absence of fetal breathing movements [Inanlou et al., 2005, Dev Dyn 233:772-82] and remain cuboidal in shape on histology and TEM [Inanlou et al., 2005, Histol Histopathol 20:1261-6].

The lack of type I pneumocyte differentiation was not surprising in these cultures that were not regularly ventilated. The cells that do express aquaporin most likely arise from a local precursor cell that had not fully differentiated to type I epithelium. Therefore, the decellularized scaffolds can support the attachment and proliferation of pulmonary epithelium. Robust growth of type II epithelium, as well as Clara cells and cells that are likely the precursors to fully differentiated type I epithelial cells was observed. We observe these findings under conditions of medium perfusion through the vasculature with only occasional breathing movements.

Epithelial Progenitor Cell Repopulation

Figure 35B:
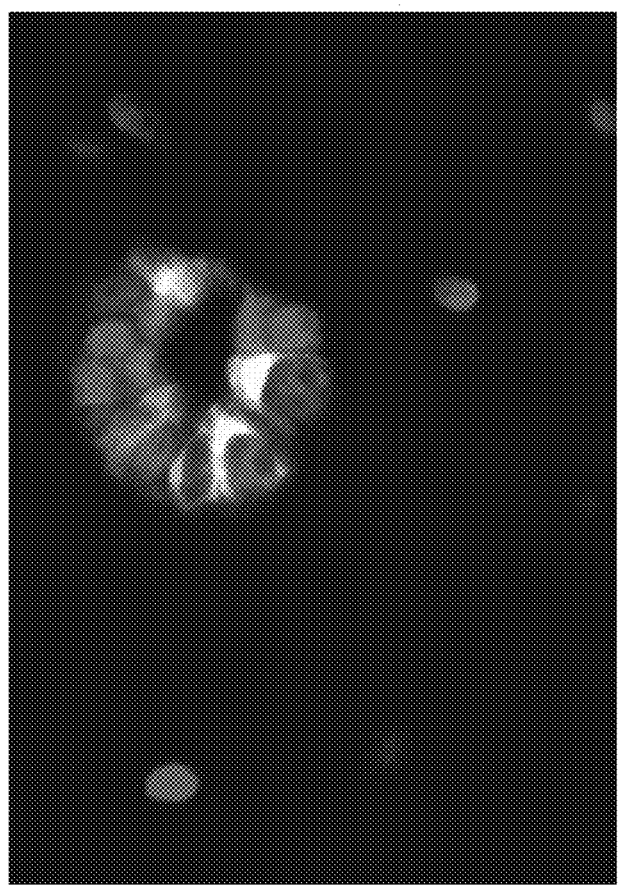
FIGS. 35A and 35B are a series of images depicting dual staining for SPC and CCSP in engineered lung tissue. SPC is stained green, CCSP is stained red, and nuclei are counterstained blue with DAPI. SPC-CCSP dual positive cells appear yellow.
Figure 35A:
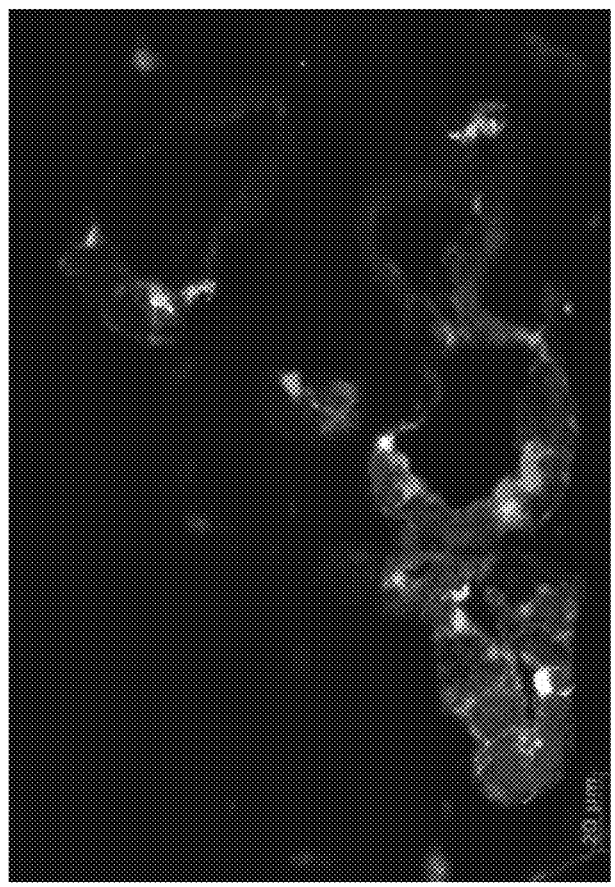

Growth of two types of pulmonary epithelial progenitor cells on the decellularized scaffolds was observed. Cells that are dual-positive for CCSP and SPC are reported to be local progenitor cells, termed bronchoalveolar stem cells, which can differentiate into both Clara cells and type II pneumocytes and are found at the bronchoalveolar duct junction [Lane et al., 2007, Regenerative Medicine 2:407-15; Kim et al., 2005, Cell 121:823-35]. FIGS. 35A-B shows such dual-positive cells, which are found in structures consistent with the appearance of terminal bronchioles, the expected physiological location of these cells.

Figure 37:
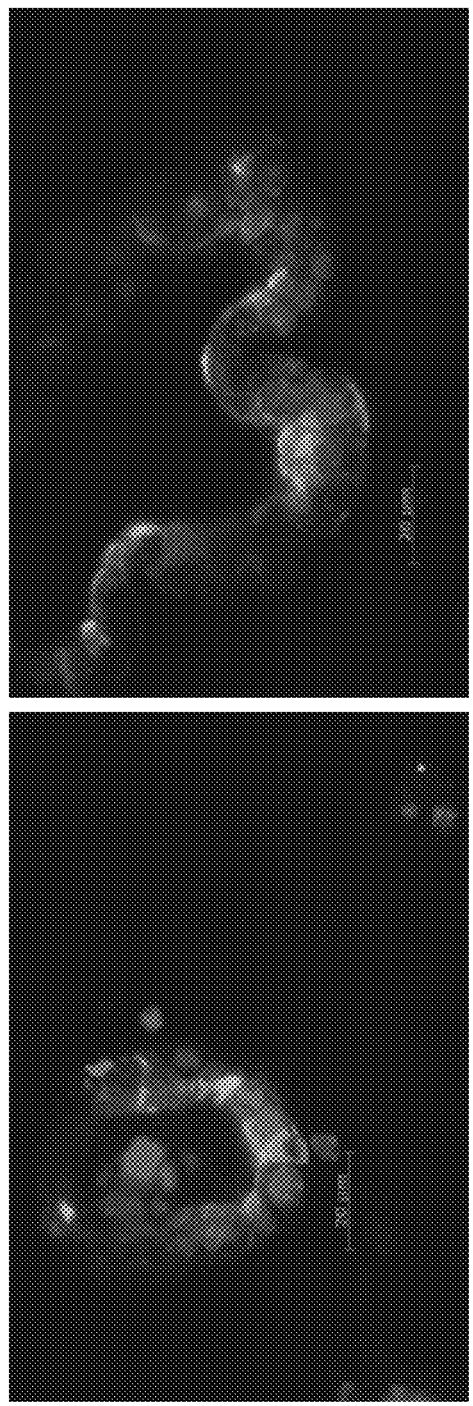
FIG. 37 is an image depicting dual staining for cytokeratin-14 and CCSP in engineered lung. Cytokeratin-14 is stained red, CCSP is stained green, and nuclei are counterstained blue with DAPI.

Basal cells are a local stem cell for pulmonary airways; they reside below the columnar epithelium and serve as a regenerative cell source for epithelium of the proximal airways. FIGS. 36A-C demonstrates cells that are positive for cytokeratin-14, which is a basal cell marker. For comparison, native lung is shown in FIG. 36A. In addition, dual staining for cytokeratin-14 and CCSP is shown in FIG. 37, which also demonstrates that the Clara cells are lining the airway and the basal cells lying beneath them, consistent with their normal anatomic locations. These cells are sometimes found beneath larger airway structures, consistent with their location in native lung (FIG. 36B), but are also found in clusters that do not appear to be associated with large airways (FIG. 36C).

In addition to epithelial and endothelial cell growth, mesenchymal cells can repopulate the decellularized lung scaffolds. FIGS. 38A-B shows immunofluorescence staining of α-actin, which stains smooth muscle and myofibroblasts. These engineered tissues were cultured under the same conditions that were shown to favor epithelial growth. It was also observed that mesenchymal cells were found to be located beneath and between the developing epithelial structures, consistent with their location in native lung. Therefore, the results presented herein demonstrate that the decellularized scaffolds are also suitable substrates for the growth of mesenchymal cells, and that the viable mesenchymal cells were contained within the population of neonatal pulmonary cells.

Effect of Media Composition on Epithelial Differentiation

Medium type can have significant effects on cell growth and differentiation, and thus on the development of engineered lung tissues. In order to investigate some of these differences in more detail, the growth of engineered lung cultures using a serum-free media (BGJb) versus a serum-containing media (DMEM+10% FBS) on epithelial differentiation was compared. In these experiments, cells were first seeded onto the scaffolds in DMEM+10% FBS and allowed to culture in this medium for 2 days, after which a gradual 4-day transition to BGJb (serum-free) media occurred, with the final 2 days of culture in pure BGJb media. The transition to serum-free medium caused substantial effects on the expression of surfactant. It was observed that serum-free medium lead to a more apical expression of surfactant (SPC) as compared to DMEM+10% FBS (FIGS. 39C and 39D). This corresponds to significantly increased expression of surfactant on Western blot with the serum-free medium (BGJb) (FIG. 40; compare lanes labeled 'DMEM' and 'BGJb'). In addition, the form of surfactant was much more consistent with native lung (with most surfactant noted as the 21 kDa pro-SPC form in BGJb medium).

In addition, the transition to serum-free medium lead to a decrease in CCSP expression, noted via immunofluorescence in FIGS. 39F and 39E). In both medium types, diffuse CCSP expression was observed in the lumens of the developing epithelial structures. It is believed that this phenotype was due to lack of perfusion or ventilation, as these cultures were performed in small tissue slices.

Effect of Air-Liquid Interface on Lung Development in the Bioreactor

In order to create an air-liquid interface, the engineered lungs were cultured first for 4 days under ventilation with media, to allow cell attachment and proliferation. For the final 4 days of culture, the ventilation was switched from media to filtered room air.

Ventilation with air caused severe damage to the airway epithelium as well as destructive changes to some alveolar walls (FIGS. 19A-C). Therefore, the tidal volume used for air ventilation was reduced by approximately 50%, from the previous value of ~2.0-2.5 ml for liquid or air breathing in an effort to reduce the damage caused to native lungs by air ventilation.

Changes in cell attachment or morphology due to the presence of air ventilation in the bioreactor was not observed. However, it was observed that ventilation with air in engineered lungs cultured in the bioreactor led to induced expression of aquaporin, a differentiation marker for type I epithelium. This was noted both in cells in the parenchyma, which typically stained solely for surfactant protein C (indicate of type II epithelium) as well as occasional staining of cuboidal cells in developing epithelial structures. The observed staining patterns indicate that it is highly likely that most of the aquaporin-expressing cells also express SPC. As can be seen from FIG. 42B, virtually all of the cells in the parenchyma express SPC, while a subset of the parenchymal cells express AQP (FIG. 41A).

Figure 40:
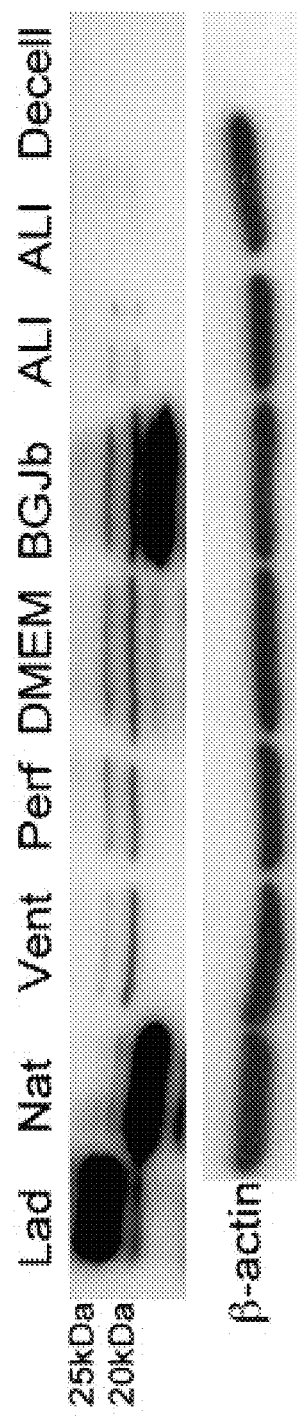
FIG. 40 is an image depicting surfactant expression in engineered epithelial tissues. 'Lad' is a protein ladder; the indicated bands are 20 and 25 kDa; 'Nat' is native lung tissue; 'Vent' is engineered lung tissue ventilated with DMEM medium; 'Perf' is engineered lung tissue perfused with DMEM medium; 'DMEM' is statically cultured engineered lung in DMEM medium; 'BGJb' is statically cultured engineered lung in BGJb medium; 'ALI' are engineered lung ventilated with air; and 'Decell' is decellularized scaffold.

These findings are highly suggestive that the air-liquid interface is inducing differentiation of type II epithelium to type I epithelium. Type II epithelium is a known local progenitor cell for type I epithelium, and so this differentiation is not surprising [Adamson et al., 1974, Lab Invest 30:35-42; Fehrenbach, 2001, Respir Res 2:33-46]. Furthermore, reduced expression of surfactant protein C in air-ventilated engineered lungs was observed, as shown in FIG. 40 (compare lanes 'ALI' to lungs that were ventilated with medium ('Vent') and perfused ('Perf'). This is also consistent with the differentiation of type II to type I epithelium. In addition, the growth of a number of ciliated epithelial cells was observed, as shown in FIGS. 42A-B. This likely a result of the introduction of an air interface. When airway epithelium is cultured in vitro, the transition of the cells from liquid to the air interface induces cilia expression [You et al., 2002, Am J Physiol Lung Cell Mol Physiol 283:L1315-21; Davidson et al., 2004, J Cyst Fibros 3 Suppl 2:59-62]. Furthermore, the lack of an air-liquid interface can lead to reduced ciliogenesis [Ostrowski et al., 1995, Exp Lung Res 21:957-70; Yeh et al., 2007, Laryngoscope 117:1439-44]. Therefore, in some instances, air interface has important impacts on regeneration of lung tissue in vitro.

Effect of Perfusion and Ventilation on the Development of Epithelial Structures in Engineered Lung Tissues Perfusion and ventilation can have significant impacts on the culture of lung tissue in the bioreactor. Ventilation also has significant impacts on the lung epithelial development, including the differentiation of types I and II pneumocytes [Inanlou et al., 2005, Histol Histopathol 20:1261-6; Inanlou et al., 2005, Dev Dyn 233:772-82; Inanlou et al., 2005, Dev Dyn 232:43-54]. As a result, the effects of perfusion and ventilation on engineered lung development during 8-day cultures in the bioreactor were compared. For these experiments, the conditions were the same as utilized during the validation experiments discussed elsewhere, with culture medium of DMEM+10% FBS, uncoated scaffolds, and an unsorted neonatal pulmonary cell population. However, cultures were either perfused through the vasculature at 2 ml/min or ventilated continuously with medium at 1 breath/min.

Figure 50:
FIG. 50 is an image demonstration of tight junction formation between endothelial cells in engineered lung tissue. Endothelial cells are marked with asterisks, separated by an extended cell-cell junction. Scale bar is 500 nm.

Many of the cells that form epithelial structures stain positive for CCSP, as shown in FIG. 50. Staining for CCSP in ventilated cultures were observed, but the cells attained a more flattened morphology. This may indicate that ventilation is inducing the CCSP-expressing cells to differentiate towards alveolar epithelium (either type I or II pneumocytes).

In the absence of ventilation, the lumens of developing epithelial structures were filled with an eosinophilic, and thus likely proteinaceous, material, visible on H&E staining in FIGS. 43A-B. This material also stained positive for CCSP, as seen in FIGS. 45A-B. This buildup of CCSP indicates that the Clara cells lining these epithelial structures are producing CCSP. In addition, the removal of this material with ventilation indicates that the airway tree is still intact and can conduct fluid, and furthermore suggests that these developing epithelial structures are a part of the airway tree and do not proliferate randomly within the matrix.

Perfusion versus ventilation did not have significant effects on the expression of SPC, as shown in FIGS. 46A-B. The majority of cells were positive for SPC under both ventilation and perfusion conditions.

Example 5: Endothelial Development in Engineered Lung Tissues

The following experiments were designed to determine whether decellularized scaffolds are able to support the growth of engineered lung endothelium, and to evaluate the effects of several specific factors on the development of engineered endothelium, with a focus on the ability of these factors to impact the formation of a functional endothelial barrier between the vascular and airway compartments.

The materials and methods employed in these experiments are now described.

Materials and Methods

Scaffold Preparation

Decellularized scaffolds were prepared as described elsewhere herein.

Neonatal Cell Isolation and Seeding

Neonatal rat pulmonary cells were isolated as described elsewhere herein. Cells were seeded into the scaffolds as described elsewhere herein.

Endothelial Cell Culture

Rat lung microvascular endothelial cells were obtained from VEC Technologies (Renssalaer, N.Y.) and grown on fibronectin-coated (~1 µg/cm2, Gibco) tissue culture vessels in MCDB-131 complete media including 10% FBS and supplemental growth factors (VEC Technologies).

Optimized Conditions for Engineered Endothelial Culture

Scaffolds were coated with 1 mg of fibronectin (Gibco) perfused through the vasculature in 60 ml of PBS at 37° C., then rinsed with PBS and media. Each scaffold was seeded twice at days 0 and 2 or 3 of culture with 8-10 million rat lung microvascular EC at each time point (two T150 culture flask was used per lung for each of two seedings). Cells were trypsinized from tissue culture plates using 0.25% tryspin (Gibco), filtered through a 40 µm filter to remove cell clumps, and injected into the pulmonary artery as a single bolus injection in ~3 ml of media. After allowing cell adherence for 1 hour, perfusion was begun through the vasculature at ~1.5 ml/min. After 1-2 hours, the perfusion rate was increased to 3 ml/min for the remainder of the culture period of 7-10 days. Medium was changed every 3-4 days.

Immunofluorescence

Tissue samples were prepared and stained as described elsewhere herein.

Transmission Electron Microscopy (TEM)

Samples were prepared and analyzed as described elsewhere herein.

Microparticle Retention

An assay was developed to evaluate the permeability of whole rat lungs to smaller particles, which have sizes on the order of large macromolecules. In this assay, the leakage of a FITC-labelled dextran solution across the airway-vascular barrier was quantified. FITC-labelled dextran with a molecular weight of 2,000,000 Da was obtained from Sigma (St Louis, Mo.). Assay validation was performed by measuring the permeability of native lung and native lung that was treated with 0.025% trypsin for 2 min. Lungs were perfused with heparinized PBS and connected to the usual bioreactor cannulae. A baseline lavage sample was obtained, and then the trypsin-treated lung was perfused with 10 ml of 0.025% trypsin in PBS and allowed to dwell for 2 min at RT, then rinsed with 10 ml of PBS. The FITC-labelled dextran solution (1 mg/ml) was injected into the pulmonary artery, and then flushed with 20 ml of PBS. Two lavage samples were then immediately taken in succession from the trachea. Fluorescence was measured using a fluorescent plate reader and data were fit to a standard curve. When performed on decellularized or engineered lungs, the assay was performed through the airway, as with the microsphere assay (see section 3.2.9). Thus, the FITC-dextrans were injected into the airway, and the vasculature was flushed with PBS.

The results of the experiments are now described.

Figure 47:
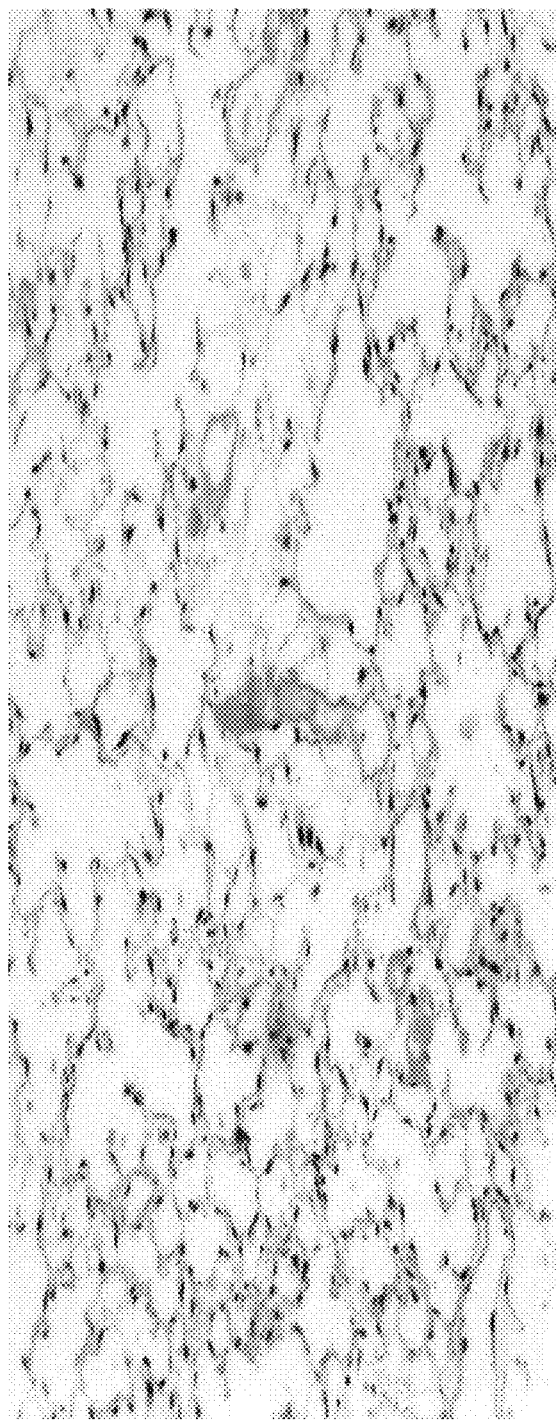
FIG. 47 is an image depicting an H&E stain of a fibronectin-coated decellularized scaffold seeded with rat lung microvascular endothelial cells.

Cell source: A commercially purchased source of rat lung microvascular EC was used. When these cells were seeded into the scaffolds that were fibronectin-coated and cultured in the presence of EC-specific medium, substantial growth of endothelial cells was observed, as shown in FIG. 47.

Summary of endothelial screening experiments: The screening experiments discussed elsewhere herein allowed for the identification of a set of conditions that was compatible with engineered endothelial culture. Outcomes were assessed primarily via histology for cell viability and expression of PECAM on immunofluorescence. The result of these pilot studies was a set of conditions that enables endothelial cell growth inside the scaffolds, such that the impact of discrete conditions on engineered lung endothelium can be systematically evaluated.

The conditions that were identified as suitable for the culture of engineered endothelium were: the use of a purified, in vitro expanded population of rat lung microvascular EC; fibronectin-coated scaffolds; and the use of EC-specific medium (MCDB-131 with 10% FBS and supplemental growth factors).

Validation of FITC-Dextran Permeability Assay

An assay to evaluate the permeability of whole rat lungs to small particles, which have sizes on the order of large macromolecules was developed. In this assay, the leakage of a FITC-labelled dextran solution across the airway-vascular barrier was quantified. This assay can be used repeatedly over the course of a culture, involves materials that are cell culture-friendly, and provides a measure of the permeability of the entire lung. In addition, if the assay is performed immediately before fixation, the FITC-dextran could be identified on histologic sections using anti-FITC antibodies.

The FITC-labelled dextran has a molecular weight of 2,000,000 Da. For a mono-disperse dextran, the Stokes-Einstein radius (nm) is related to molecular weight by rs=0.0488 (MW) 0.437 [Venturoli et al., 2005, Am J Physiol Renal Physiol 288:F605-13; Oliver et al., 1992, J Am Soc Nephrol 3:214-28]. For a 2 MDa dextran, this yields a radius of 27.7 nm. This assay was validated by evaluating the permeability of native lung and native lung that was made 'leaky' by brief perfusion of the vasculature with dilute trypsin. The FITC-labelled dextran solution was injected into the pulmonary artery, and then flushed with saline. Two lavage samples were then immediately taken in succession from the trachea. As shown in FIGS. 48A-B, the permeability of lung is increased by trypsin treatment, as expected due to disruption of endothelial attachment to the basement membrane. However, even native lung provided a measurable leak via this assay. This degradation of vascular permeability is the result of delays between animal sacrifice and the injection of the dextran, as well as the handling of the lung tissue.

When performed on decellularized or engineered lungs, the assay was performed through the airway, as with the microsphere assay. Thus, the FITC-dextrans were injected into the airway, and the vasculature was flushed with saline. Dextrans that translocated into the vascular compartment were measured as leak. The assays were performed in this fashion because in decellularized or engineered lungs, the tissue is highly permeable to fluid and a return sample cannot be obtained after an airway lavage. As such, the dextran was injected into the air-way as a single bolus lavage, and the vasculature was flushed to measure leak of FITC-dextrans across the airway-vascular barrier.

Effects of Perfusion Versus Ventilation on Engineered Lung Endothelium

The following experiments where designed to evaluating the effects of specific conditions on the development of engineered endothelial tissues, with a focus on the formation of a functional endothelial barrier. The effects of culturing engineered lung endothelium with perfusion versus ventilation was compared. Both ventilation and perfusion with regards to endothelial cell survival and proliferation and the formation of cell-cell junctions using transmission EM was evaluated.

It was observed that perfusion substantially improved the growth of engineered lung endothelium, as shown on histology in FIGS. 48A-B. In addition, more apoptotic cells were observed with ventilation, as shown in FIGS. 49A-B and consistent with their poor appearance on H&E histology.

In addition, perfused and ventilated cultures were analyzed for the presence of cell junctions using transmission EM and VE-cadherin staining. Tight junctions between endothelial cells are an important means of barrier function, as they tightly link adjoining cells together and thus inhibit the movement of fluid between these paracellular spaces [Majno et al., 1961, J Biophys Biochem Cytol. 11:571-605]. If these cell junctions are weak or absent, fluid leak can occur out of the vasculature and cause pulmonary edema [Orfanos et al., 2004, Intensive Care Med 30:1702-14; Maniatis et al., 2008, Vascular Pharmacology 49:119-33].

Using TEM, cell-cell junctions in the perfused engineered tissues were observed, as shown in FIG. 50. Not all cells demonstrated tight junction formation.

Cell junction formation was assessed using immunofluorescence for VE-cadherin. Robust staining for VE-cadherin was found in perfused engineered lung endothelium, as shown in FIGS. 51A-B. Ventilated tissues were not stained for VE-cadherin due to their poor appearance on histology and TEM.

Assessment of Barrier Function of Engineered Lung Endothelium

The following experiments were designed to evaluate the ability of engineered lung endothelium to form a functional barrier between the vascular bed and the airspaces. This is important in order to reduce fluid leak into the alveoli and thus enable gas exchange, and it is a key component of the objectives for engineered lung tissue. In order to evaluate the barrier function provided by the lung endothelium, a permeability assay was used to measure the translocation of small (55 nm) FITC-dextran particles from the airspaces into the vasculature. This assay was developed and validated as described elsewhere herein.

Figure 52:
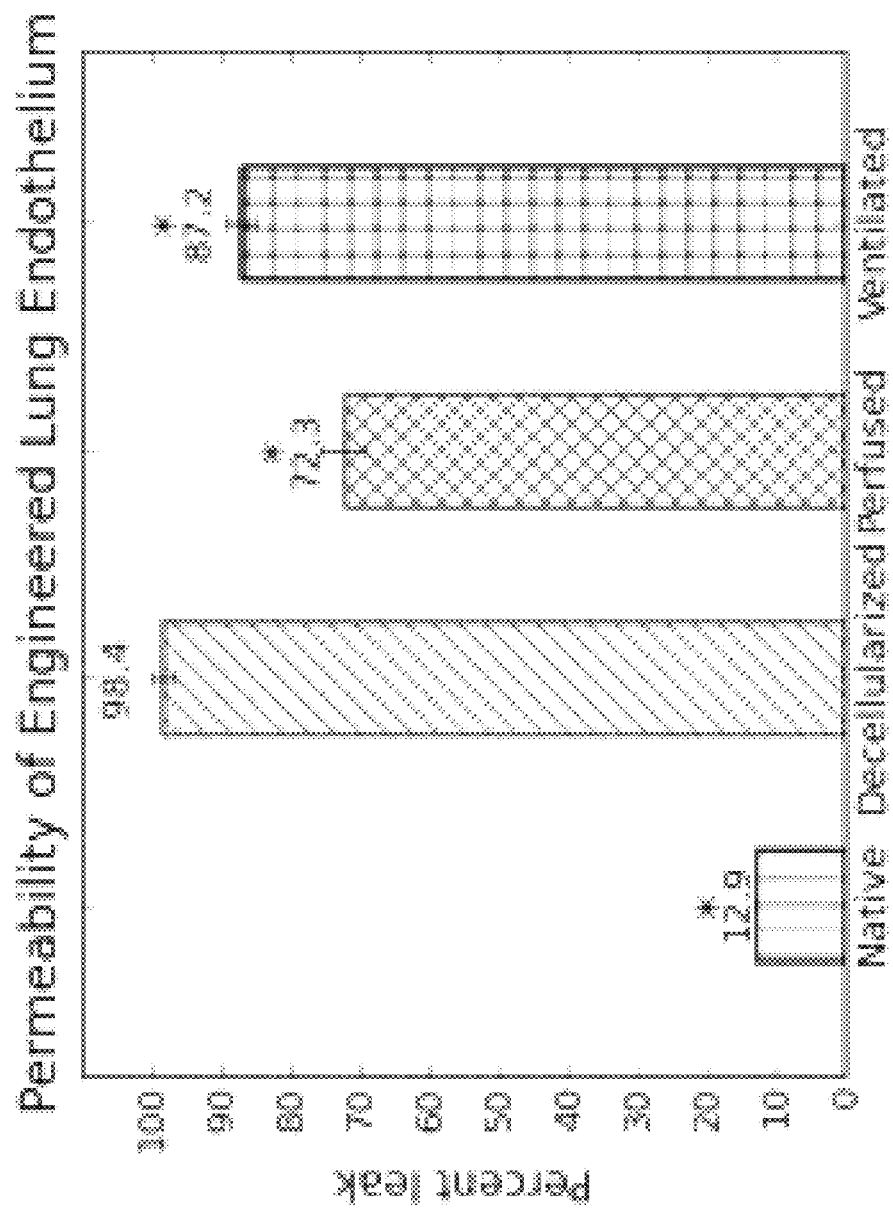
FIG. 52 is a chart depicting the permeability of engineered lungs seeded with endothelial cells alone to 2 megadalton FITC-labelled dextrans. * indicates p<0.05 compared to decellularized scaffolds.
Figure 53:
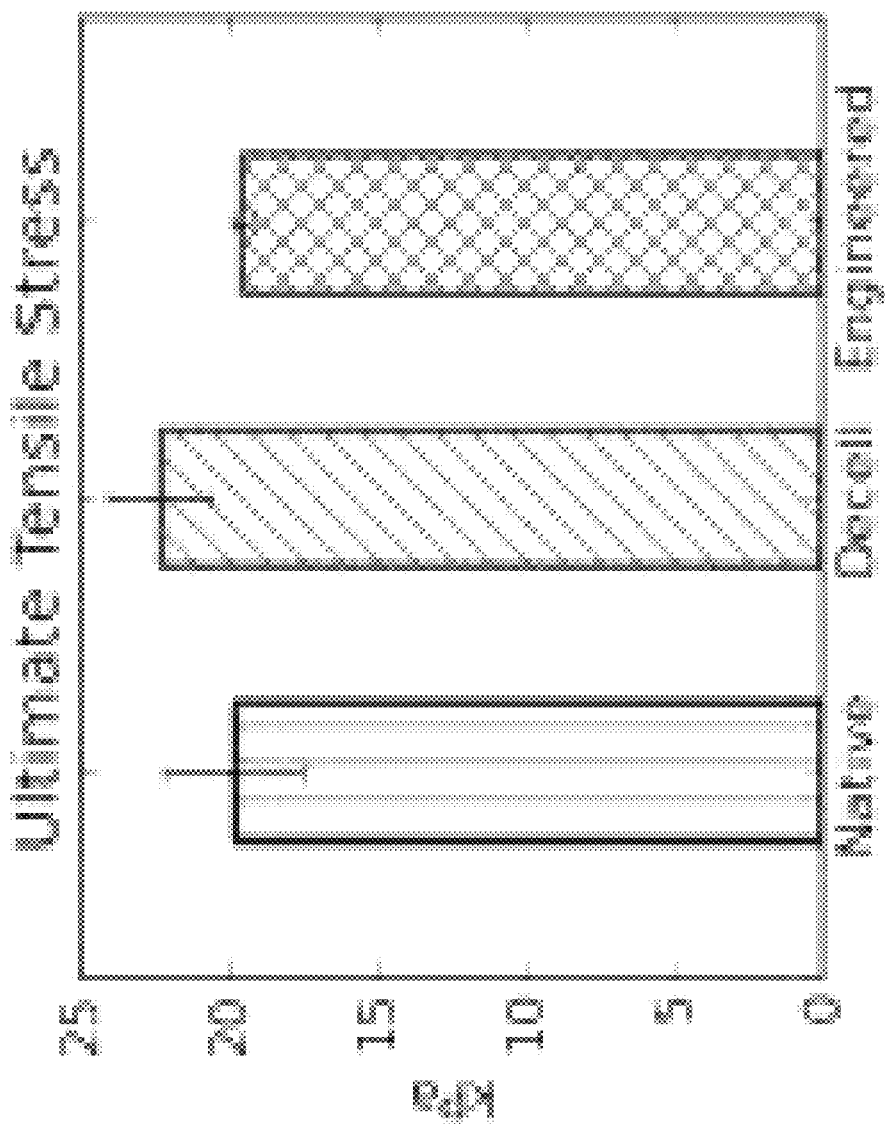
FIG. 53 is a chart depicting the ultimate tensile strength of engineered tissues. Native and decellularized lung strengths are also shown.

For this assay, FITC-dextran was injected into the airway compartment, and the amount that leaked across the alveolar-vascular barrier was measured by flushing the vasculature with saline. For decellularized scaffolds, there was essentially no barrier function to such small particles, with virtually all (98.4%) of the dextran translocating the alveoli into the vasculature and recovered with vascular rinsing. This compares to native lung, which when treated similarly shows a leak of 12.9% (FIG. 52).

In engineered lung endothelial tissues that were perfused, retention of up to 30% of dextrans in the airway compartment was demonstrated, after culture periods of 7-10 days. Ventilated endothelial tissues demonstrated a permeability of 87%.

These findings for perfused engineered lung endothelium, especially when coupled with the findings of robust VE-cadherin expression via immunofluorescence (FIGS. 51A-B) and cell-cell junction formation via TEM, indicate that the formation of a functional endothelial barrier in engineered endothelial tissues has occurred.

Figure 63A:
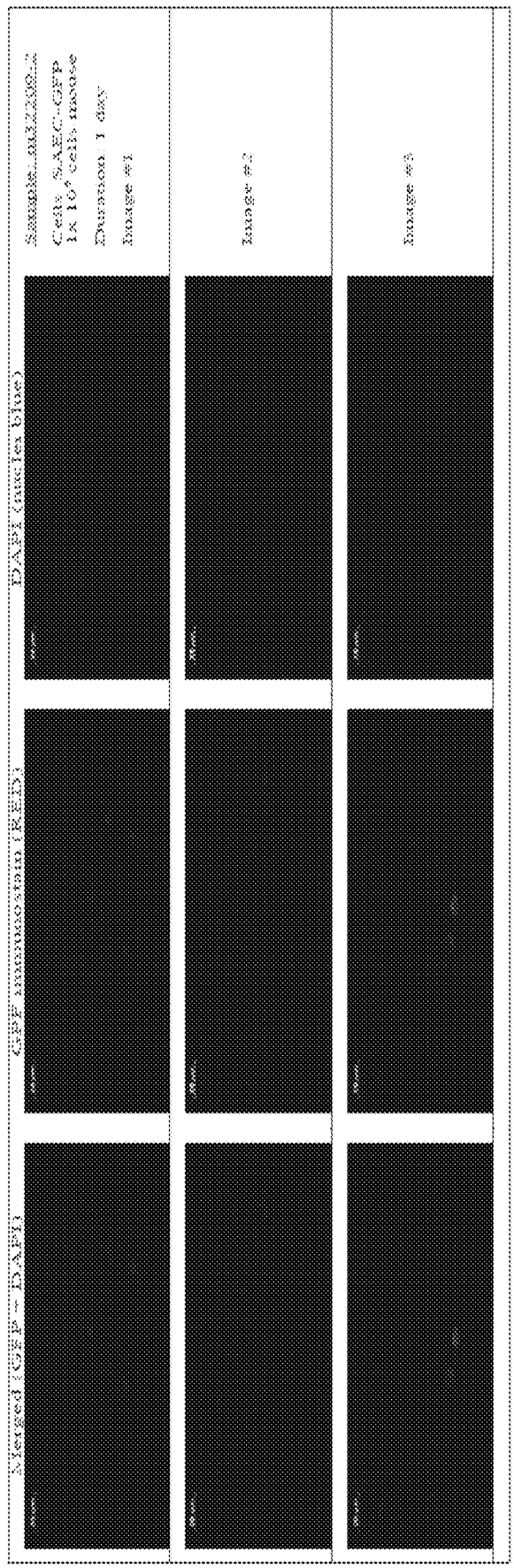
FIGS. 63A through 63C are a series of images demonstrating that that GFP positive human airway epithelial cells (both NHBE and SAEC) were found in mouse lungs for days after instillation into the airway.
Figure 63B:
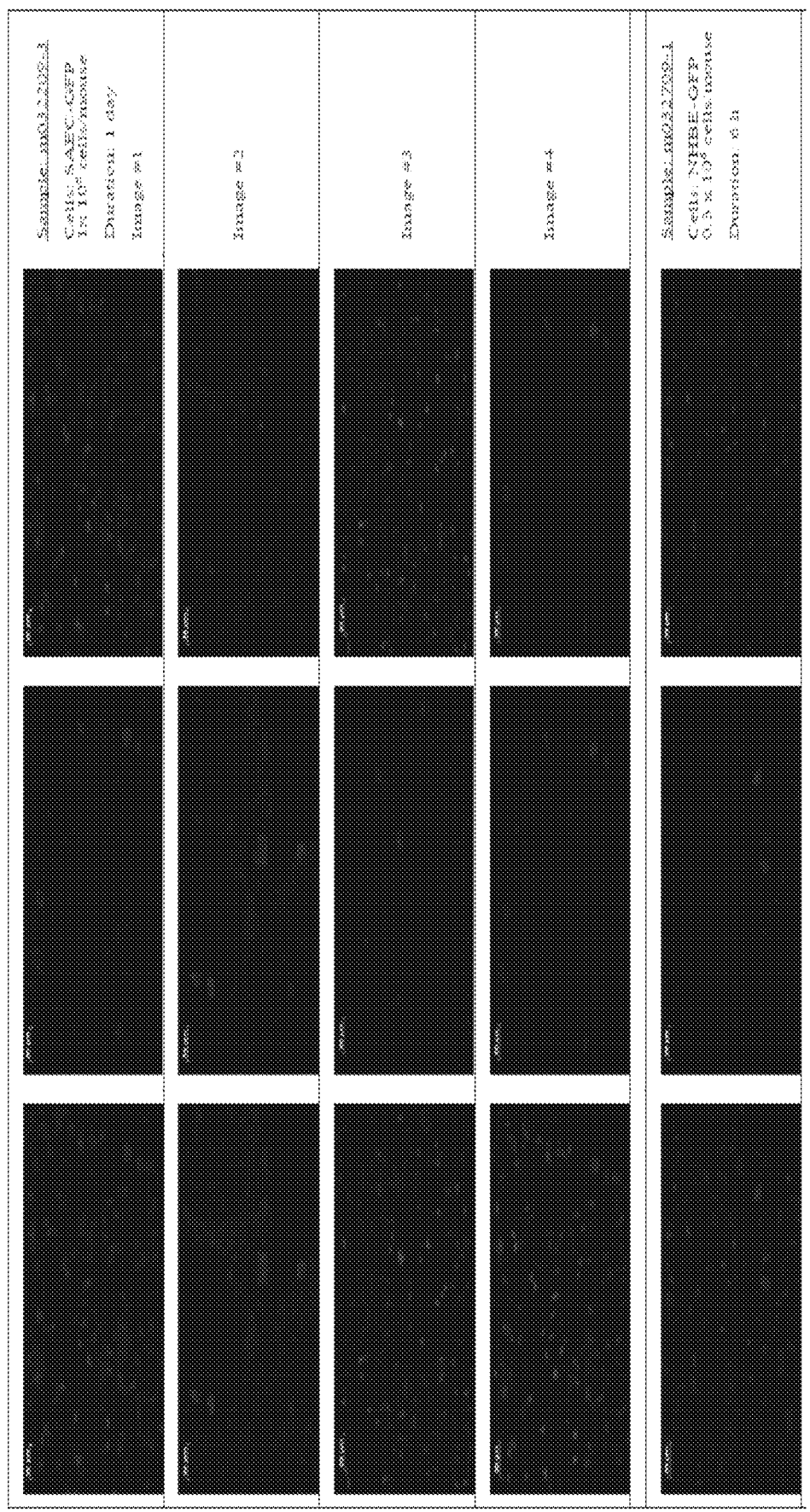
Figure 63C:
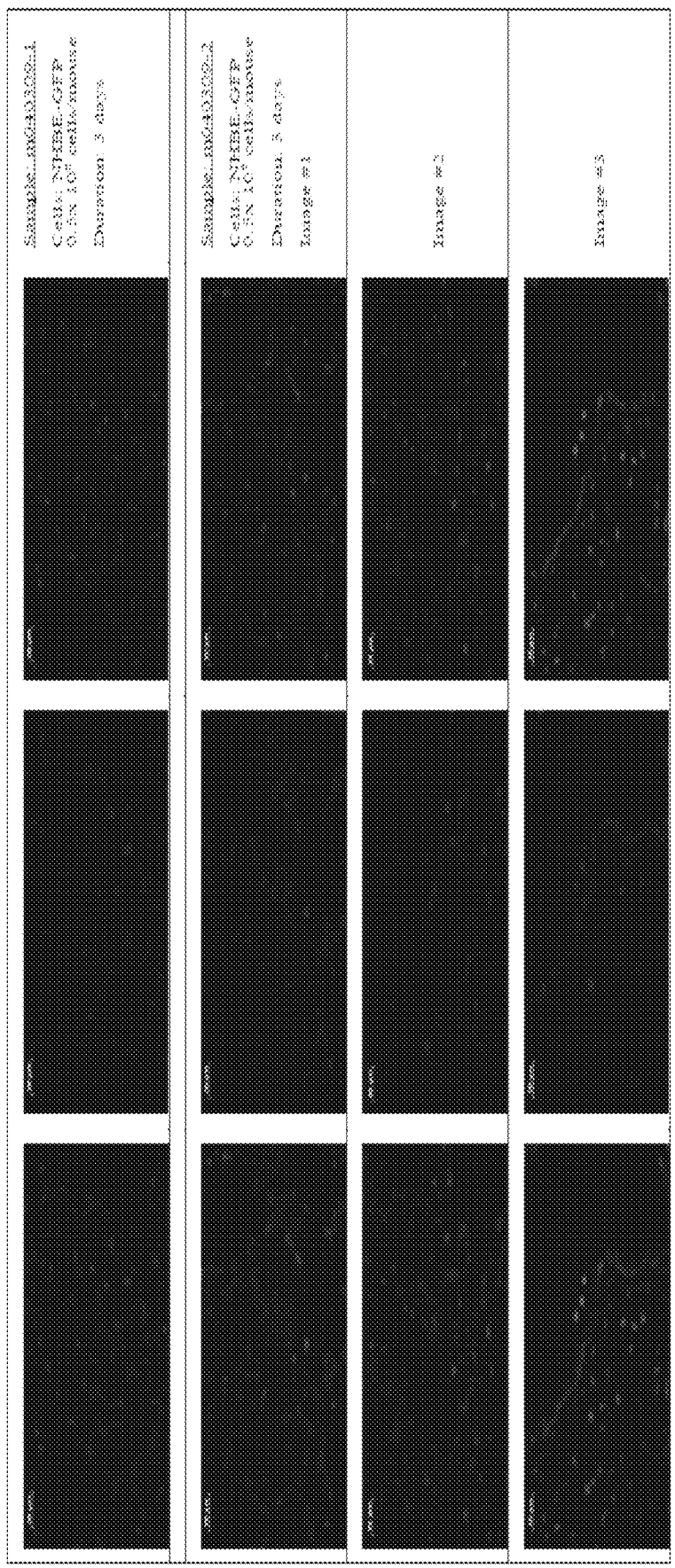

FIG. 63 is a chart depicting the ultimate tensile strength of engineered tissues. Native and decellularized lung strengths are also shown. This figure shows that the ultimate tensile stress of the engineered tissues is comparable to both native lung and to decellularized matrix. Therefore, the mechanical properties of tissue engineered lungs are maintained after the recellularization process.

Example 6: Lung Cell Therapy

The results presented herein demonstrate the use of decellularized lung tissues to effect lung cell therapy in a mammal. Generally, the steps include decellularization of a trachea, detection of extracellular matrix components within the decellularized tracheal tissue, culture of either human bronchial (large airway) and small airway pulmonary epithelial cells on the decellularized tracheal matrix, gene therapy of human pulmonary epithelial cells with a desired gene, and instillation of human pulmonary epithelial cells into lung via instillation, with verification of cell attachment and survival in the recipient lung.

Decellularization of Trachea

Pig trachea was harvested and rinsed in PBS to remove blood. A piece was cut and fixed with 10% neutral-buffered formalin, embedded in paraffin and cut into 5-mm sections. The rest was cut into 5 rings and incubated in CHAPS buffer (pH13.5) with stirring for 2-24 hours, with CHAPS buffer changed at 2 h, 4 h and 8 h time points. At the indicted time, tissue was removed from CHAPS buffer and rinsed with PBS. A piece was cut and fixed with 10% formalin and processed for histological analysis to confirm decellularization.

It was observed that decellularized trachea prepared with incubation in CHAPS buffer for 4-8 hours maintained collagen matrix and had most of cells removed from the tissue (except the cartilage layer). See FIG. 55. The following experiments were based on 6 h CHAPS incubation with stirring for preparation of decellularized trachea.

Figure 56:
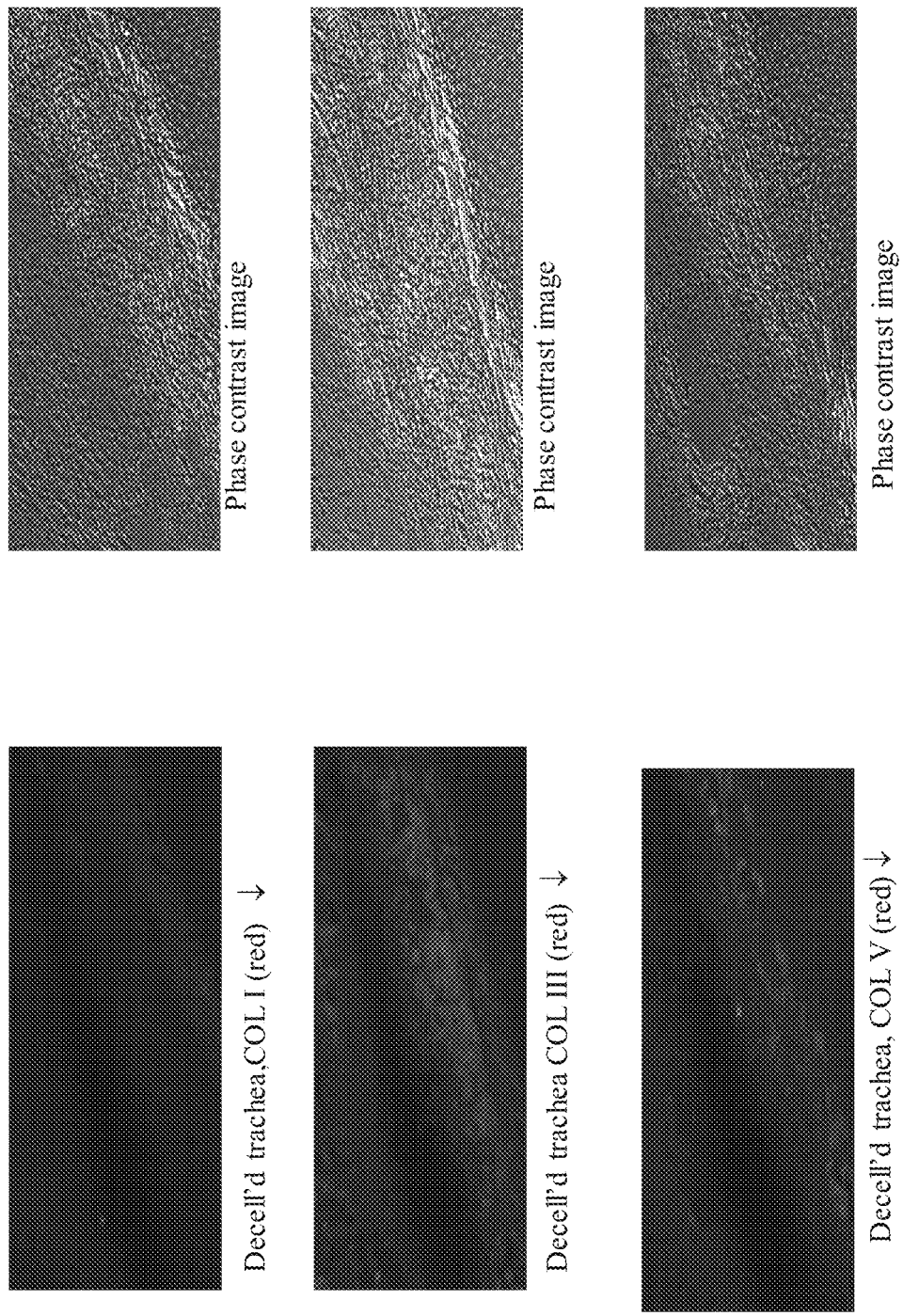
FIG. 56 is a series of images demonstrating that decellularized trachea contained all the three types of COL seen in native trachea.

These experiments were designed to detect extracellular matrix in trachea before and after decellularization. Briefly, a piece of tissue was cut from native and decellularized trachea and fixed with 10% formalin. 5 μm paraffin-embedded sections were stained with H&E and Masson's Trichrome. Paraffin-embedded sections were also immunostained for extracellular matrix proteins including collagen (COL), fibronectin (FN) and laminin (LN). Sections were deparaffinized, rehydrated, antigen retrieved (using Proteinase K) and blocked. In-house-raised rabbit anti-human FN, COL I, COL III, COL IV, COL V or LN antibodies were applied to sections, followed by Alexa Fluor 546-conjugaeted goat anti-rabbit IgG. Slides were counterstained with DAPI. It was observed that native trachea stained positive for COL I, COL III, COL V, but not the other ECM proteins. Decellularized trachea contained all the three types of COL seen in native trachea. See FIG. 56. These results suggest that decellularized trachea tissue support airway epithelial cell adhesion, growth and differentiation in vitro.

Growing Airway Epithelial Cells on Decellularized Trachea Tissue

The next set of experiments was designed to grow cells on decellularized tissue. Briefly, human bronchial/tracheal epithelial cells (NHBE) were cultured in bronchial epithelial growth medium (BEGM). Decellularized trachea (6 h CHAPS buffer incubation) was rinsed extensively (at least 24 h) with sterile PBS. The cartilage layer (as well as the adventitial layer) was peeled off, leaving the trachea mucosal and submucosal layer for subsequent cell seeding. Tissue was cut to about 5×5 cm² in size and put on transwell insert (0.4 μm pore size) in 6-well plate, with the epithelial surface facing up.

Figure 57:
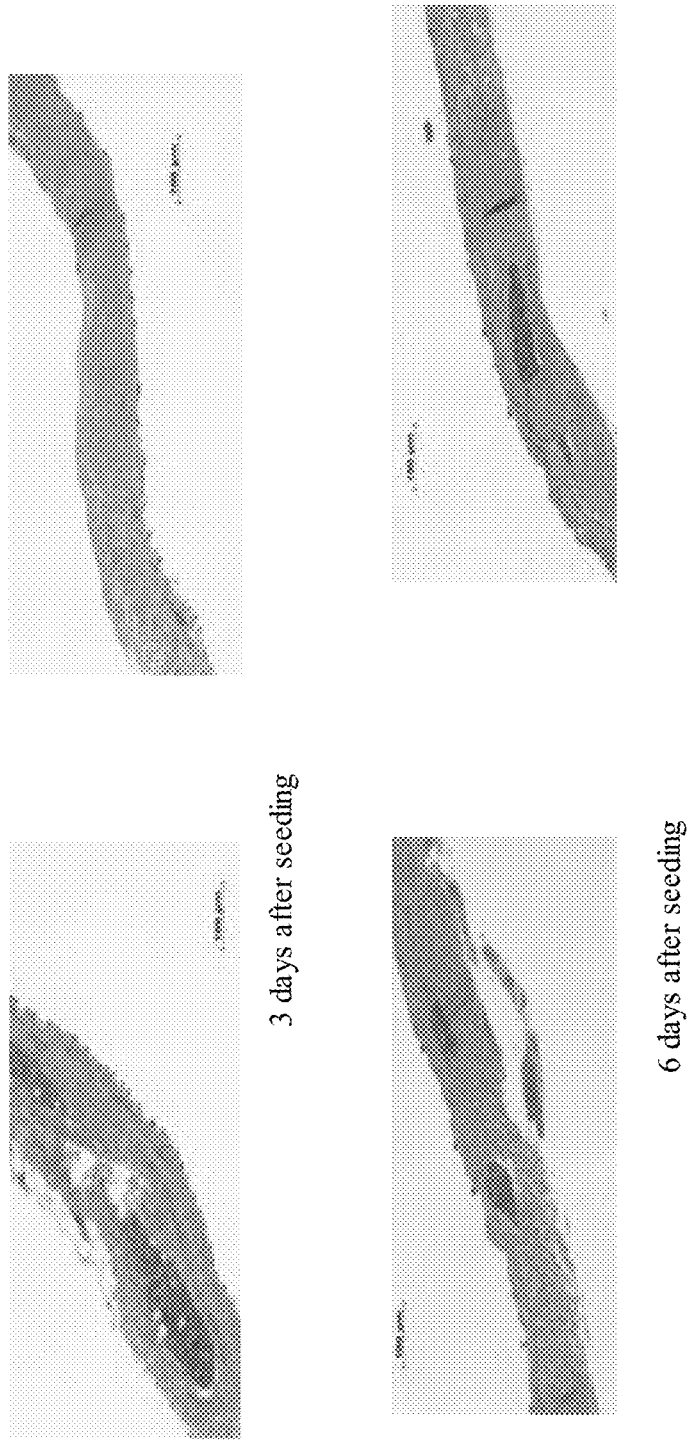
FIG. 57 is a series of images demonstrating that decellularized trachea supported NHBE adhesion and growth.

Cells were seeded on decellularized trachea tissue as follows. 50 μl cells (at 3.5×10⁶ cells/ml) were added to the epithelial surface of the decellularized trachea tissue and incubated for 30 mins at 37° C. Fresh culture media was then added to both the upper and lower sides of transwell insert, and cells were incubated for additional time. At the indicated time, tissues were removed from the transwell and fixed with 10% formalin. Paraffin-embedded 5 μm sections were stained with H&E. It was observed that decellularized trachea supported NHBE adhesion and growth. See FIG. 57.

Figure 58:
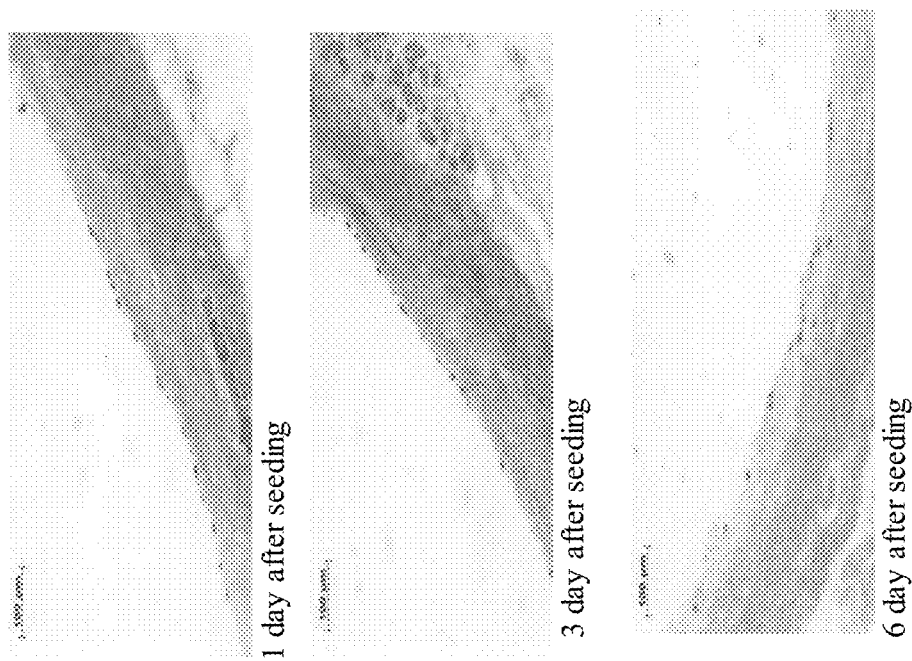
FIG. 58 is a series of images demonstrating that decellularized trachea supported SAEC adhesion and growth.

The next set of experiments were designed to grow human small airway epithelial cells (SAEC) that were transfected with a transgene on decellularized tissue. Briefly, human SAECs were transfected with GFP Retrovirus for 6 h. Cells were seeded on decellularized trachea tissue in 6-well plates as follows. 50 μl cells (at 5×10⁶ cells/ml) were added to the epithelial surface of the decellularized trachea tissue (about 0.5×1.0 cm²) and incubated for 30 min at 37° C. Fresh culture media were then added and cells were incubated for additional time. It was observed that decellularized trachea also supported SAEC adhesion and growth. See FIG. 58. In addition, decellularized trachea supported the adhesion and growth of SAEC that had been transfected with GFP, as a proof-of-principle of culturing human pulmonary epithelial cells that have been transfected with a gene of interest.

Gene Therapy of Airway Epithelial Cells

The next set of experiments was designed to determine the feasibility of using the decellularized tissue for gene therapy for lung cells. Genetic modification was performed as follows. EGFP (enhanced GFP) retrovirus supernatant was prepared using Phoenix packaging cell line. EGFP DNA was inserted in the LZRSpBMN vector. NHBE and SAEC were grown until over 80% confluent. On the day of infection, cells were rinsed a few times and inoculated with virus supernatant (containing 8 μg/ml polybrene) for 6 h at 37° C. Cells were rinsed a few times and incubated in fresh media overnight. Cells were then analyzed for GFP using flow cytometry. It was observed that the infected cells stained positive for GFP. For example, NHBE cells exhibited an 18.5% positive staining for GFP compared to non-infected cells. SAEC cells exhibited a 16% positive staining for GFP compared to non-infected cells. The results presented herein demonstrate the ability to infect human pulmonary epithelial cells with a gene of interest in this culture system, using a retrovirus. However, other means of delivering a transgene is also encompassed in the invention. For example, the next set of experiments were designed to test the feasibility of using a lentivirus system.

Infection with GFP lentivirus was performed as follows. EGFP Lentivirus supernatant was prepared in 293T cells in serum free medium. GFP DNA was inserted in the pSicoR vector with CMV promoter. NHBE were seeded onto 6-well plate at 1×10⁵ cells/well and incubated at 37° C. for 1 day (80-90% confluent). On day of infection, cells were rinsed a few times and then inoculated with virus supernatant (1:3 diluted with fresh BEGM) (containing 8 μg/ml polybrene) for 6 h at 37° C. Cells were rinsed a few times and then incubated with fresh media for additional 2 days. Cells were fixed with 4% paraformaldehyde for 30 min and examined microscopically. See FIG. 59. The results are summarized in Table 2:

TABLE 2

| Samples | Total cells | GFP + cells | Infection % |
|---|---|---|---|
| Control | 0.996 × 10⁶ | 0 | |
| 6 h | 1.190 × 10⁶ | 0.635 × 10⁶ | 52.7 |
| 20 h | 0.972 × 10⁶ | 0.638 × 10⁶ | 64.9 |
| 6 h + 6 h | 0.727 × 10⁶ | 0.389 × 10⁶ | 53.6 |
| 20 h + 20 h | 0.420 × 10⁶ | 4564 | 10.7 |

The results presented herein demonstrate that NHBE infected with GFP lentivirus did not show obvious morphology change after 6 h. One-time infection for 6 h produced over 50% GFP positive cells assessed by flow cytometry. Infection efficiency for SAEC also appeared to be over 50%. The results presented herein demonstrate that any desired gene can be used to generate genetically modified lung cells.

Injection of Airway Epithelial Cells into Mouse Lungs

Figure 60:
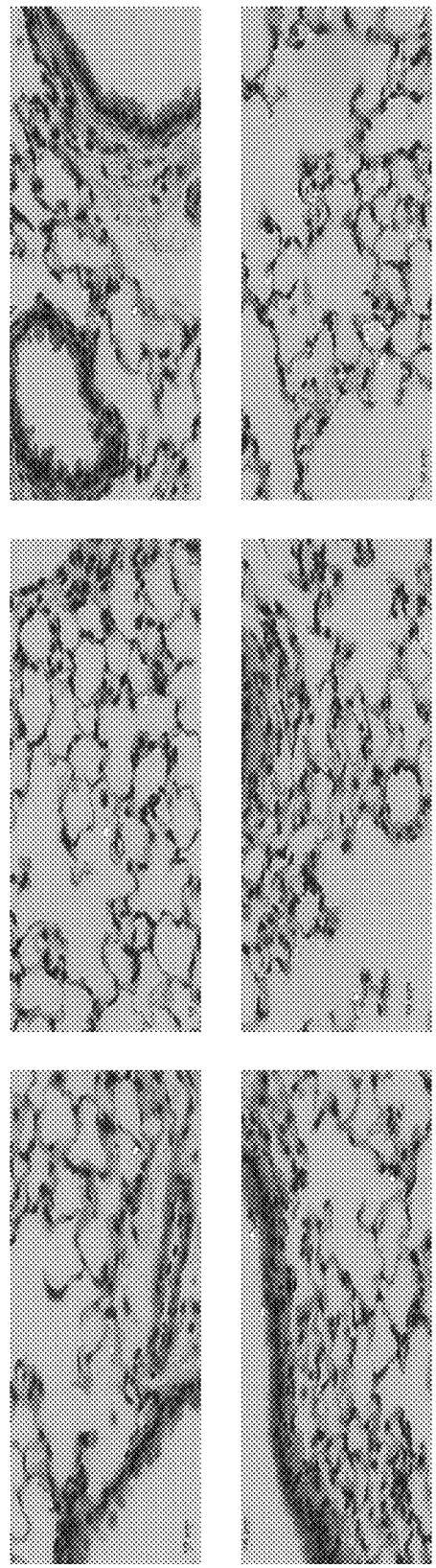
FIG. 60 is a series of images demonstrating that significant numbers of microspheres were present in every lobe of the mouse lung following delivery by instillation into the airway.

The next experiments were designed to determine the feasibility of injecting airway epithelial cells into a mammalian lung. Briefly, 100 μl of 1:1 mixture of 5 μm microspheres and PBS was injected through trachea into C57BL/6J mouse, female, ~10 weeks old (Jackson Lab). The mouse survived for a few minutes after injection. Lung was harvested immediately and fixed with formalin. 5 μm paraffin-embedded sections were stained with H&E. This study was done as an initial feasibility study to determine if cell-sized particles that were delivered by instillation into the airway would be detected within mammalian lungs. Results from H&E images of mouse lung with injected microspheres demonstrated that significant numbers of microspheres were present in every lobe of the mouse lung. See FIG. 60. The results demonstrate that injection using the trachea approach works for cell instillation.

Figure 61:
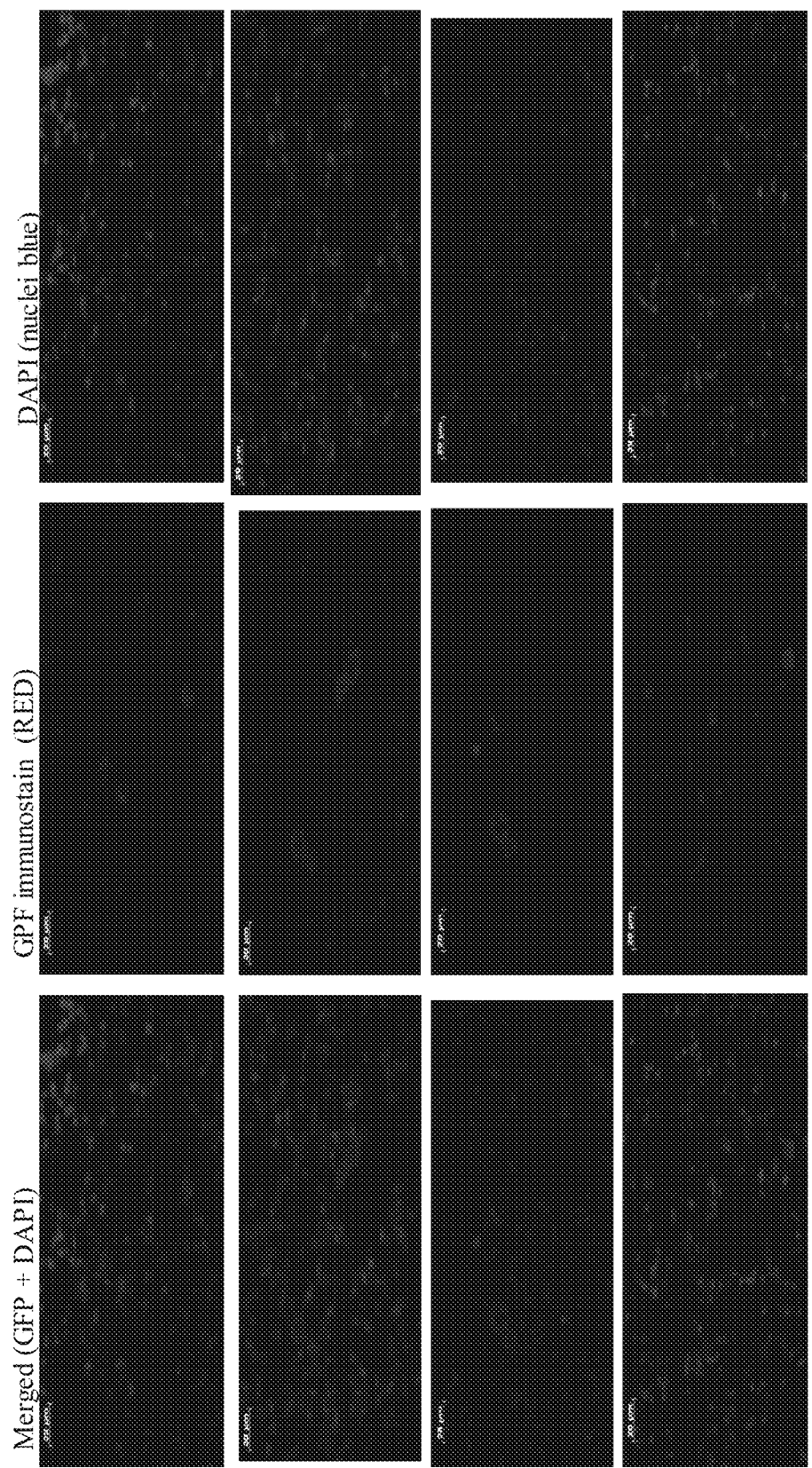
FIG. 61 is a series of images demonstrating the successful injection of cells into the lungs, and that human epithelial cells that have been transduced with a transgene (GFP) adhered to lung epithelium.

The next set of experiments included injecting GFP labeled cells into explanted mouse lungs. Briefly, cells were infected with GFP retrovirus with 6 h. C57BL/6J mice were euthanized, trachea exposed and the proximal end tied off with suture. 100 μl of GFP retrovirus-infected SAEC were injected through trachea (followed by 200 μair to push the cells in) into the lungs of mice. The distal end of the trachea was tied off. Lung was explanted and fixed immediately with 10% formalin. 5 μm paraffin-embedded sections were deparaffinized, rehydrated, antigen retrieved (using 10 mM Citric Acid buffer, pH 6), permeabilized (with Triton X) and blocked. Rabbit polyclonal anti-GFP antibody (from Abcam) was applied to sections, followed by Alexa Fluor 555-conjugaeted goat anti-rabbit IgG. Slides were counterstained with DAPI. It was observed that GFP positive cells were found in the explanted lungs. See FIG. 61. The results presented herein demonstrate the successful injection of cells into the lungs, and that human epithelial cells that have been transduced with a transgene (GFP) adhered to lung epithelium.

Figure 62:
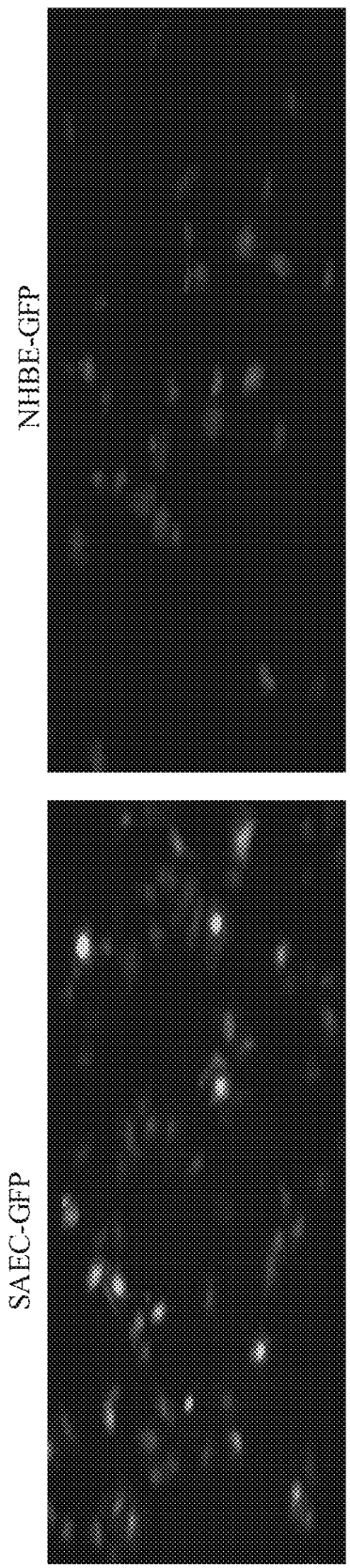
FIG. 62 is a series of images depicting GFP cells used for injection as seen before trypsinization.

The next set of experiments was designed to determine the feasibility of injecting of GFP-labeled cells into mouse lungs. Briefly, mice (C57BL/6J, female, ~10 weeks old) were anesthetized and trachea was exposed. 100 μl of GFP retrovirus infected-human airway epithelial cells were injected through trachea (followed by 200 μl air) into the lungs. See FIG. 62. Mice were allowed to recover for 6 h to 3 days. On day of harvest, the lung was perfused with PBS through pulmonary artery to remove blood, and then perfused with 10% formalin through trachea, and dissected. Harvested lung were fixed in formalin for another 4 hr. 5 μm paraffin-embedded sections were stained for GFP as discussed elsewhere herein. It was observed that GFP positive human airway epithelial cells (both NHBE and SAEC) were found in mouse lungs for days after instillation into the airway. See FIG. 63. This shows that human epithelial cells, that have been grown in culture and have been transduced with a transgene of interest, can be delivered into the lungs of a recipient mammal, and adhere to the recipient lung and survive and proliferate.

Example 7: Implantation of Decellularized Engineered Lung

This experiment was designed to show the feasibility of implanting a decellularized, engineered lung into a living rat recipient. A decellularized engineered rat lung was prepared according to previous examples. An adult male laboratory rat was anesthetized with intraperitoneal injection of ketamine and xylazine. The rat was then tracheally intubated and ventilated with 100% oxygen mixed with Forane to maintain anesthesia. Under sterile conditions, the thorax was opened via median sternotomy. The ribs were retracted bilaterally, revealing normally inflating lungs and the beating heart. Following systemic heparinization, the native left lung was excised in toto. Then, the decellularized engineered lung was anastomosed to the recipient's pulmonary artery, pulmonary vein, and left mainstem bronchus using 10-0 suture under an operating microscope.

Figure 64A:
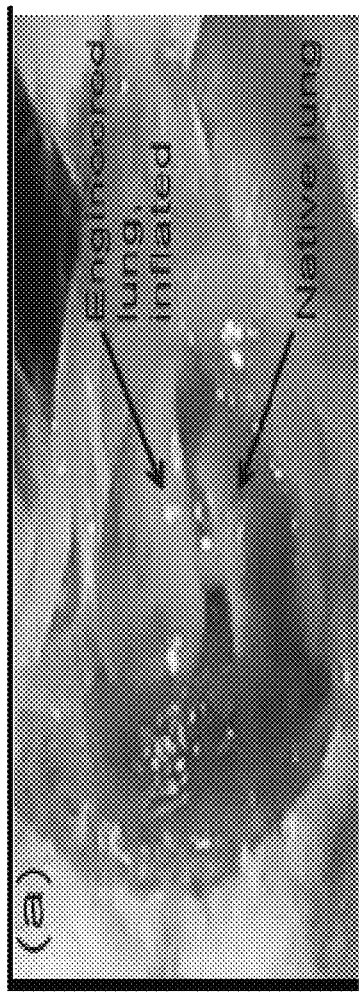
FIGS. 64A and 64B are a series of images demonstrating the implanted engineered lung at inflation and deflation during the ventilatory cycle.
Figure 64B:
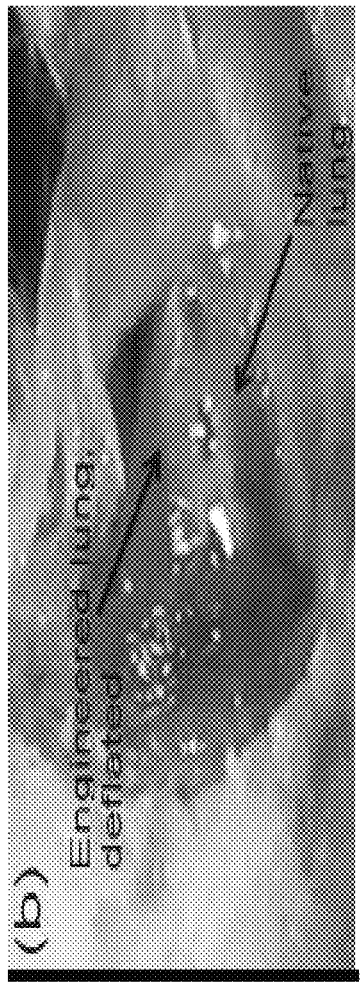

After removal of vascular clamps on the pulmonary artery and vein, blood was seen to perfuse the engineered lung in normal fashion. In addition, the implanted engineered lung was easily ventilated and cycled through inflation and deflation similar to the resident native right lung. FIGS. 64A-B shows photographs of the implanted engineered lung at inflation and deflation during the ventilatory cycle. Hence, the engineered lungs produced using the techniques herein are both implantable into a mammal, and are functional from the standpoint of enabling perfusion through the whole organ, and easy ventilation of the airway. During the entire implantation period, there was no evidence of bleeding or air leak from the implanted engineered lung.

The disclosures of each and every patent, patent application, and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed:

1. A decellularized lung tissue made by a method comprising perfusing a natural tissue comprising a capillary network with a decellularization solution, wherein the natural tissue is isolated from a mammal, wherein the decellularization solution comprises a solution hypertonic to cells in the tissue, a zwitterionic detergent, and a chelating agent, and wherein the decellularization solution removes cellular material and retains collagen, capillary structure, and structural integrity of the matrix similar to the natural tissue, further comprising monitoring a perfusion pressure during the perfusing, and adjusting the perfusion pressure to maintain a pressure of less than 30 mmHg, wherein the decellularized lung tissue comprises an intact airway network that does not contain major histocompatibility complex (MHC) Class I and II antigens, wherein the decellularized lung tissue retains vascular structures substantially similar to native tissue and exhibits a mechanical property substantially similar to that of a corresponding natural tissue prior to decellularization, and wherein the decellularized lung tissue comprises an ultimate tensile strength (UTS) that is indistinguishable from the UTS of the natural tissue.

2. The decellularized lung tissue of claim 1, wherein the decellularized lung tissue is a lung tissue comprising an alveolar basement membrane.

3. The decellularized lung tissue of claim 1, wherein the decellularized lung tissue comprises an intact alveolar basement membrane.

4. The decellularized lung tissue of claim 1, wherein the decellularized lung tissue exhibits a morphology substantially similar to that of an otherwise identical tissue prior to decellularization.

5. The decellularized lung tissue of claim 1, wherein the decellularized lung tissue retains an extracellular matrix of the corresponding natural tissue, wherein the extracellular matrix comprises an exterior surface that is substantially intact.

6. The decellularized lung tissue of claim 1, wherein immunogenic markers have been substantially removed from the tissue.

7. The decellularized lung tissue of claim 1, wherein the mechanical property of the decellularized lung tissue is at least one property selected from the group consisting of elasticity and ultimate tensile strength.

8. The decellularized lung tissue of claim 1, wherein the zwitterionic detergent is CHAPS.

9. A decellularized lung tissue made by a method comprising perfusing a natural tissue comprising a capillary network with a decellularization solution, wherein the natural tissue is isolated from a mammal, wherein the decellularization solution comprises a solution hypertonic to cells in the tissue, a zwitterionic detergent, and a chelating agent, and wherein the decellularization solution removes cellular material and retains collagen, capillary structure, and structural integrity of the matrix similar to the natural tissue, monitoring a perfusion pressure during the perfusing and adjusting the perfusion pressure to maintain a pressure of less than 30 mmHg, wherein the decellularized lung tissue comprises an intact airway network that does not contain major histocompatibility complex (MHC) Class I and II antigens, wherein the decellularized lung tissue comprises intact blood vessels and an airway network, and wherein the decellularized lung tissue comprises an ultimate tensile strength (UTS) that is indistinguishable from the UTS of the natural tissue.

10. The decellularized lung tissue of claim 9, wherein the decellularized lung tissue does not contain α-actin.

11. The decellularized lung tissue of claim 9, wherein the decellularized lung tissue comprises an intact alveolar basement membrane.

12. The decellularized lung tissue of claim 9, wherein the zwitterionic detergent is CHAPS.

13. An engineered tissue composition comprising
a three dimensional scaffold and
a population of cells,
wherein the three dimensional scaffold comprises a decellularized lung tissue prepared by a method comprising
perfusing a natural tissue comprising a capillary network with a decellularization solution,
wherein the natural tissue is isolated from a mammal, wherein the decellularization solution comprises a solution hypertonic to cells in the tissue, a zwitterionic detergent, and a chelating agent, and wherein the decellularization solution removes cellular material and retains collagen, capillary structure, and structural integrity of the matrix similar to the natural tissue, monitoring a perfusion pressure during the perfusing, and adjusting the perfusion pressure to maintain a pressure of less than 30 mmHg, wherein the decellularized lung tissue comprises an intact airway network that does not contain major histocompatibility complex (MHC) Class I and II antigens, wherein the decellularized lung tissue retains vascular structures substantially similar to native tissue, wherein the composition is capable of supporting and maintaining the differentiation state of a lung cell, wherein the composition exhibits a mechanical property substantially similar to that of a corresponding natural tissue, and wherein the decellularized lung tissue comprises an ultimate tensile strength (UTS) that is indistinguishable from the UTS of the natural tissue.

14. The composition of claim 13, wherein the composition exhibits an intact airway tree and vascular network.

15. The composition of claim 13, wherein the population of cells comprises a stem cell.

16. The composition of claim 13, wherein the population of cells comprises epithelial and endothelial cells.

17. The composition of claim 13, wherein the cells are genetically modified to express a gene.

18. The composition of claim 17, wherein the gene is cystic fibrosis transmembrane conductance regulator (CFTR).

19. The composition of claim 13, wherein the composition is capable of supporting and maintaining the differentiation state of an alveolar epithelial cell.

20. The composition of claim 13, wherein the scaffold further comprises a biocompatible material selected from the group consisting of fibronectin, laminin, collagen, glycoprotein, thrombospondin, elastin, fibrillin, mucopolysaccharide, glycolipid, heparin sulfate, chondroitin sulfate, keratin sulfate, glycosaminoglycan, hyaluronic acid, proteoglycan, vitronectin, poly-D-lysine, polysaccharide, and combinations thereof.

21. The composition of claim 13, wherein the composition comprises cells that exhibit gene expression associated with induction of branching morphogenesis.

22. The composition of claim 13, wherein the engineered tissue composition has a characteristic selected from the group consisting of branching morphogenesis, distal lung epithelial cytodifferentiation, epithelial growth, vascular development, and combinations thereof.

23. The composition of claim 13, wherein the zwitterionic detergent is CHAPS.

* * * * *